(12) United States Patent
Blouin et al.

(10) Patent No.: US 10,374,162 B2
(45) Date of Patent: Aug. 6, 2019

(54) FULLERENE DERIVATIVES

(71) Applicants: Merck Patent GmbH, Darmstadt (DE); Nano-C, Inc., Westwood, MA (US)

(72) Inventors: Nicolas Blouin, Darmstadt (DE); Stephane Berny, Bristol (GB); Edward A. Jackson, Ayer, MA (US); Henning Richter, Newton, MA (US)

(73) Assignees: Merck Patent GmbH, Darmstadt (DE); Nano-C, Inc., Westwood, MA (US)

( * ) Notice: Subject to any disclaimer, the term of this patent is extended or adjusted under 35 U.S.C. 154(b) by 159 days.

(21) Appl. No.: 15/312,448

(22) PCT Filed: May 26, 2015

(86) PCT No.: PCT/EP2015/001073
§ 371 (c)(1),
(2) Date: Nov. 18, 2016

(87) PCT Pub. No.: WO2015/192942
PCT Pub. Date: Dec. 23, 2015

(65) Prior Publication Data
US 2017/0092866 A1   Mar. 30, 2017

Related U.S. Application Data

(60) Provisional application No. 62/013,431, filed on Jun. 17, 2014.

(51) Int. Cl.
| | | |
|---|---|---|
| *H01L 51/00* | (2006.01) | |
| *C07C 35/44* | (2006.01) | |
| *C07C 69/157* | (2006.01) | |
| *C07C 69/16* | (2006.01) | |
| *H01L 35/24* | (2006.01) | |
| *C07C 69/12* | (2006.01) | |
| *H01L 51/42* | (2006.01) | |

(52) U.S. Cl.
CPC .......... *H01L 51/0047* (2013.01); *C07C 35/44* (2013.01); *C07C 69/12* (2013.01); *C07C 69/157* (2013.01); *C07C 69/16* (2013.01); *H01L 35/24* (2013.01); *H01L 51/0036* (2013.01); *H01L 51/0043* (2013.01); *C07C 2604/00* (2017.05); *H01L 51/4253* (2013.01); *Y02E 10/549* (2013.01)

(58) Field of Classification Search
CPC ............. H01L 51/0047; H01L 51/0043; H01L 51/0036; H01L 35/24; H01L 51/4253; C07C 69/12; C07C 35/44; C07C 69/157; C07C 69/16; C07C 2604/00; Y02E 10/549
USPC ........................ 252/500, 502, 510
See application file for complete search history.

(56) References Cited

U.S. PATENT DOCUMENTS

| | | | |
|---|---|---|---|
| 2014/0026948 A1 | 1/2014 | Ihn et al. | |
| 2016/0322575 A1* | 11/2016 | Yan ........................ | C08K 3/04 |
| 2017/0294585 A1* | 10/2017 | Morse .................... | C07C 13/62 |

FOREIGN PATENT DOCUMENTS

| | | |
|---|---|---|
| CN | 102070133 A | 5/2011 |
| EP | 2 457 898 A1 | 5/2012 |
| JP | 2012-094829 A | 5/2012 |
| WO | WO 2009/086210 A2 | 7/2009 |
| WO | WO 2014/173484 A1 | 10/2014 |
| WO | WO 2014/202184 A1 | 12/2014 |
| WO | WO 2015/096797 A1 | 7/2015 |

OTHER PUBLICATIONS

International Search Report received in connection with international application No. PCT/EP2015/001073, dated Aug. 10, 2015.
He, Y. et al., High-performance polymer photovoltaics based on rationally designed fullerene acceptors, Soar Energy Materials and Solar Cells, vol. 118, Sep. 8, 2013, pp. 171-178, XP028720943.
He, Y. et al., "High performance low band gap polymer solar cells with a non-conventional acceptor" Chemical Communications, col. 48, No. 61, (2012); pp. 7616-7618, XP55025092.
Matsuo, Y. et al.: "Addition of Dihydromethano Group to Fullerenes to Improve the Performance of Bulk Heterojunction Organic Solar Cells" Advanced Materials, vol. 25, No. 43, Aug. 29, 2013, pp. 6266-6269, XP55205477.
Wong, W.W.H. et al.: "Single Isomer of Indene-C70 Bisadduct-Isolation and Performance in Bulk Heterojunction Solar Cells", Chemistry of Materials, vol. 26, No. 4, Feb. 13, 2014, pp. 1686-1689, XP55205538.

(Continued)

*Primary Examiner* — Douglas J McGinty
(74) *Attorney, Agent, or Firm* — The Marbury Law Group, PLLC

(57) ABSTRACT

The invention relates to fullerene derivatives of formula I, to mixtures and formulations containing them, to the use of the fullerene derivatives, mixtures and formulations as organic semiconductors in, or for the preparation of electronic devices, especially organic photovoltaic (OPV) devices and organic photodetectors (OPD), and to electronic devices comprising, or being prepared from, these fullerene derivatives, mixtures or formulations.

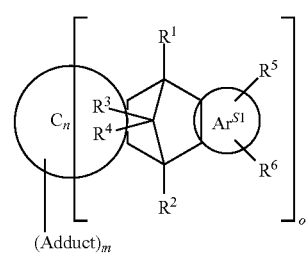

30 Claims, 2 Drawing Sheets

(56) References Cited

OTHER PUBLICATIONS

Khylabich, P.P. et al.:"Efficient Ternary Blend Bulk Heterojunction Solar Cells with Tunable Open-Circuit Voltage" Journal of the American Chemical society, vol. 113, No. 37,pp. 14534-14537,XP55205483.
Kang, H. et al., "Controlling Number of Indene Solubilizing Groups in Multiadduct Fullerenes for Tuning Optoelectronic Properties and open-Circuit Voltage in Orhanic Solar Cells" ACS Applied materials and interfaces, vol. 4, No. 1, 2011, pp. 110-116, XP5520557 4.

* cited by examiner

FULLERENE DERIVATIVES

TECHNICAL FIELD

The invention relates to novel fullerene derivatives, to methods for their preparation and educts or intermediates used therein, to mixtures and formulations containing them, to the use of the fullerene derivatives, mixtures and formulations as organic semiconductors in, or for the preparation of, electronic devices, especially organic photovoltaic (OPV) devices and organic photodetectors (OPD), and to electronic devices comprising, or being prepared from, these fullerene derivatives, mixtures or formulations.

BACKGROUND

In recent years, there has been development of organic semiconducting (OSC) materials in order to produce more versatile, lower cost electronic devices. Such materials find application in a wide range of devices or apparatus, including organic field effect transistors (OFETs), organic light emitting diodes (OLEDs), organic photodetectors (OPDs), organic photovoltaic (OPV) cells, sensors, memory elements and logic circuits to name just a few. The organic semiconducting materials are typically present in the electronic device in the form of a thin layer, for example of between 50 nm and 1 μm thickness.

The photosensitive layer in an OPV or OPD device is typically composed of at least two materials, a p-type semiconductor such as a polymer, an oligomer or a define molecular unit and a n-type semiconductor such as a fullerene derivative, graphene, a metal oxide, or quantum dots. In recent years, many p-type semiconductors, mainly polymers, have been prepared to enhance the performance of an OPV device. In comparison, the development of n-type semiconductor has been limited to only a few selected candidates.

Novel n-type semiconductors as promising alternative to PCBM-$C_{60}$ fullerene are limited. FIG. 1 shows some known fullerene derivatives, including Fullerene F1 and the respective multiple adducts both described in WO2008/018931 and WO2010/087655, Fullerene F2 and the respective multiple adducts both described in U.S. Pat. No. 8,217,260, Fullerene F3 described in JP 2012-094829, Fullerene F4 described in WO 2009/008323 and JP 2011-98906 and Fullerene F5 and the respective multiple adducts both described in JP 2011-181719. However, the physical properties of these fullerene derivatives, such as solubility, light stability and thermal stability, are limiting their use in commercial applications.

OPV devices containing a derivative of Fullerene F2, namely the mono- and bis-indene-$C_{60}$ fullerene as described in U.S. Pat. No. 8,217,260, have been reported to show increased power conversion efficiency (PCE) through open circuit voltage ($V_{oc}$) increase while maintaining similar short circuit potential ($J_{sc}$) to equivalent devices with PCBM-$C_{60}$ using P3HT as donor polymer to form the bulkheterojunction (BHJ). However, the mono-indene fullerene solubility is limited, resulting in poor coating quality, thus limiting the industrial use of the compound, while the bis-indene fullerene multicomponent mixture is not suited for amorphous polymers resulting in poor BHJ morphology and thus poor $J_{sc}$.

Thus there is still a need for fullerene derivatives which are easy to synthesize, especially by methods suitable for mass production, show good structural organization and film-forming properties, exhibit good electronic properties, especially a high charge carrier mobility, a good processability, especially a high solubility in organic solvents, and high light and thermal stability.

It is an aim of the present invention to provide fullerene derivatives that provide one or more of the above-mentioned advantageous properties. Another aim of the invention is to extend the pool of n-type OSC materials available to the expert. Other aims of the present invention are immediately evident to the expert from the following detailed description.

The inventors of the present invention have found that one or more of the above aims can be achieved by providing substituted indene fullerenes of formula I as disclosed and claimed hereinafter.

Surprisingly it is found that these fullerenes demonstrate one or more of the improved properties as described above, especially for use in OPV/OPD applications, compared to the fullerenes disclosed in prior art. Besides, these fullerenes as disclosed and claimed hereinafter can also be used as semiconductors in other electronic devices like OFETs or OLEDs.

Only few mono- or bisindene fullerenes have been reported in prior art until now. The substituted monoindene $C_{70}$ fullerene A as shown in FIG. 2 has been reported in *Chem. Commun.*, 2012, 48, 7616-7618, while a monoindene $C_{60}$ with a exocyclic double bond at the 2 position (fullerene B) as shown in FIG. 2 has been reported in *Org. Lett.*, 2013, 15, 4030-4033. However, it has neither been disclosed nor suggested that these fullerenes can lead to BHJ OPV devices with improved thermal and/or light stability compared to PCBM-$C_{60}$.

Thus, until now substituted indene fullerenes have not been considered as potential replacement from PCBM type fullerene in the OPV or OPD device active layers nor for use as p-type or n-type semiconductors in OFET or OLED devices.

SUMMARY

The invention relates to compounds of formula I, including isomers thereof,

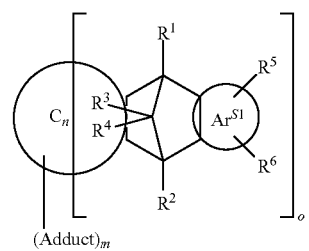

wherein
$C_n$ denotes a fullerene composed of n carbon atoms, optionally with one or more atoms trapped inside,
Adduct is a secondary adduct, or a combination of secondary adducts, appended to the fullerene $C_n$ with any connectivity,
m is 0, an integer≥1, or a non-integer>0,
o is an integer≥1,
$Ar^{S1}$ denotes an aryl or heteroaryl group with 5 to 20, preferably 5 to 15, ring atoms, which is mono- or polycyclic,
$R^1$ to $R^6$ denote, independently of each other, H, halogen, CN, $R^7$, $R^8$ or $R^9$, $R^7$ denotes, on each occurrence identically or differently, a saturated or unsaturated, non-aromatic carbo- or heterocyclic group, or an aryl, heteroaryl, aryloxy or heteroaryloxy group, wherein each of the aforementioned groups has 3 to 20 ring atoms, is mono- or polycyclic, does optionally contain fused rings, and is optionally substituted by one or more halogen atoms or CN groups, or by one or more identical or different groups $R^8$ or $R^9$, $R^8$ denotes, on each occurrence identically or differently, an alkyl group with 1 to 30 C atoms, which is straight-chain, branched or cyclic, and in which one or more $CH_2$ groups are optionally replaced by —O—, —S—, —C(=O)—, —C(=S)—, —C(=O)—O—, —O—C(=O)—, —NR°—, —C(=O)—NR°—, —NR°—C(=O)—, —SiR°R°°—, —CF$_2$—, —CHR°°=CR°°—, —CY$^1$=CY$^2$— or —C≡C— in such a manner that O and/or S atoms are not linked directly to one another, and in which one or more H atoms are optionally replaced by F, Cl, Br, I or CN, $R^9$ denotes, on each occurrence identically or differently, a straight-chain, branched or cyclic alkyl group with 1 to 50, preferably 2 to 50, more preferably 2 to 25, most preferably 2 to 12, C atoms, in which one or more $CH_2$ or $CH_3$ groups are replaced by a cationic or anionic group, $Y^1$ and $Y^2$ denote, independently of each other, H, F, Cl or CN, $R°$ and $R°°$ denote, independently of each other, H or an optionally substituted carbyl or hydrocarbyl group having 1 to 40 C atoms, with the provisos that
a) at least one of $R^1$, $R^2$, $R^3$ and $R^4$ is different from H, and
b) if n=70, then $R^1$ is different from —C(=O)—O—CH$_3$ if $R^2$ is H, and $R^2$ is different from —C(=O)—O—CH$_3$ if $R^1$ is H.

The invention further relates to the use of the compounds of formula I as electron acceptor or n-type semiconductor.

The invention further relates to the use of compounds of formula I as electron acceptor or n-type component in a semiconducting material, organic electronic device or component of an organic electronic device.

The invention further relates to a composition comprising one or more compounds selected from formula I.

The invention further relates to a composition comprising two or more fullerene derivatives, one or more of which are selected from formula I.

The invention further relates to a composition comprising one or more compounds selected from formula I, preferably as electron acceptor or n-type component, and further comprising one or more semiconducting compounds, which preferably have electron donor or p-type properties.

The invention further relates to a composition comprising one or more compounds selected from formula I, and further comprising one or more p-type organic semiconductor compounds, preferably selected from conjugated organic polymers.

The invention further relates to a composition comprising one or more compounds selected from formula I, and further comprising one or more compounds which are selected from compounds having one or more of a semiconducting, charge transport, hole transport, electron transport, hole blocking, electron blocking, electrically conducting, photoconducting, photoactive and light emitting property.

The invention further relates to the use of a compound selected from formula I, or a composition comprising it, as semiconducting, charge transport, electrically conducting, photoconducting, photoactive or light emitting material, or in an electronic device, or in a component of such an electronic device or in an assembly comprising such an electronic device or such a component.

The invention further relates to a semiconducting, charge transport, electrically conducting, photoconducting, photoactive or light emitting material, which comprises a compound selected from formula I or a composition comprising it as described above and below.

The invention further relates to a formulation comprising one or more compounds selected from formula I, or a composition or material comprising it as described above and below, and further comprising one or more solvents, preferably selected from organic solvents, very preferably from non-chlorinated organic solvents, most preferably from non-halogenated organic solvents.

The invention further relates to an electronic device, or a component thereof, or an assembly comprising it, which is prepared using a formulation as described above and below.

The invention further relates to an electronic device, or a component thereof, or an assembly comprising it, which comprises a compound selected from formula I, or a composition or a material comprising it as described above and below.

The electronic device is preferably an optical, electrooptical, electronic, photoactive, electroluminescent or photoluminescent device.

The electronic device includes, without limitation, organic field effect transistors (OFET), organic thin film transistors (OTFT), organic light emitting diodes (OLED), organic light emitting transistors (OLET), organic photovoltaic devices (OPV), organic photodetectors (OPD), organic solar cells, dye sensitized solar cells (DSSC), perovskite-based solar cells, solar cells, laser diodes, Schottky diodes, photoconductors, photodetectors and thermoelectric devices.

Preferred electronic devices are OFETs, OTFTs, OPVs, OPDs and OLEDs, in particular bulk heterojunction (BHJ) OPVs or inverted BHJ OPVs.

Further preferred is the use of a compound, composition or blend according to the present invention as dye in a DSSC or a perovskite-based solar cell, and a DSSC or a perovskite-based solar cell comprising a compound, composition or blend according to the present invention.

The components of the above electronic devices include, without limitation, charge injection layers, charge transport layers, interlayers, planarising layers, antistatic films, polymer electrolyte membranes (PEM), conducting substrates and conducting patterns.

The assemblies comprising such electronic devices or components include, without limitation, integrated circuits (IC), radio frequency identification (RFID) tags or security markings or security devices containing them, flat panel displays or backlights thereof, electrophotographic devices, electrophotographic recording devices, organic memory devices, sensor devices, biosensors and biochips.

In addition the compounds and compositions of the present invention can be used as electrode materials in batteries and in components or devices for detecting and discriminating DNA sequences.

The invention further relates to a bulk heterojunction which comprises, or is being formed from, a composition comprising one or more compounds selected from formula I and one or more p-type organic semiconductor compounds that are selected from conjugated organic polymers. The invention further relates to a bulk heterojunction (BHJ) OPV device, or an inverted BHJ OPV device, comprising such a bulk heterojunction.

TERMS AND DEFINITIONS

Figure 1:
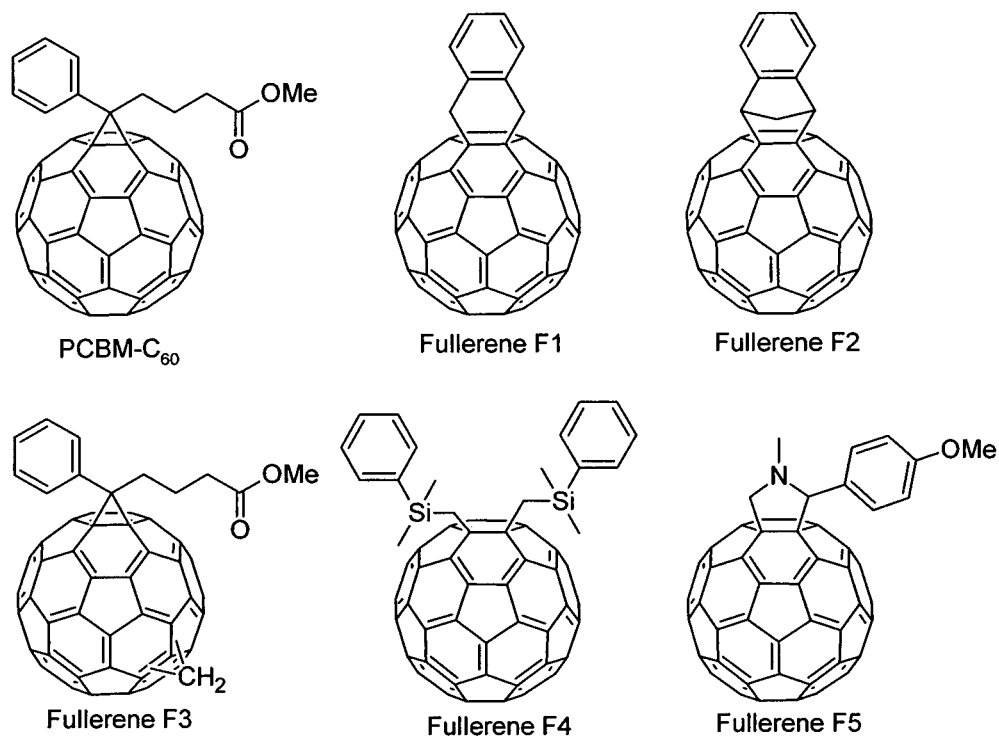
FIG. 1 and FIG. 2 show substituted fullerenes according to prior art.
Figure 2:
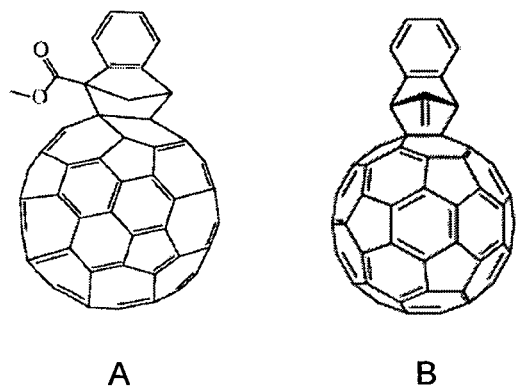

As used herein, any reference to "formula I" or "formula I and its subformulae" is understood to be inclusive of any specific subformula of formula I as shown hereinafter.

As used herein, the term "fullerene" will be understood to mean a compound composed of an even number of carbon atoms, which form a cage-like fused-ring having a surface which comprises six-membered rings and five-membered rings, usually with twelve five-membered rings and the rest six-membered rings, optionally with one or more atoms trapped inside. The surface of the fullerene may also contain hetero atoms like B or N.

As used herein, the term "endohedral fullerene" will be understood to mean a fullerene with one or more atoms trapped inside.

As used herein, the term "metallofullerene" will be understood to mean an endohedral fullerene wherein the atoms trapped inside are selected from metal atoms.

As used herein, the term "carbon based fullerene" will be understood to mean a fullerene without any atoms trapped inside, and wherein the surface is comprised only of carbon atoms.

As used herein, the term "polymer" will be understood to mean a molecule of high relative molecular mass, the structure of which essentially comprises the multiple repetition of units derived, actually or conceptually, from molecules of low relative molecular mass (*Pure Appl. Chem.*, 1996, 68, 2291). The term "oligomer" will be understood to mean a molecule of intermediate relative molecular mass, the structure of which essentially comprises a small plurality of units derived, actually or conceptually, from molecules of lower relative molecular mass (*Pure Appl. Chem.*, 1996, 68, 2291). In a preferred meaning as used herein present invention a polymer will be understood to mean a compound having>1, i.e. at least 2 repeat units, preferably≥5repeat units, and an oligomer will be understood to mean a compound with>1and<10, preferably<5, repeat units.

Further, as used herein, the term "polymer" will be understood to mean a molecule that encompasses a backbone (also referred to as "main chain") of one or more distinct types of repeat units (the smallest constitutional unit of the molecule) and is inclusive of the commonly known terms "oligomer", "copolymer", "homopolymer" and the like. Further, it will be understood that the term polymer is inclusive of, in addition to the polymer itself, residues from initiators, catalysts and other elements attendant to the synthesis of such a polymer, where such residues are understood as not being covalently incorporated thereto. Further, such residues and other elements, while normally removed during post polymerization purification processes, are typically mixed or co-mingled with the polymer such that they generally remain with the polymer when it is transferred between vessels or between solvents or dispersion media.

As used herein, in a formula showing a polymer or a repeat unit, an asterisk (*) will be understood to mean a chemical linkage to an adjacent unit or to a terminal group in the polymer backbone. In a ring, like for example a benzene or thiophene ring, an asterisk (*) will be understood to mean a C atom that is fused to an adjacent ring.

As used herein, the terms "repeat unit", "repeating unit" and "monomeric unit" are used interchangeably and will be understood to mean the constitutional repeating unit (CRU), which is the smallest constitutional unit the repetition of which constitutes a regular macromolecule, a regular oligomer molecule, a regular block or a regular chain (*Pure Appl. Chem.*, 1996, 68, 2291). As further used herein, the term "unit" will be understood to mean a structural unit which can be a repeating unit on its own, or can together with other units form a constitutional repeating unit.

As used herein, a "terminal group" will be understood to mean a group that terminates a polymer backbone. The expression "in terminal position in the backbone" will be understood to mean a divalent unit or repeat unit that is linked at one side to such a terminal group and at the other side to another repeat unit. Such terminal groups include endcap groups, or reactive groups that are attached to a monomer forming the polymer backbone which did not participate in the polymerisation reaction, like for example a group having the meaning of $R^{23}$ or $R^{24}$ as defined below.

As used herein, the term "endcap group" will be understood to mean a group that is attached to, or replacing, a terminal group of the polymer backbone. The endcap group can be introduced into the polymer by an endcapping process. Endcapping can be carried out for example by reacting the terminal groups of the polymer backbone with a monofunctional compound ("endcapper") like for example an alkyl- or arylhalide, an alkyl- or arylstannane or an alkyl- or arylboronate. The endcapper can be added for example after the polymerisation reaction. Alternatively the endcapper can be added in situ to the reaction mixture before or during the polymerisation reaction. In situ addition of an endcapper can also be used to terminate the polymerisation reaction and thus control the molecular weight of the forming polymer. Typical endcap groups are for example H, phenyl and lower alkyl.

As used herein, the term "small molecule" will be understood to mean a monomeric compound which typically does not contain a reactive group by which it can be reacted to form a polymer, and which is designated to be used in monomeric form. In contrast thereto, the term "monomer" unless stated otherwise will be understood to mean a monomeric compound that carries one or more reactive functional groups by which it can be reacted to form a polymer.

As used herein, the terms "donor" or "donating" and "acceptor" or "accepting" will be understood to mean an electron donor or electron acceptor, respectively. "Electron donor" will be understood to mean a chemical entity that donates electrons to another compound or another group of atoms of a compound. "Electron acceptor" will be understood to mean a chemical entity that accepts electrons transferred to it from another compound or another group of atoms of a compound. See also International Union of Pure and Applied Chemistry, Compendium of Chemical Technology, Gold Book, Version 2.3.2, 19. Aug. 2012, pages 477 and 480.

As used herein, the term "n-type" or "n-type semiconductor" will be understood to mean an extrinsic semiconductor in which the conduction electron density is in excess of the mobile hole density, and the term "p-type" or "p-type semiconductor" will be understood to mean an extrinsic semiconductor in which mobile hole density is in excess of the conduction electron density (see also, J. Thewlis, *Concise Dictionary of Physics*, Pergamon Press, Oxford, 1973).

As used herein, the term "leaving group" will be understood to mean an atom or group (which may be charged or uncharged) that becomes detached from an atom in what is considered to be the residual or main part of the molecule taking part in a specified reaction (see also *Pure Appl. Chem.*, 1994, 66, 1134).

As used herein, the term "conjugated" will be understood to mean a compound (for example a polymer) that contains mainly C atoms with sp²-hybridisation (or optionally also sp-hybridisation), and wherein these C atoms may also be replaced by hetero atoms. In the simplest case this is for example a compound with alternating C—C single and double (or triple) bonds, but is also inclusive of compounds with aromatic units like for example 1,4-phenylene. The term "mainly" in this connection will be understood to mean that a compound with naturally (spontaneously) occurring defects, or with defects included by design, which may lead to interruption of the conjugation, is still regarded as a conjugated compound.

As used herein, unless stated otherwise the molecular weight is given as the number average molecular weight Mn or weight average molecular weight Mw, which is determined by gel permeation chromatography (GPC) against polystyrene standards in eluent solvents such as tetrahydrofuran, trichloromethane (TCM, chloroform), chlorobenzene or 1,2,4-trichlorobenzene. Unless stated otherwise, 1,2,4-trichlorobenzene is used as solvent. The degree of polymerization, also referred to as total number of repeat units, n, will be understood to mean the number average degree of polymerization given as n=$M_n$/MU, wherein $M_n$ is the number average molecular weight and $M_U$ is the molecular weight of the single repeat unit, see J. M. G. Cowie, *Polymers: Chemistry & Physics of Modern Materials*, Blackie, Glasgow, 1991.

As used herein, the term "carbyl group" will be understood to mean any monovalent or multivalent organic moiety which comprises at least one carbon atom either without any non-carbon atoms (like for example —C≡C—), or optionally combined with at least one non-carbon atom such as B, N, O, S, P, Si, Se, As, Te or Ge (for example carbonyl etc.).

As used herein, the term "hydrocarbyl group" will be understood to mean a carbyl group that does additionally contain one or more H atoms and optionally contains one or more hetero atoms like for example B, N, O, S, P, Si, Se, As, Te or Ge.

As used herein, the term "hetero atom" will be understood to mean an atom in an organic compound that is not a H- or C-atom, and preferably will be understood to mean B, N, O, S, P, Si, Se, As, Te or Ge.

A carbyl or hydrocarbyl group comprising a chain of 3 or more C atoms may be straight-chain, branched and/or cyclic, and may include spiro-connected and/or fused rings.

Preferred carbyl and hydrocarbyl groups include alkyl, alkoxy, alkylcarbonyl, alkoxycarbonyl, alkylcarbonyloxy and alkoxycarbonyloxy, each of which is optionally substituted and has 1 to 40, preferably 1 to 25, very preferably 1 to 18 C atoms, furthermore optionally substituted aryl or aryloxy having 6 to 40, preferably 6 to 25 C atoms, furthermore alkylaryloxy, arylcarbonyl, aryloxycarbonyl, arylcarbonyloxy and aryloxycarbonyloxy, each of which is optionally substituted and has 6 to 40, preferably 7 to 40 C atoms, wherein all these groups do optionally contain one or more hetero atoms, preferably selected from B, N, O, S, P, Si, Se, As, Te and Ge.

Further preferred carbyl and hydrocarbyl group include for example: a $C_1$-$C_{40}$ alkyl group, a $C_1$-$C_{40}$ fluoroalkyl group, a $C_1$-$C_{40}$ alkoxy or oxaalkyl group, a $C_2$-$C_{40}$ alkenyl group, a $C_2$-$C_{40}$ alkynyl group, a $C_3$-$C_{40}$ allyl group, a $C_4$-$C_{40}$ alkyldienyl group, a $C_4$-$C_{40}$ polyenyl group, a $C_2$-$C_{40}$ ketone group, a $C_2$-$C_{40}$ ester group, a $C_6$-$C_{18}$ aryl group, a $C_6$-$C_{40}$ alkylaryl group, a $C_6$-$C_{40}$ arylalkyl group, a $C_4$-$C_{40}$ cycloalkyl group, a $C_4$-$C_{40}$ cycloalkenyl group, and the like. Preferred among the foregoing groups are a $C_1$-$C_{20}$ alkyl group, a $C_1$-$C_{20}$ fluoroalkyl group, a $C_2$-$C_{20}$ alkenyl group, a $C_2$-$C_{20}$ alkynyl group, a $C_3$-$C_{20}$ allyl group, a $C_4$-$C_{20}$ alkyldienyl group, a $C_2$-$C_{20}$ ketone group, a $C_2$-$C_{20}$ ester group, a $C_6$-$C_{12}$ aryl group, and a $C_4$-$C_{20}$ polyenyl group, respectively.

Also included are combinations of groups having carbon atoms and groups having hetero atoms, like e.g. an alkynyl group, preferably ethynyl, that is substituted with a silyl group, preferably a trialkylsilyl group.

The carbyl or hydrocarbyl group may be an acyclic group or a cyclic group. Where the carbyl or hydrocarbyl group is an acyclic group, it may be straight-chain or branched. Where the carbyl or hydrocarbyl group is a cyclic group, it may be a non-aromatic carbocyclic or heterocyclic group, or an aryl or heteroaryl group.

A non-aromatic carbocyclic group as referred to above and below is saturated or unsaturated and preferably has 4 to 30 ring C atoms. A non-aromatic heterocyclic group as referred to above and below preferably has 4 to 30 ring C atoms, wherein one or more of the C ring atoms are optionally replaced by a hetero atom, preferably selected from N, O, S, Si and Se, or by a —S(O)— or —S(O)$_2$— group. The non-aromatic carbo- and heterocyclic groups are mono- or polycyclic, may also contain fused rings, preferably contain 1, 2, 3 or 4 fused or unfused rings, and are optionally substituted with one or more groups L, wherein L is selected from halogen, —CN, —NC, —NCO, —NCS, —OCN, —SCN, —C(=O)NR°R°°, —C(=O)X°, —C(=O)R°, —NH$_2$, —NR°R°°, —SH, —SR°, —SO$_3$H, —SO$_2$R°, —OH, —NO$_2$, —CF$_3$, —SF$_5$, optionally substituted silyl, or carbyl or hydrocarbyl with 1 to 40 C atoms that is optionally substituted and optionally comprises one or more hetero atoms, and is preferably alkyl, alkoxy, thioalkyl, alkylcarbonyl, alkoxycarbonyl or alkoxycarbonyloxy with 1 to 20 C atoms that is optionally fluorinated, X° is halogen, preferably F, Cl or Br, and R°, R°° have the meanings given above and below, and preferably denote H or alkyl with 1 to 12 C atoms.

Preferred substituents L are selected from halogen, most preferably F, or alkyl, alkoxy, oxaalkyl, thioalkyl, fluoroalkyl and fluoroalkoxy with 1 to 12 C atoms, or alkenyl or alkynyl with 2 to 12 C atoms.

Preferred non-aromatic carbocyclic or heterocyclic groups are tetrahydrofuran, indane, pyran, pyrrolidine, piperidine, cyclopentane, cyclohexane, cycloheptane, cyclopentanone, cyclohexanone, dihydro-furan-2-one, tetrahydro-pyran-2-one and oxepan-2-one.

An aryl group as referred to above and below preferably has 4 to 30 ring C atoms, is mono- or polycyclic and may also contain fused rings, preferably contains 1, 2, 3 or 4 fused or unfused rings, and is optionally substituted with one or more groups L as defined above.

A heteroaryl group as referred to above and below preferably has 4 to 30 ring C atoms, wherein one or more of the C ring atoms are replaced by a hetero atom, preferably selected from N, O, S, Si and Se, is mono- or polycyclic and may also contain fused rings, preferably contains 1, 2, 3 or 4 fused or unfused rings, and is optionally substituted with one or more groups L as defined above.

As used herein, "arylene" will be understood to mean a divalent aryl group, and "heteroarylene" will be understood to mean a divalent heteroaryl group, including all preferred meanings of aryl and heteroaryl as given above and below.

Preferred aryl and heteroaryl groups are phenyl in which, in addition, one or more CH groups may be replaced by N, naphthalene, thiophene, selenophene, thienothiophene, dithienothiophene, fluorene and oxazole, all of which can be unsubstituted, mono- or polysubstituted with L as defined above. Very preferred rings are selected from pyrrole, preferably N-pyrrole, furan, pyridine, preferably 2- or 3-pyridine, pyrimidine, pyridazine, pyrazine, triazole, tetrazole, pyrazole, imidazole, isothiazole, thiazole, thiadiazole, isoxazole, oxazole, oxadiazole, thiophene, preferably 2-thiophene, selenophene, preferably 2-selenophene, thieno[3,2-b]thiophene, thieno[2,3-b]thiophene, furo[3,2-b]furan, furo[2,3-b]furan, seleno[3,2-b]selenophene, seleno[2,3-b]selenophene, thieno[3,2-b]selenophene, thieno[3,2-b]furan, indole, isoindole, benzo[b]furan, benzo[b]thiophene, benzo[1,2-b;4,5-b']dithiophene, benzo[2,1-b;3,4-b']dithiophene, quinole, 2-methylquinole, isoquinole, quinoxaline, quinazoline, benzotriazole, benzimidazole, benzothiazole, benzisothiazole, benzisoxazole, benzoxadiazole, benzoxazole, benzothiadiazole, 4H-cyclopenta[2,1-b;3,4-b']dithiophene, 7H-3,4-dithia-7-sila-cyclopenta[a]pentalene, all of which can be unsubstituted, mono- or polysubstituted with L as defined above. Further examples of aryl and heteroaryl groups are those selected from the groups shown hereinafter.

An alkyl group or an alkoxy group, i.e., where the terminal $CH_2$ group is replaced by —O—, can be straight-chain or branched. It is preferably straight-chain, has 2, 3, 4, 5, 6, 7, 8, 12 or 16 carbon atoms and accordingly is preferably ethyl, propyl, butyl, pentyl, hexyl, heptyl, octyl, dodecyl or hexadecyl, ethoxy, propoxy, butoxy, pentoxy, hexoxy, heptoxy, octoxy, dodecoxy or hexadecoxy, furthermore methyl, nonyl, decyl, undecyl, tridecyl, tetradecyl, pentadecyl, nonoxy, decoxy, undecoxy, tridecoxy or tetradecoxy, for example.

An alkenyl group, i.e., wherein one or more $CH_2$ groups are replaced by —CH=CH— can be straight-chain or branched. It is preferably straight-chain, has 2 to 10 C atoms and accordingly is preferably vinyl, prop-1-, or prop-2-enyl, but-1-, 2- or but-3-enyl, pent-1-, 2-, 3- or pent-4-enyl, hex-1-, 2-, 3-, 4- or hex-5-enyl, hept-1-, 2-, 3-, 4-, 5- or hept-6-enyl, oct-1-, 2-, 3-, 4-, 5-, 6- or oct-7-enyl, non-1-, 2-, 3-, 4-, 5-, 6-, 7- or non-8-enyl, dec-1-, 2-, 3-, 4-, 5-, 6-, 7-, 8- or dec-9-enyl.

Especially preferred alkenyl groups are $C_2$-$C_7$-1E-alkenyl, $C_4$-$C_7$-3E-alkenyl, $C_5$-$C_7$-4-alkenyl, $C_6$-$C_7$-5-alkenyl and $C_7$-6-alkenyl, in particular $C_2$-$C_7$-1E-alkenyl, $C_4$-$C_7$-3E-alkenyl and $C_5$-$C_7$-4-alkenyl. Examples for particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 C atoms are generally preferred.

An oxaalkyl group, i.e., where one $CH_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example.

In an alkyl group wherein one $CH_2$ group is replaced by —O— and one $CH_2$ group is replaced by —C(O)—, these radicals are preferably neighbored. Accordingly these radicals together form a carbonyloxy group —C(O)—O— or an oxycarbonyl group —O—C(O)—. Preferably this group is straight-chain and has 2 to 6 C atoms. It is accordingly preferably acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl, 4-(methoxycarbonyl)-butyl.

An alkyl group wherein two or more $CH_2$ groups are replaced by —O— and/or —C(O)O— can be straight-chain or branched. It is preferably straight-chain and has 3 to 12 C atoms. Accordingly it is preferably bis-carboxy-methyl, 2,2-bis-carboxy-ethyl, 3,3-bis-carboxy-propyl, 4,4-bis-carboxy-butyl, 5,5-bis-carboxy-pentyl, 6,6-bis-carboxy-hexyl, 7,7-bis-carboxy-heptyl, 8,8-bis-carboxy-octyl, 9,9-bis-carboxy-nonyl, 10,10-bis-carboxy-decyl, bis-(methoxycarbonyl)-methyl, 2,2-bis-(methoxycarbonyl)-ethyl, 3,3-bis-(methoxycarbonyl)-propyl, 4,4-bis-(methoxycarbonyl)-butyl, 5,5-bis-(methoxycarbonyl)-pentyl, 6,6-bis-(methoxycarbonyl)-hexyl, 7,7-bis-(methoxycarbonyl)-heptyl, 8,8-bis-(methoxycarbonyl)-octyl, bis-(ethoxycarbonyl)-methyl, 2,2-bis-(ethoxycarbonyl)-ethyl, 3,3-bis-(ethoxycarbonyl)-propyl, 4,4-bis-(ethoxycarbonyl)-butyl, 5,5-bis-(ethoxycarbonyl)-hexyl.

A thioalkyl group, i.e., where one $CH_2$ group is replaced by —S—, is preferably straight-chain thiomethyl (=—$SCH_3$), 1-thioethyl (—$SCH_2CH_3$), 1-thiopropyl (=—$SCH_2CH_2CH_3$), 1-(thiobutyl), 1-(thiopentyl), 1-(thiohexyl), 1-(thioheptyl), 1-(thiooctyl), 1-(thiononyl), 1-(thiodecyl), 1-(thioundecyl) or 1-(thiododecyl), wherein preferably the $CH_2$ group adjacent to the $sp^2$ hybridised vinyl carbon atom is replaced.

A fluoroalkyl group is perfluoroalkyl $C_iF_{2i+1}$, wherein i is an integer from 1 to 15, in particular $CF_3$, $C_2F_5$, $C_3F_7$, $C_4F_9$, $C_5F_{11}$, $C_6F_{13}$, $C_7F_{15}$ or $C_8F_{17}$, very preferably $C_6F_{13}$, or partially fluorinated alkyl, preferably with 1 to 15 C atoms, in particular 1,1-difluoroalkyl, all of the aforementioned being straight-chain or branched.

Preferably "fluoroalkyl" means a partially fluorinated (i.e. not perfluorinated) alkyl group.

Alkyl, alkoxy, alkenyl, oxaalkyl, thioalkyl, carbonyl and carbonyloxy groups can be achiral or chiral groups. Particularly preferred chiral groups are 2-butyl (=1-methylpropyl), 2-methylbutyl, 2-methylpentyl, 3-methylpentyl, 2-ethylhexyl, 2-butyloctyl, 2-hexyldecyl, 2-octyldodecyl, 2-propylpentyl, in particular 2-methylbutyl, 2-methylbutoxy, 2-methylpentoxy, 3-methylpentoxy, 2-ethyl-hexoxy, 2-butyloctoxyo, 2-hexyldecoxy, 2-octyldodecoxy, 1-methylhexoxy, 2-octyloxy, 2-oxa-3-methylbutyl, 3-oxa-4-methylpentyl, 4-methylhexyl, 2-hexyl, 2-octyl, 2-nonyl, 2-decyl, 2-dodecyl, 6-methoxy-octoxy, 6-methyloctoxy, 6-methyloctanoyloxy, 5-methylheptyloxy-carbonyl, 2-methylbutyryloxy, 3-methylvaleroyloxy, 4-methylhexanoyloxy, 2-chloropropionyloxy, 2-chloro-3-methylbutyryloxy, 2-chloro-4-methyl-valeryl-oxy, 2-chloro-3-methylvaleryloxy, 2-methyl-3-oxapentyl, 2-methyl-3-oxa-hexyl, 1-methoxypropyl-2-oxy, 1-ethoxypropyl-2-oxy, 1-propoxypropyl-2-oxy, 1-butoxypropyl-2-oxy, 2-fluorooctyloxy, 2-fluorodecyloxy, 1,1,1-trifluoro-2-octyloxy, 1,1,1-trifluoro-2-octyl, 2-fluoromethyloctyloxy for example. Very preferred are 2-ethylhexyl, 2-butyloctyl, 2-hexyldecyl, 2-octyldodecyl, 2-hexyl, 2-octyl, 2-octyloxy, 1,1,1-trifluoro-2-hexyl, 1,1,1-trifluoro-2-octyl and 1,1,1-trifluoro-2-octyloxy.

Preferred achiral branched groups are isopropyl, isobutyl (=methylpropyl), isopentyl (=3-methylbutyl), tert. butyl, isopropoxy, 2-methyl-propoxy and 3-methylbutoxy.

In a preferred embodiment, the alkyl groups are independently of each other selected from primary, secondary or tertiary alkyl or alkoxy with 1 to 30 C atoms, wherein one or more H atoms are optionally replaced by F, or aryl, aryloxy, heteroaryl or heteroaryloxy that is optionally alkylated or alkoxylated and has 4 to 30 ring atoms. Very preferred groups of this type are selected from the group consisting of the following formulae

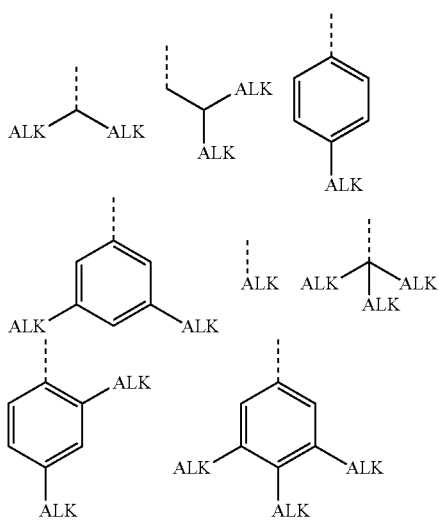

wherein "ALK" denotes optionally fluorinated, preferably linear, alkyl or alkoxy with 1 to 20, preferably 1 to 12 C-atoms, in case of tertiary groups very preferably 1 to 9 C atoms, and the dashed line denotes the link to the ring to which these groups are attached. Especially preferred among these groups are those wherein all ALK subgroups are identical.

As used herein, "halogen" or "hal" includes F, Cl, Br or I, preferably F, Cl or Br.

As used herein, —CO—, —C(=O)— and —C(O)— will be understood to mean a carbonyl group, i.e. a group having the structure

As used herein, C=CR$^1$R$^2$ will be understood to mean an ylidene group, i.e. a group having the structure

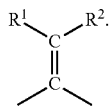

Above and below, Y$^1$ and Y$^2$ are independently of each other H, F, Cl or CN.

Above and below, R$^0$ and R$^{00}$ are independently of each other H or an optionally substituted carbyl or hydrocarbyl group with 1 to 40 C atoms, and preferably denote H or alkyl with 1 to 12 C-atoms.

DETAILED DESCRIPTION

The compounds of formula I are easy to synthesize, especially by methods suitable for mass production, and exhibit advantageous properties, for example good structural organization and film-forming properties, good electronic properties, especially high charge carrier mobility, good processability, especially high solubility in organic solvents, and high light and thermal stability.

The compounds of formula I are especially suitable as electron acceptor or n-type semiconductor, especially in semiconducting materials containing both donor and acceptor components, and for the preparation of a mixture of p-type and n-type semiconductors which are suitable for use in BHJ OPV devices and OPD devices.

For OPV and OPD application, the compounds of formula I, or a mixture comprising two or more fullerene derivatives, one or more of which are selected from formula I, is blended with a further p-type semiconductor such as a polymer, an oligomer or a defined molecular unit to form the active layer in the OPV/OPD device (also referred to as "photoactive layer").

The OPV/OPD device is usually further composed of a first, transparent or semi-transparent electrode, typically provided on a transparent or semi-transparent substrate, on one side of the active layer, and a second metallic or semi-transparent electrode on the other side of the active layer. Additional interfacial layer(s) acting as hole blocking layer, hole transporting layer, electron blocking layer and/or electron transporting layer, typically comprising a metal oxide (for example, ZnO$_x$, TiO$_x$, ZTO, MoO$_x$, NiO$_x$), a salt (example: LiF, NaF), a conjugated polymer electrolyte (for example: PEDOT:PSS or PFN), a conjugated polymer (for example: PTAA) or an organic compound (for example: NPB, Alq$_3$, TPD), can be inserted between the active layer and an electrode.

The compounds of formula I demonstrate the following improved properties compared to previously disclosed fullerene derivatives for OPV/OPD application:
i) Electron accepting and/or donating unit(s) in position R$^1$ to R$^4$ reduce the fullerene band-gap and therefore the potential for improved light absorption.
ii) Additional fine-tuning of the electronic energies (HOMO/LUMO levels) by careful selection of electron accepting and/or donating unit(s) in position R$^1$ to R$^4$ increases the open circuit potential (V$_{oc}$).
iii) Additional fine-tuning of the electronic energies (HOMO/LUMO levels) by careful selection of electron accepting and/or donating unit(s) in position R$^1$ to R$^4$ reduces the energy loss in the electron transfer process between the fullerene derivative and a p-type material (for example a polymer, oligomer or defined molecular unit) when used in the active layer of an OPV or OPD device.
iv) Substitution in one or more of the positions R$^1$ to R$^4$, which can each possess more than one solubilising group enable higher fullerene solubility especially in non-halogenated solvents due to the increased number of solubilising groups.
v) Substitution in one or more of the positions R$^1$ to R$^4$, which can each possess more than one solubilising group, enable greater light stability of the bulk heterojunction through mediation of the fullerene 2+2 Diels Alder dimerisation reaction.

vi) Substitution in one or more of the positions $R^1$ to $R^4$, which can each possess more than one solubilising group, enable greater thermal stability of the bulk heterojunction through mediation of the fullerene crystallisation and/or phase separation kinetic, thus stabilising the initial equilibrium thermodynamics in the BHJ.

vii) Substitution in one or more of the positions $R^1$ to $R^4$, may create a mixture of enantiomers and/or diastereomers thus reducing the free energy of crystallisation of the compound, enabling greater thermal stability of the bulk heterojunction through mediation of the fullerene crystallisation and/or phase separation kinetic, thus stabilising the initial equilibrium thermodynamics in the BHJ.

viii) Substitution in one or more of the positions $R^1$ to $R^4$, may create a mixture of enantiomers and/or diastereomers thus increase the free energy of dissolution of the compound, enabling higher fullerene solubility especially in non-halogenated solvents due to increase entropy of mixing.

In the compounds of formula I and its subformulae, o preferably denotes 1, 2, 3 or, 4, very preferably 1 or 2.

The fullerene $C_n$ in formula I and its subformulae may be composed of any number n of carbon atoms Preferably, in the compounds of formula I and its subformulae the number of carbon atoms n of which the fullerene $C_n$ is composed is 60, 70, 76, 78, 82, 84, 90, 94 or 96, very preferably 60 or 70.

The fullerene $C_n$ in formula I and its subformulae is preferably selected from carbon based fullerenes, endohedral fullerenes, or mixtures thereof, very preferably from carbon based fullerenes.

Suitable and preferred carbon based fullerenes include, without limitation, $(C_{60-Ih})[5,6]$fullerene, $(C_{70-D5h})[5,6]$fullerene, $(C_{76-D2*})[5,6]$fullerene, $(C_{84-D2*})[5,6]$fullerene, $(C_{84-D2d})[5,6]$fullerene, or a mixture of two or more of the aforementioned carbon based fullerenes.

The endohedral fullerenes are preferably metallofullerenes. Suitable and preferred metallofullerenes include, without limitation, La@$C_{60}$, La@$C_{82}$, Y@$C_{82}$, Sc$_3$N@$C_{80}$, Y$_3$N@$C_{80}$, Sc$_3$C$_2$@$C_{80}$ or a mixture of two or more of the aforementioned metallofullerenes.

Preferably the fullerene $C_n$ is substituted at a [6,6] and/or [5,6] bond, preferably substituted on at least one [6,6] bond.

In addition to the cyclohexadiene ring shown in formula I, the fullerene $C_n$ may have any number (m) of secondary adducts appended, named "Adduct" in formula I. The secondary adduct may be any possible adduct or combination of adducts with any connectivity to the fullerene.

In the compounds of formula I and its subformulae, all adducts may be connected to one another in any combination in the finished product or during synthesis, to facilitate preferred properties in the finished product.

In the compounds of formula I and its subformulae, the number m of secondary adducts appended to the fullerene $C_n$ is 0, an integer≥1, or a non-integer>0 like 0.5 or 1.5, and is preferably 0, 1 or 2.

In a preferred embodiment the number m of the secondary adducts appended to the fullerene $C_n$ is 0.

In another preferred embodiment the number m of the secondary adducts appended to the fullerene $C_n$ is>0, preferably 1 or 2.

The secondary adduct, named "Adduct" in formula I and its subformulae, is preferably selected from the following formulae

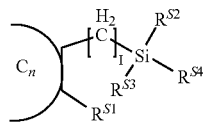 S-1

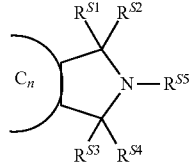 S-2

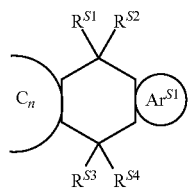 S-3

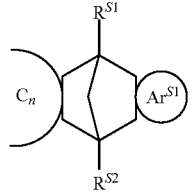 S-4

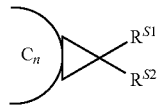 S-5

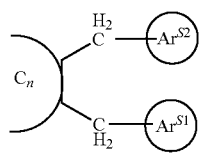 S-6

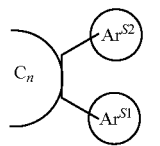 S-7

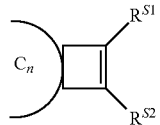 S-8

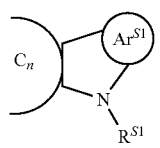 S-9

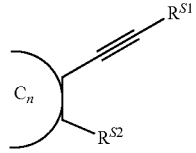 S-10

-continued

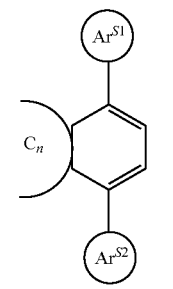
S-11

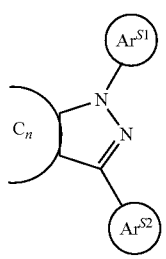
S-12

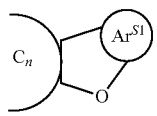
S-13

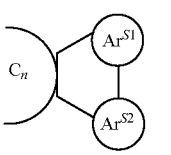
S-14

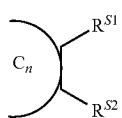
S-15

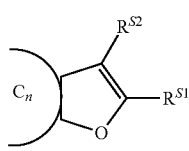
S-16

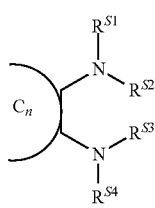
S-17

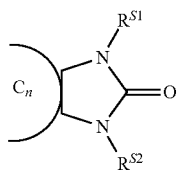
S-18

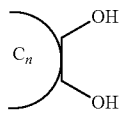
S-19

-continued

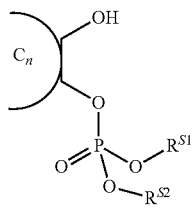
S-20

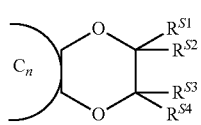
S-21

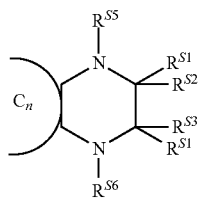
S-22 wherein $R^{S1}$, $R^{S2}$, $R^{S3}$, $R^{S4}$, $R^{S5}$ and $R^{S6}$ independently of each other denote H, halogen or CN, or have one of the meanings of $R^5$ or $R^6$ as given in formula I, and $Ar^{S2}$ has one of the meanings of $Ar^{S1}$ in formula I or its preferred meanings as given above and below.

$Ar^{S1}$ in formula I is preferably an aryl or heteroaryl group with 5 to 20, preferably 5 to 15, ring atoms, which is mono- or polycyclic, and which is preferably substituted by one or more, preferably two or more, identical or different substituents $R^5$ or $R^6$ that are different from H and are preferably selected from halogen, very preferably F, straight-chain, branched or cyclic alkyl with 1 to 30, preferably 4 to 20, very preferably 5 to 15, C atoms, in which one or more $CH_2$ groups are optionally replaced by —O—, —S—, —C(O)—, —C(S)—, —C(O)—O—, —O—C(O)—, —S(O)$_2$—, —NR$^0$—, —SiR$^0$R$^{00}$—, —CF$_2$—, wherein R$^0$ and R$^{00}$ have one of the meanings given above and below.

Preferably $Ar^{S1}$ is selected from the following groups

(F-C-1)

(F-C-2)

(F-C-3)

(F-C-4)

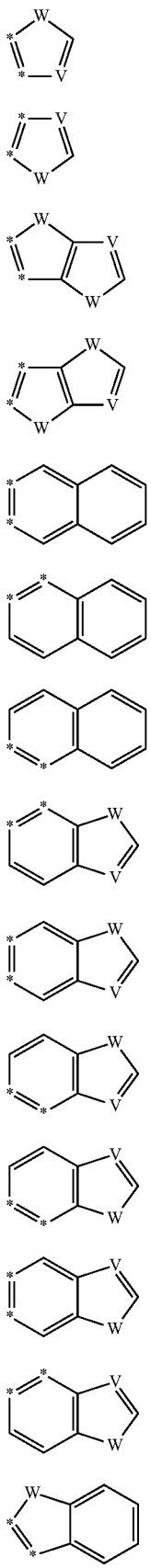
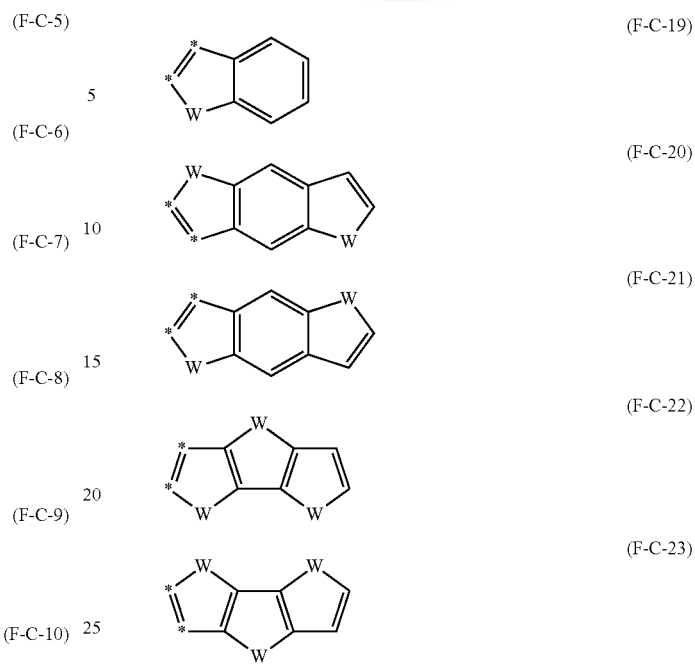
which are optionally substituted by one or more groups $R^5$, and wherein V is CH or N, and W is independently selected from the group consisting of S, O and Se.
More preferably $Ar^{S1}$ is selected from the following groups
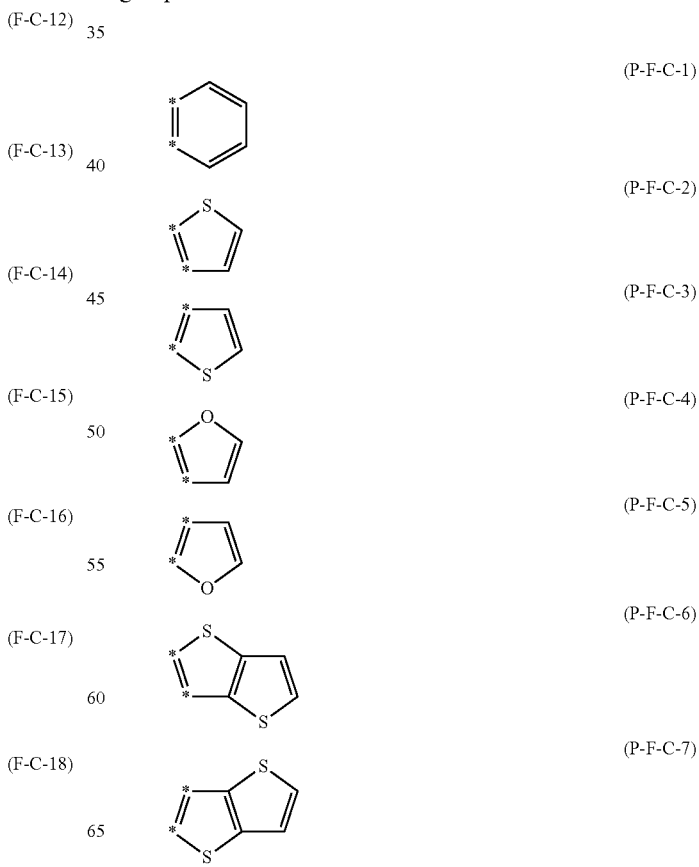

-continued (P-F-C-8)

(P-F-C-9)

(P-F-C-10)

which are optionally substituted by one or more groups $R^5$.

Very preferably $Ar^{S1}$ denotes a benzene or naphthalene ring that is optionally substituted by one or more groups $R^5$.

Preferred substituents $R^1$, $R^2$, $R^3$ and $R^4$ in the compounds of formula I are independently of each other selected from alkyl, alkoxy and alkylcarbonyloxy with 1 to 30, preferably 4 to 20 C atoms, in which one or more $CH_2$ groups are optionally replaced by —O—, —S—, —C(O)—, —C(S)—, —C(O)—O—, —O—C(O)—, —SiR°R°°—, —CF$_2$—, —CHF—, —CCl$_2$—, furthermore aryloxy, arylcarbonyloxy, heteroaryloxy and heteroarylcarbonyloxy with 5 to 15 ring atoms which are optionally substituted by one or more groups $R^5$ as defined above and below.

Preferred substituents $R^1$, $R^2$, $R^3$ and $R^4$ in the compounds of formula I are selected from the following formulae (P-RS-1)

(P-RS-2)

(P-RS-3)

(P-RS-4)

(P-RS-5)

(P-RS-6)

(P-RS-7)

wherein
$Ar^{S2}$ denotes $R^7$ or has one of the meanings of $Ar^{S1}$ as given above and below,
i is 0 or an integer from 1 to 9, preferably 0 or an integer from 1 to 2,
k is 0 or an integer from 1 to 9, preferably 0 or an integer from 1 to 5.

Preferred compounds of formula I are those wherein $R^3$ and $R^4$ are H.

Further preferred compounds of formula I are those wherein one of $R^1$ and $R^2$ is H and the other is different from H.

Very preferred compounds formula I are those wherein $R^2$, $R^3$ and $R^4$ are H and $R^1$ is different from H, and is preferably selected from formulae P-RS-1 to P-RS-7 above, and preferably n is 60.

Further preferred compounds formula I are those wherein $R^2$, $R^3$ and $R^4$ are H and $R^1$ is selected from formulae P-RS-1 to P-RS-7 above, very preferably from formula P-RS-1 or P-RS-7, in particular wherein k is 0, and n is 60.

Preferably $R^5$ and $R^6$ in the compounds of formula I and its subformulae denote straight-chain, branched or cyclic alkyl with 1 to 30, preferably 4 to 30, very preferably 4 to 20 C atoms, in which one or more $CH_2$ groups are optionally replaced by —O—, —S—, —C(O)—, —C(S)—, —C(O)—O—, —O—C(O)—, —NR°—, —SiR°R°°—, —CF$_2$—, and wherein one or more H atoms are replaced by fluorine atoms, wherein R° and R°° have one of the meanings given above and below.

Preferably $R^7$ in the compounds of formula I denotes a carbocyclic or heterocyclic group selected from the following formulae

C-1

C-2

C-3

C-4

C-5

C-6

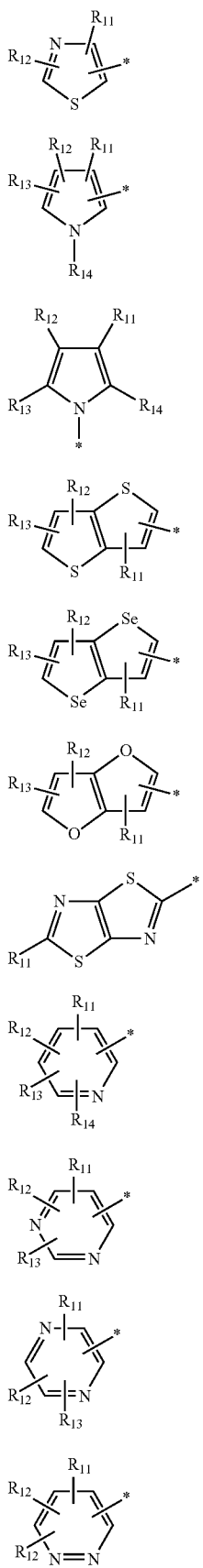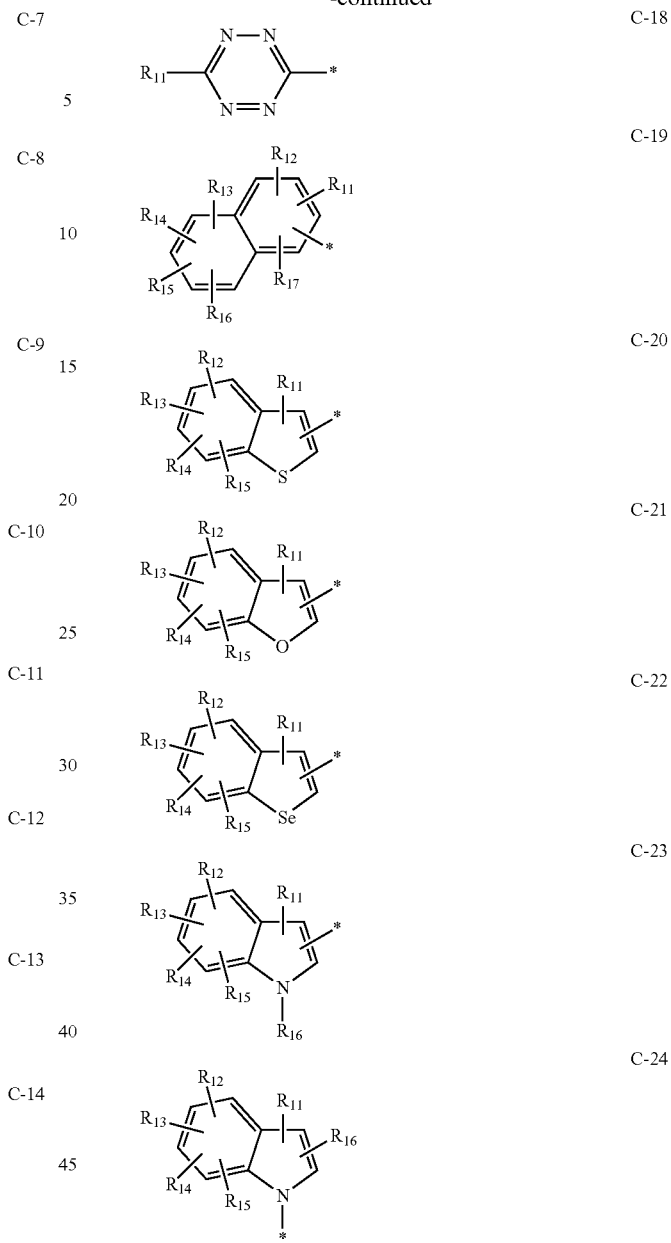

wherein $R^0$ and $R^{00}$ are as defined above and below, $R^{000}$ has one of the meanings of $R^{00}$ different from H, $R^{11}$, $R^{12}$, $R^{13}$, $R^{14}$, $R^{15}$, $R^{16}$, $R^{17}$ and $R^{18}$ independently of each other denote H, halogen or CN or have one of the meanings of $R^8$ or its preferred meanings as given above, and wherein in formula C-1 at least one of $R^{11}$, $R^{12}$, $R^{13}$, $R^{14}$ and $R^{15}$ is different from H and in formula C-4 at least one of $R^{11}$, $R^{12}$ and $R^{13}$ is different from H. Preferably in each of the aforementioned formulae at least one substituent $R^{11}$, $R^{12}$, $R^{13}$, $R^{14}$, $R^{15}$, $R^{16}$, $R^{17}$ or $R^{18}$ is different from H.

In formulae C-4, C-5, C-6 and C-7 the linkage to the adjacent group is preferably located in 2-position (relative to the hetero atom), and the substituent $R^{13}$ in 5-position is preferably different from H.

In formulae C-10, C-11 and C-12 the linkage to the adjacent group is preferably located in 2-position (relative to the hetero atom), and the substituent $R^{13}$ in 5-position is preferably different from H.

In formulae C-20, C-21 and C-22 the linkage to the adjacent group is preferably located in 2-position (relative to the hetero atom).

Very preferably $R^7$ denotes a carbocyclic or heterocyclic group selected from the following formulae

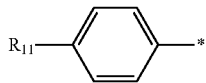
S-C-1

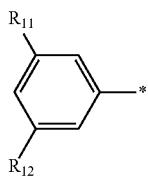
S-C-2

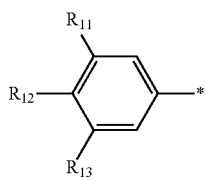
S-C-3

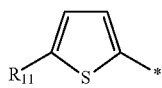
S-C-4

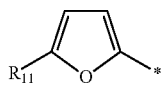
S-C-5

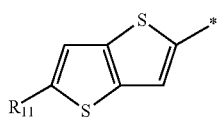
S-C-6

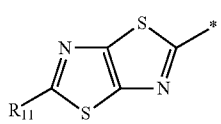
S-C-7

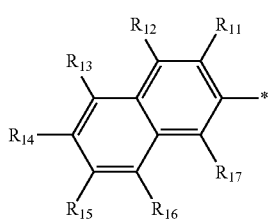
S-C-8

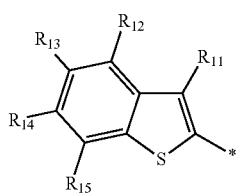
S-C-9

-continued

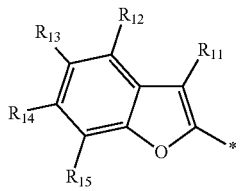
S-C-10 wherein $R^0$ and $R^{00}$ are as defined above and below, $R^{000}$ has one of the meanings of $R^{00}$ different from H, $R^{11}$, $R^{12}$, $R^{13}$, $R^{14}$, $R^{15}$, $R^{16}$, $R^{17}$ and $R^{18}$, independently of each other denote H, halogen or CN or have one of the meanings of $R^8$ or its preferred meanings as given above. Preferably in each of the aforementioned formulae at least one substituent $R^{11}$, $R^{12}$, $R^{13}$, $R^{14}$, $R^{15}$, $R^{16}$, $R^{17}$ or $R^{18}$ is different from H.

Preferably $R^8$ in the compounds of formula I denotes straight-chain, branched or cyclic alkyl with 1 to 30, preferably 4 to 30, very preferably 4 to 20 C atoms, in which one or more $CH_2$ groups are optionally replaced by —O—, —S—, —C(O)—, —C(S)—, —C(O)—O—, —O—C(O)—, —$NR^0$—, —$SiR^0R^{00}$—, —$CF_2$—, and wherein one or more H atoms are replaced by fluorine atoms, wherein $R^0$ and $R^{00}$ have one of the meanings given above and below.

Very preferred groups $R^8$ are selected from alkyl, fluoroalkyl, alkoxy and thioalkyl having 1 to 30, preferably 4 to 30, very preferably 4 to 20, most preferably 5 to 15 C atoms.

In another preferred embodiment in the compounds of formula I and its subformulae one or more of $R^1$ to $R^6$ denotes $R^9$, wherein $R^9$ is a straight-chain, branched or cyclic alkyl group with 1 to 50, preferably 2 to 50, more preferably 2 to 25, most preferably 2 to 12, C atoms, in which one or more $CH_2$ or $CH_3$ groups are replaced by a cationic or anionic group.

The cationic group is preferably selected from the group consisting of phosphonium, sulfonium, ammonium, uronium, thiouronium, guanidinium or heterocyclic cations such as imidazolium, pyridinium, pyrrolidinium, triazolium, morpholinium or piperidinium cation.

Preferred cationic groups are selected from the group consisting of tetraalkylammonium, tetraalkylphosphonium, N-alkylpyridinium, N,N-dialkylpyrrolidinium, 1,3-dialkylimidazolium, wherein "alkyl" preferably denotes a straight-chain or branched alkyl group with 1 to 12 C atoms.

Further preferred cationic groups are selected from the group consisting of the following formulae

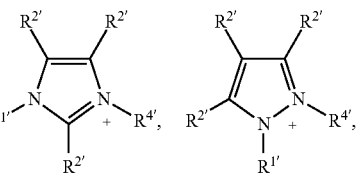

imidazolium     1H-pyrazolium

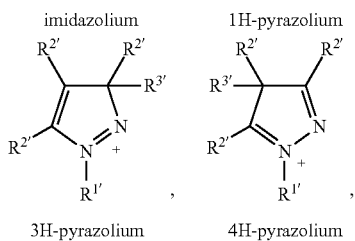

3H-pyrazolium     4H-pyrazolium

-continued
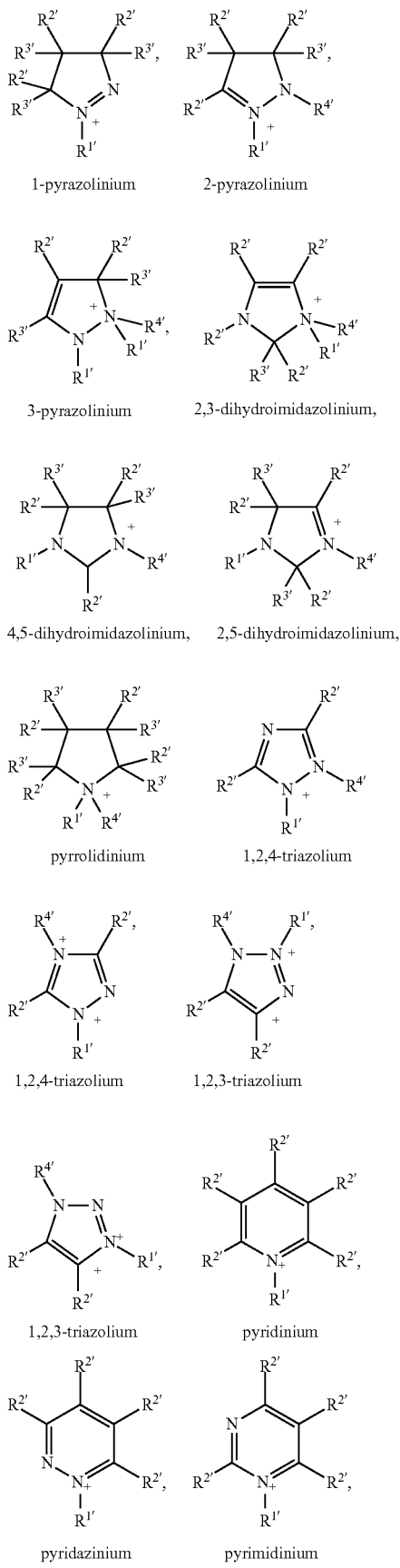
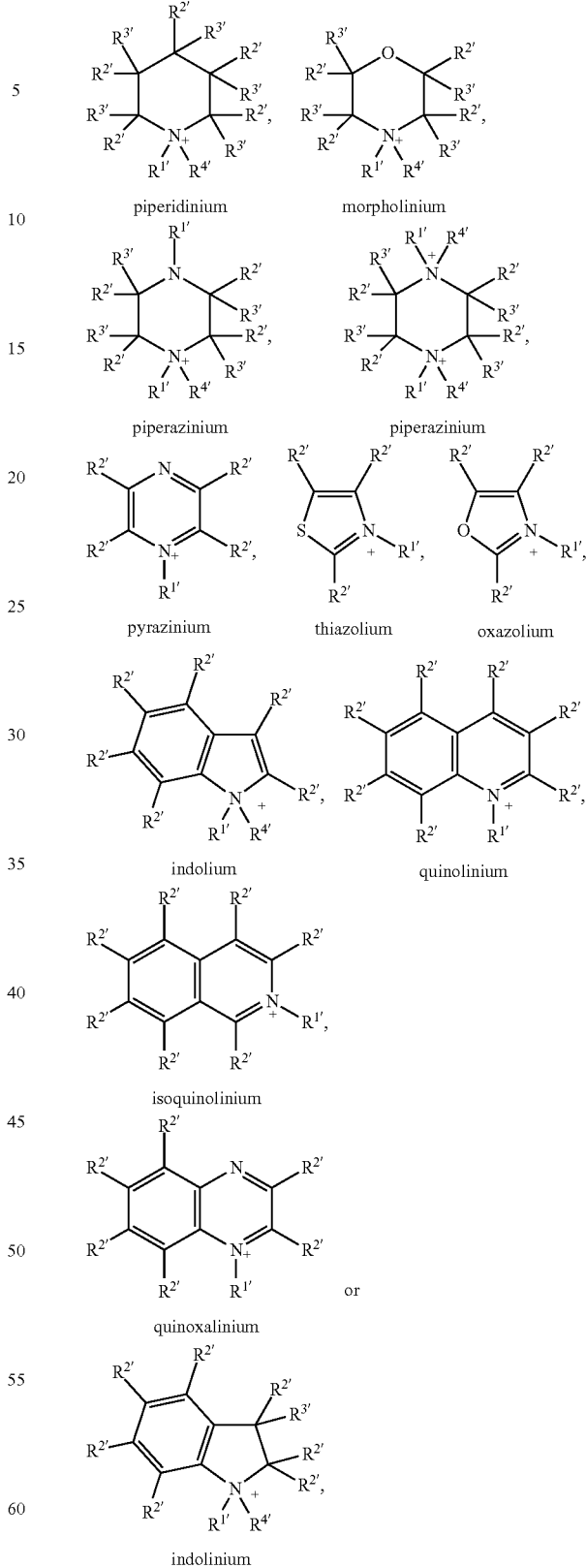
wherein $R^{1'}$, $R^{2'}$, $R^{3'}$ and $R^{4'}$ denote, independently of each other, H, a straight-chain or branched alkyl group with 1 to 12 C atoms or non-aromatic carbo- or heterocyclic group or an aryl or heteroaryl group, each of the aforementioned groups having 3 to 20, preferably 5 to 15, ring atoms, being mono- or polycyclic, and optionally being substituted by one or more identical or different substituents $R^8$ as defined above, or denote a link to the group $R^1$, $R^2$, $R^3$, $R^4$, $R^5$ or $R^6$, respectively.

In the above cationic groups of the above-mentioned formulae any one of the groups $R^{1'}$, $R^{2'}$, $R^{3'}$ and $R^{4'}$ (if they replace a $CH_3$ group) can denote a link to the respective group $R^1$, $R^2$, $R^3$, $R^4$, $R^5$ or $R^6$, or two neighbored groups $R^{1'}$, $R^{2'}$, $R^{3'}$ or $R^{4'}$ (if they replace a $CH_2$ group) can denote a link to the respective group $R^1$, $R^2$, $R^3$, $R^4$, $R^5$ or $R^6$.

The anionic group is preferably selected from the group consisting of borate, imide, phosphate, sulfonate, sulfate, succinate, naphthenate or carboxylate, very preferably from phosphate, sulfonate or carboxylate.

$R^0$ and $R^{00}$ preferably denote, independently of each other, H or alkyl with 1 to 12 C-atoms. $R^{000}$ preferably denotes alkyl with 1 to 12 C atoms.

Further preferred compounds of formula I are selected from the following preferred embodiments, including any combination thereof:
m is 0,
o is 1,
m is 0 and o is 1,
n is 60 or 70,
n is 60,
$Ar^{S1}$ denotes a benzene or naphthalene ring that is optionally substituted by one or more groups $R^5$,
$R^1$ and $R^2$ are selected from formulae P-RS-1 to P-RS-7, preferably from formula P-RS-1,
one of $R^1$ and $R^2$ is H and the other is different from H,
one of $R^1$ and $R^2$ is H and the other is selected from formulae P-RS-1 to P-RS-7, preferably from formula P-RS-1,
one or both of $R^1$ and $R^2$ are selected of formula P-RS-7,
one of $R^1$ and $R^2$ is H and the other is selected of formula P-RS-7,
k in formula P-RS-1 is 0,
k in formula P-RS-7 is 0,
$R^3$ and $R^4$ are H,
$R^8$ is selected from alkyl, fluoroalkyl, alkoxy, thioalkyl, —COO-alkyl and —CO-alkyl having 1 to 30, preferably 4 to 30, very preferably 4 to 20, most preferably 5 to 15 C atoms.

The compounds of formula I can be synthesized according to or in analogy to methods that are known to the skilled person and are described in the literature. The compounds of formula I is prepared from a 4+2 cycloaddition such as the Diels-Alder reaction using a substituted indene as precursors as described in scheme 1 and 2. In scheme 2, the indene precursors can be prepared, for example from a halogenated or a alkoxyl based reacting group. In some instance, the compounds of formula I can be obtained after further reaction on a fullerene intermediate as described scheme 3 using chemical group protection and deprotection strategies. Further synthesis methods can be taken from the examples.

Scheme 1. Synthesis of compounds of formula I from substituted indene using 4 + 2 cycloaddition. (LG = leaving group).

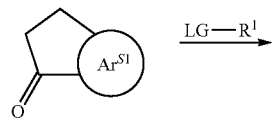

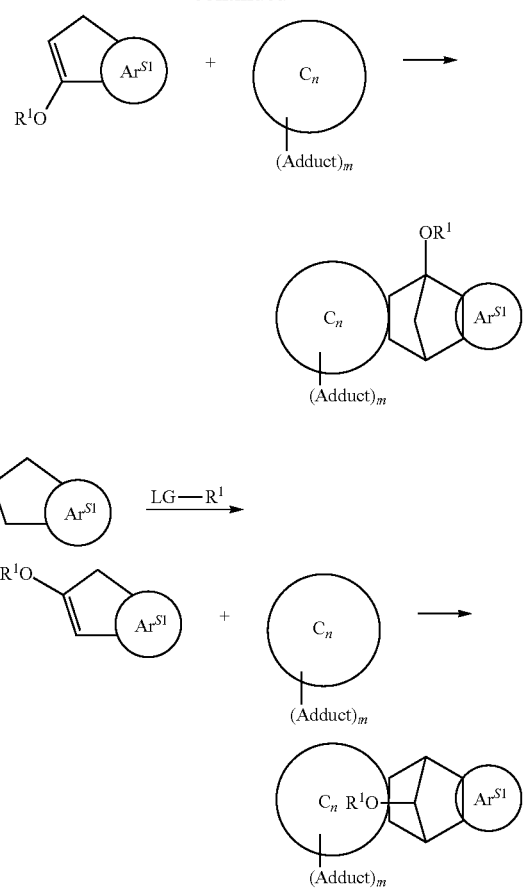

Scheme 2. Synthesis of compounds of formula I from substituted indene using 4 + 2 cycloaddition. (LG = leaving group, RG = reacting group, X = halogenure).

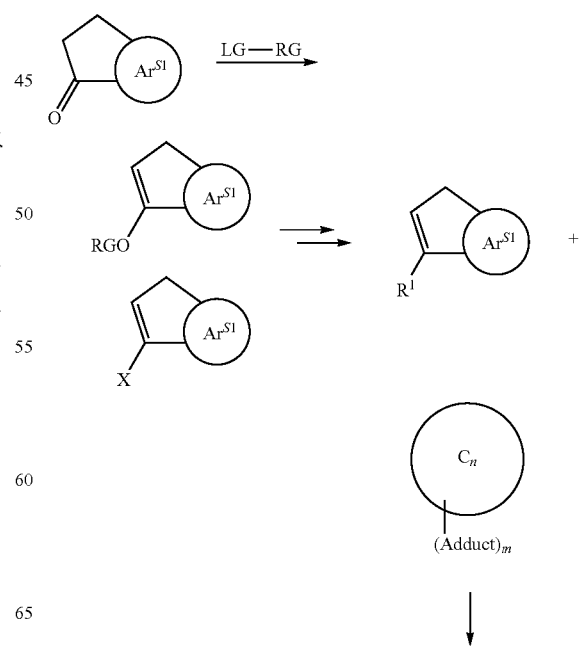

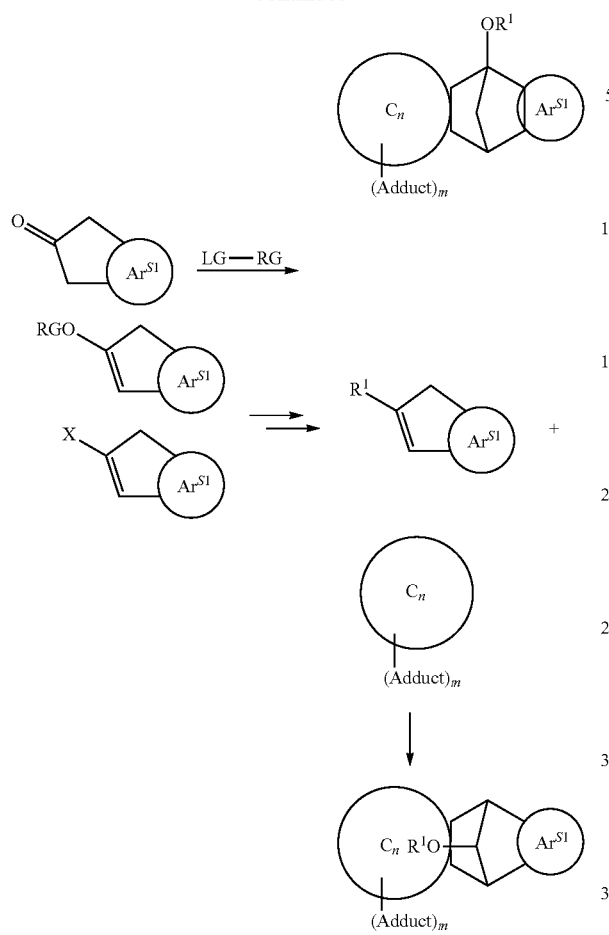

Scheme 3. Synthesis of compounds of formula I from substituted indene using 4 + 2 cycloaddition followed by further chemical reaction after the hydroxyl group deprotection. (LG = leaving group; PG = Protecting group).

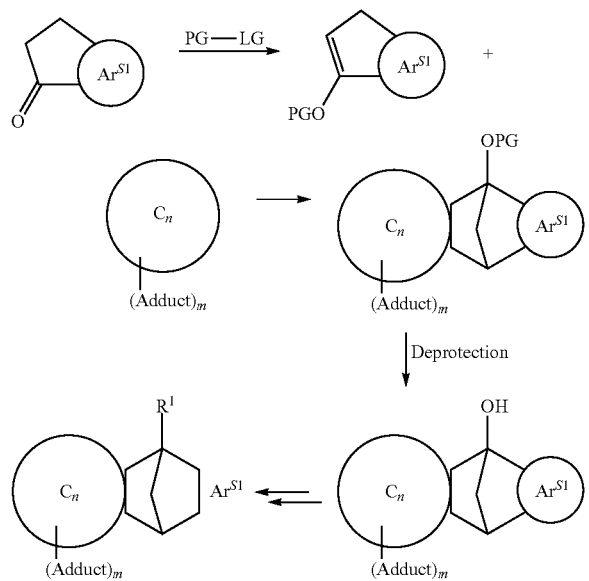

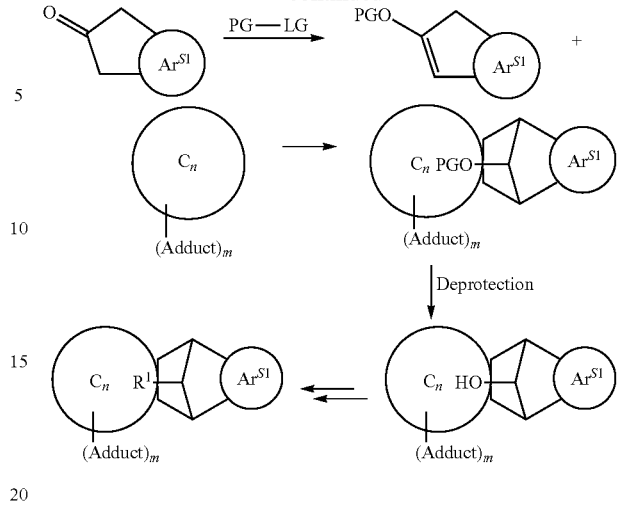

The novel methods of preparing fullerene derivatives as described above and below, and the intermediates used therein, are another aspect of the invention.

The compounds of formula I and its subformulae can also be used in mixtures, for example together with other monomeric compounds, or polymers, having one or more of a semiconducting, charge transport, hole transport, electron transport, hole blocking, electron blocking, electrically conducting, photoconducting and light emitting property Thus, another aspect of the invention relates to a composition (hereinafter referred to as "fullerene composition"), comprising one or more fullerene derivatives selected from formula I and its subformulae or from the preferred embodiments as described above and below (hereinafter simply referred to as "fullerene derivative of this invention"), and one or more additional compounds, preferably having one or more of a semiconducting, charge transport, hole transport, electron transport, hole blocking, electron blocking, electrically conducting, photoconducting and light emitting property.

In a preferred embodiment, the composition consists essentially of, or consists of, one or more components including the compounds of formula I and its subformulae.

The additional compounds in the fullerene composition can be selected for example from fullerene derivatives other than those of this invention, or from conjugated organic polymers.

A preferred embodiment of the present invention relates to a fullerene composition, comprising one or more fullerene derivatives, at least one of which is a fullerene derivative of this invention, and further comprising one or more conjugated organic polymers, which are preferably selected from electron donor, or p-type, semiconducting polymers.

Such a fullerene composition is especially suitable for use in the photoactive layer of an OPV or OPD device. Preferably the fullerene(s) and polymer(s) are selected such that the fullerene composition forms a bulk heterojunction (BHJ).

A suitable conjugated organic polymer (hereinafter simply referred to as "polymer") for use in a fullerene composition according to the present invention can be selected from polymers as described in prior art, for example in WO/2010/008672, WO/2010/049323, WO 2011/131280, WO/2011/052709, WO/2011/052710, US/2011/0017956, WO/2012/030942 or US/8334456B2.

A preferred polymer is selected from the group consisting of poly(3-substituted thiophene) and poly(3-substituted selenophene), for example poly(3-alkyl thiophene) or poly(3-alkyl selenophene), preferably poly(3-hexyl thiophene) or poly(3-hexyl selenophene).

A further preferred polymer comprises one or more repeating units selected from formulae PIIa and PIIb:

　　　　　　　　　　　　　　　　PIIa

　　　　　　　　　　　　　　　　PIIb wherein

Ac is arylene or heteroarylene with 5 to 30 ring atoms that is optionally substituted by one or more groups $R^S$, and preferably has electron acceptor property, D is arylene or heteroarylene with 5 to 30 ring atoms that is different from A, is optionally substituted by one or more groups $R^S$, and preferably has electron donor property, $Ar^1$, $Ar^2$, $Ar^3$ are, on each occurrence identically or differently, and independently of each other, arylene or heteroarylene that is different from A and D, preferably has 5 to 30 ring atoms, and is optionally substituted, preferably by one or more groups $R^P$, $R^P$ is on each occurrence identically or differently F, Br, Cl, —CN, —NC, —NCO, —NCS, —OCN, —SCN, —C(O)NR$^0$R$^{00}$, —C(O)X$^0$, —C(O)R$^0$, —C(O)OR$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, optionally substituted silyl, carbyl or hydrocarbyl with 1 to 40 C atoms that is optionally substituted and optionally comprises one or more hetero atoms, $R^0$ and $R^{00}$ are independently of each other H or optionally substituted $C_{1-40}$ carbyl or hydrocarbyl, and preferably denote H or alkyl with 1 to 12 C-atoms, $X^0$ is halogen, preferably F, Cl or Br, a, b, c are on each occurrence identically or differently 0, 1 or 2, d is on each occurrence identically or differently 0 or an integer from 1 to 10.

Preferably the polymer comprises at least one repeating unit of formula PIIa wherein b is at least 1. Further preferably the polymer comprises at least one repeating unit of formula PIIa wherein b is at least 1, and at least one repeating unit of formula PIIb wherein b is at least 1.

A further preferred polymer comprises, in addition to the units of formula PIIa and/or PIIb, one or more repeating units selected from monocyclic or polycyclic arylene or heteroarylene groups that are optionally substituted.

These additional repeating units are preferably selected of formula PIII

　　　　　　　　　　　　　　　　PIII wherein $Ar^1$, $Ar^2$, $Ar^3$, a, c and d are as defined in formula PIIa.

$R^P$ preferably denotes, on each occurrence identically or differently, H, straight-chain, branched or cyclic alkyl with 1 to 30 C atoms, in which one or more CH$_2$ groups are optionally replaced by —O—, —S—, —C(O)—, —C(S)—, —C(O)—O—, —O—C(O)—, —NR$^0$—, —SiR$^0$R$^{00}$—, —CF$_2$—, —CHR$^0$═CR$^{00}$—, —CY$^1$═CY$^2$— or —C≡C— in such a manner that O and/or S atoms are not linked directly to one another, and in which one or more H atoms are optionally replaced by F, Cl, Br, I or CN, or denotes aryl, heteroaryl, aryloxy or heteroaryloxy with 4 to 20 ring atoms which is optionally substituted, preferably by halogen or by one or more of the aforementioned alkyl or cyclic alkyl groups, wherein $R^0$ and $R^{00}$ and $Y^1$ and $Y^2$ have one of the meanings given above and below, $R^0$ and $R^{00}$ preferably denote H or alkyl with 1 to 12 C-atoms, and $Y^1$ and $Y^2$ preferably denote F, Cl or Br.

Further preferably the polymer is selected of formula PIV:

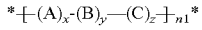　　　　　　　　　　　　　　　　PIV wherein

A, B, C independently of each other denote a distinct unit of formula PIIa, PIIb or PIII, x is >0 and ≤1, y is ≥0 and <1, z is ≥ 0 and <1, x+y+z is 1, and n1 is an integer >1.

Preferably at least one of B or C denotes a unit of formula IIa. Very preferably one of B and C denotes a unit of formula PIIa and one of B and C denotes a unit of formula PIIb.

A preferred polymer of formula PIV is selected from the following formulae

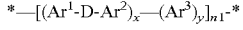　　　　　　　　　　PIVa

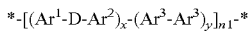　　　　　　　　　　PIVb

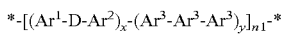　　　　　　　　　　PIVc

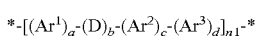　　　　　　　　　　PIVd

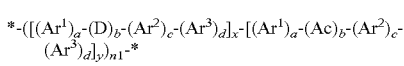　　　　　　　　　　PIVe

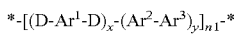　　　　　　　　　　PIVf

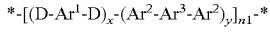　　　　　　　　　　PIVg

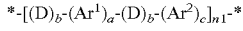　　　　　　　　　　PIVh

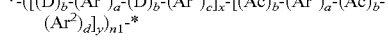　　　　　　　　　　PIVi

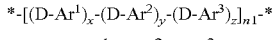　　　　　　　　　　PIVk wherein D, $Ar^1$, $Ar^2$, $Ar^3$, a, b, c and d have in each occurrence identically or differently one of the meanings given in formula PIIa, Ac has on each occurrence identically or differently one of the meanings given in formula PIIb, and x, y, z and n1 are as defined in formula PIV, wherein these polymers can be alternating or random copolymers, and wherein in formula PIVd and PIVe in at least one of the repeating units [(Ar$^1$)$_a$-(D)$_b$-(Ar$^2$)$_c$-(Ar$^3$)$_d$] and in at least one of the repeating units [(Ar$^1$)$_a$-(Ac)$_b$-(Ar$^2$)$_c$-(Ar$^3$)$_d$] b is at least 1 and wherein in formula PIVh and PIVi in at least one of the repeating units [(D)$_b$-(Ar$^1$)$_a$-(D)$_b$-(Ar$^2$)$_d$] and in at least one of the repeating units [(D)$_b$-(Ar$^1$)$_a$-(D)$_b$-(Ar$^2$)$_d$] b is at least 1.

In the polymers of formula PIV and its subformulae PIVa to PIVk, b is preferably 1 in all repeating units.

In the polymers of formula PIV and its subformulae PIVa to PIVk, x is preferably from 0.1 to 0.9, very preferably from 0.3 to 0.7.

In a preferred embodiment of the present invention one of y and z is 0 and the other is >0. In another preferred embodiment of the present invention, both y and z are 0. In yet another preferred embodiment of the present invention, both y and z are >0. If in the polymers of formula PIV and its subformulae PIVa to PIVk y or z is >0, it is preferably from 0.1 to 0.9, very preferably from 0.3 to 0.7.

In the polymer, the total number of repeating units n1 is preferably from 2 to 10,000. The total number of repeating units n1 is preferably ≥5, very preferably ≥10, most preferably ≥50, and preferably ≤500, very preferably ≤1,000, most preferably ≤2,000, including any combination of the aforementioned lower and upper limits of n1.

The polymer can be a homopolymer or copolymer, like a statistical or random copolymer, alternating copolymer or block copolymer, or a combination of the aforementioned.

Especially preferred is a polymer selected from the following groups:

- Group A consisting of homopolymers of the unit D or $(Ar^1-D)$ or $(Ar^1-D-Ar^2)$ or $(Ar^1-D-Ar^3)$ or $(D-Ar^2-Ar^3)$ or $(Ar^1-D-Ar^2-Ar^3)$ or $(D-Ar^1-D)$, i.e. where all repeating units are identical,
- Group B consisting of random or alternating copolymers formed by identical units $(Ar^1-D-Ar^2)$ or $(D-Ar^1-D)$ and identical units $(Ar^3)$,
- Group C consisting of random or alternating copolymers formed by identical units $(Ar^1-D-Ar^2)$ or $(D-Ar^1-D)$ and identical units $(A^1)$,
- Group D consisting of random or alternating copolymers formed by identical units $(Ar^1-D-Ar^2)$ or $(D-Ar^1-D)$ and identical units $(Ar^1-Ac-Ar^2)$ or $(Ac-Ar^1-Ac)$, wherein in all these groups D, Ac, $Ar^1$, $Ar^2$ and $Ar^3$ are as defined above and below, in groups A, B and C $Ar^1$, $Ar^2$ and $Ar^3$ are different from a single bond, and in group D one of $Ar^1$ and $Ar^2$ may also denote a single bond.

A preferred polymer of formula PIV and PIVa to PIVk is selected of formula PV $$R^{21}\text{-chain-}R^{22} \quad \text{PV}$$

wherein "chain" denotes a polymer chain of formulae PIV or PIVa to PIVk, and $R^{21}$ and $R^{22}$ have independently of each other one of the meanings of $R^S$ as defined above, or denote, independently of each other, H, F, Br, Cl, I, —CH$_2$Cl, —CHO, —CR'=CR"$_2$, —SiR'R"R''', —SiR'X'X", —SiR'R"X', —SnR'R"R''', —BR'R", —B(OR')(OR"), —B(OH)$_2$, —O—SO$_2$—R', —C≡CH, —C≡C—SiR'$_3$, —ZnX' or an endcap group, X' and X" denote halogen, R', R" and R''' have independently of each other one of the meanings of $R^0$ given in formula I, and two of R', R" and R''' may also form a cyclosilyl, cyclostannyl, cycloborane or cycloboronate group with 2 to 20 C atoms together with the respective hetero atom to which they are attached.

Preferred endcap groups $R^{21}$ and $R^{22}$ are H, C$_{1-20}$ alkyl, or optionally substituted C$_{6-12}$ aryl or C$_{2-10}$ heteroaryl, very preferably H or phenyl.

In the polymer represented by formula PIV, PIVa to PIVk or PV, x, y and z denote the mole fraction of units A, B and C, respectively, and n denotes the degree of polymerisation or total number of units A, B and C. These formulae includes block copolymers, random or statistical copolymers and alternating copolymers of A, B and C, as well as homopolymers of A for the case when x>0 and y=z=0.

In the repeating units and polymers of formulae PIIa, PIIb, PIII, PIV, PIVa-PIVk and PV, preferably D, $Ar^1$, $Ar^2$ and $Ar^3$ are selected from the group consisting of the following formulae

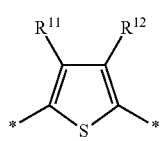
(D1)

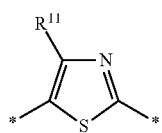
(D2)

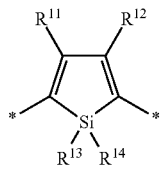
(D3)

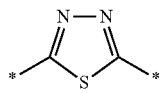
(D4)

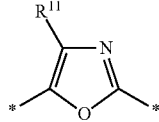
(D5)

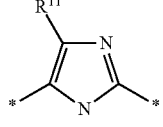
(D6)

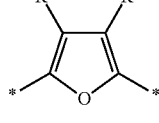
(D7)

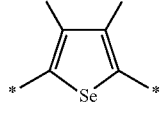
(D8)

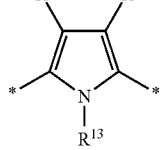
(D9)

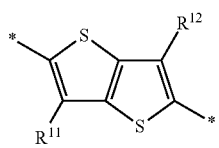
(D10)

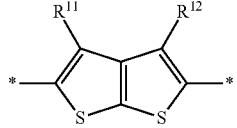
(D11)

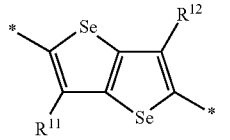
(D12)

(D13)

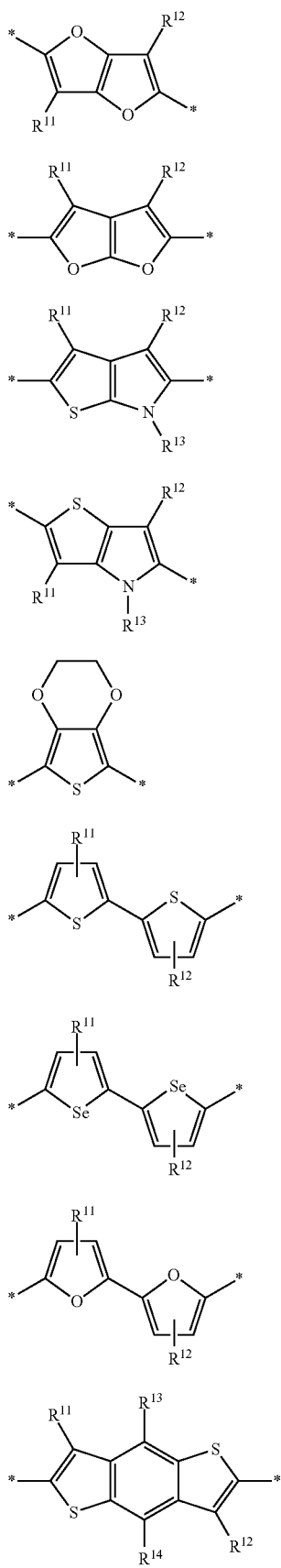
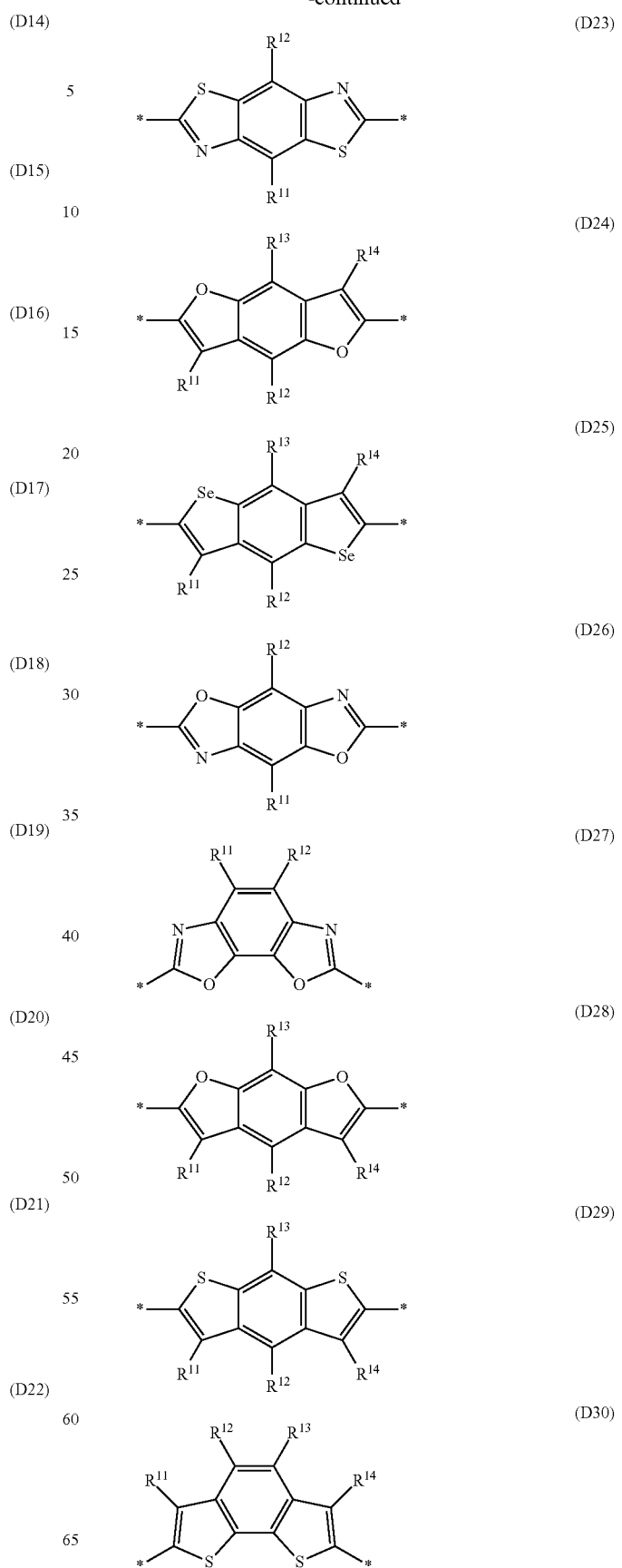

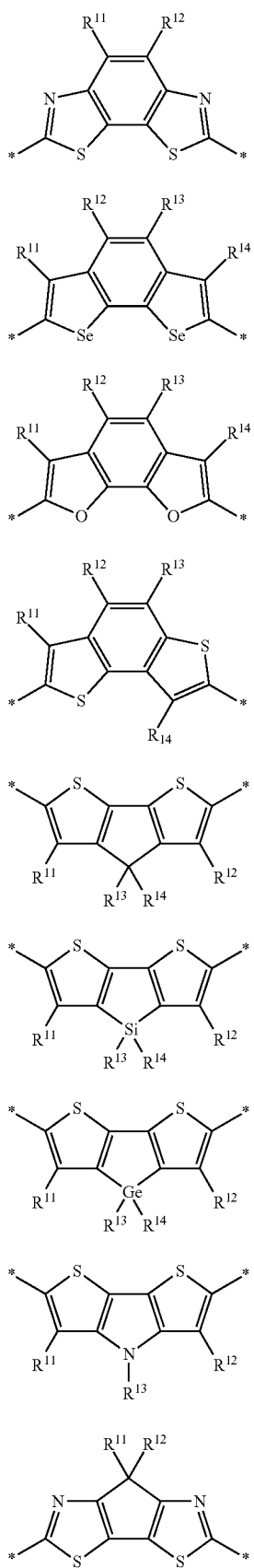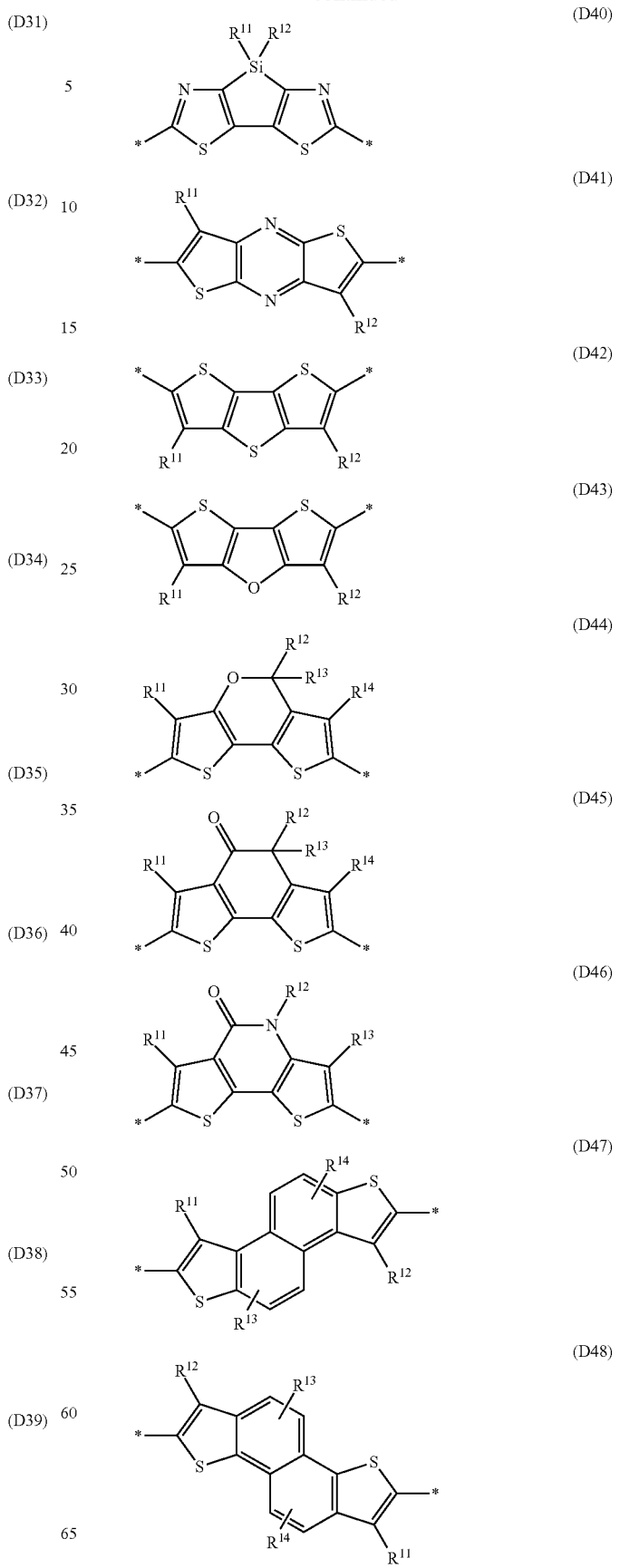

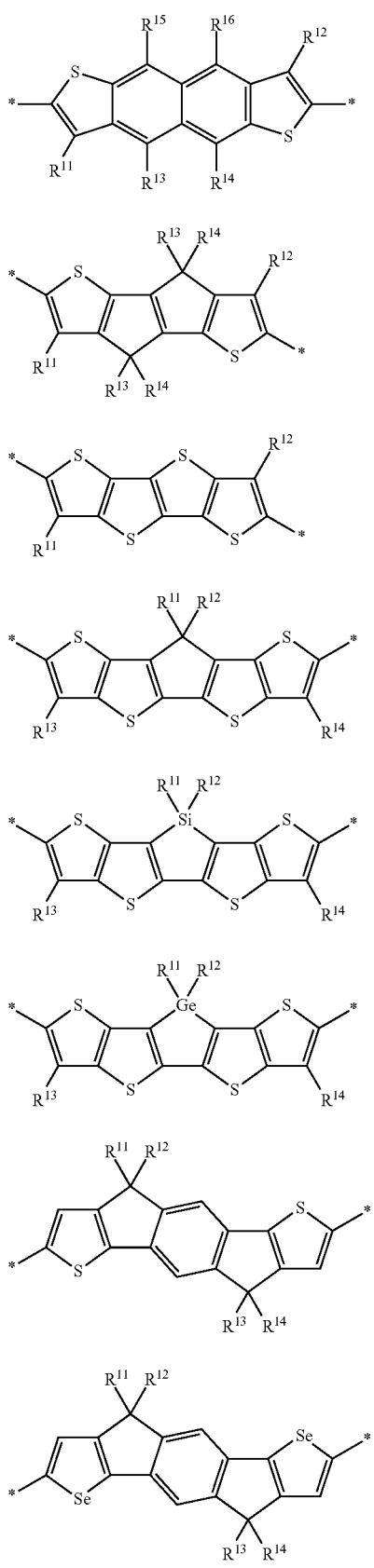
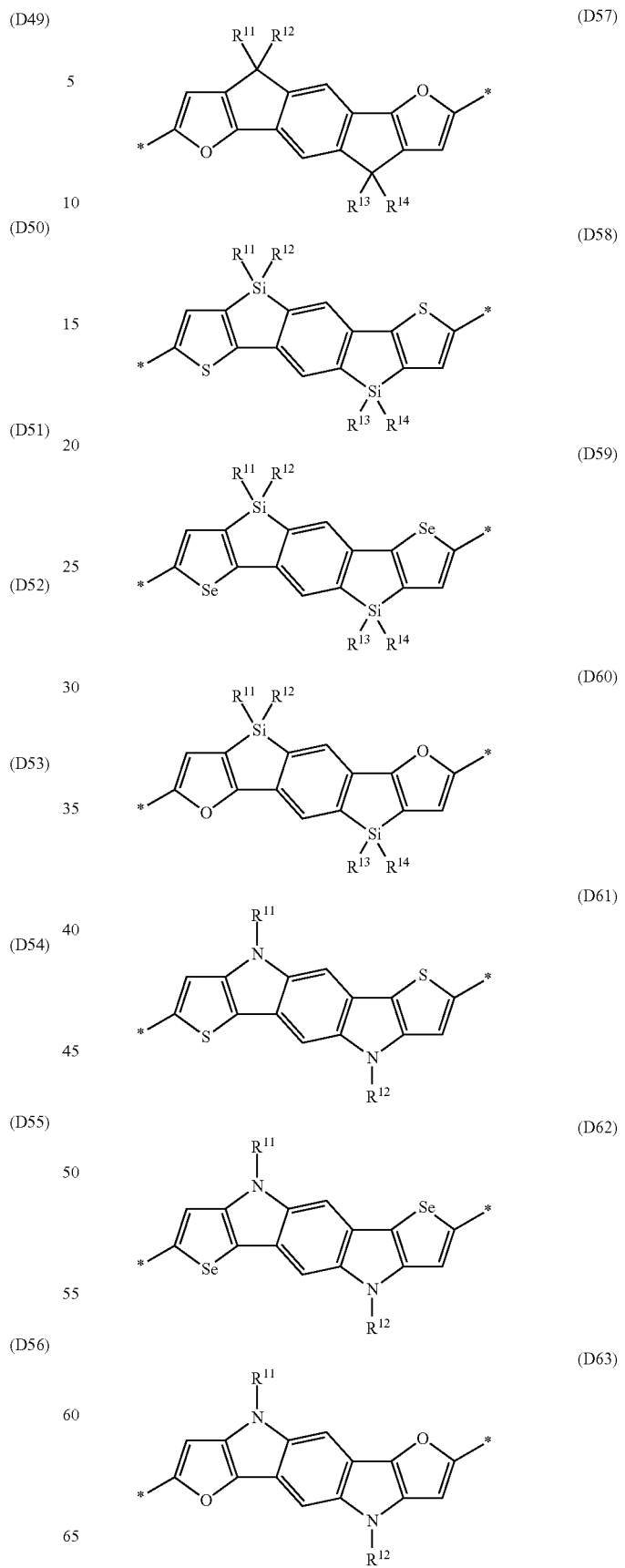

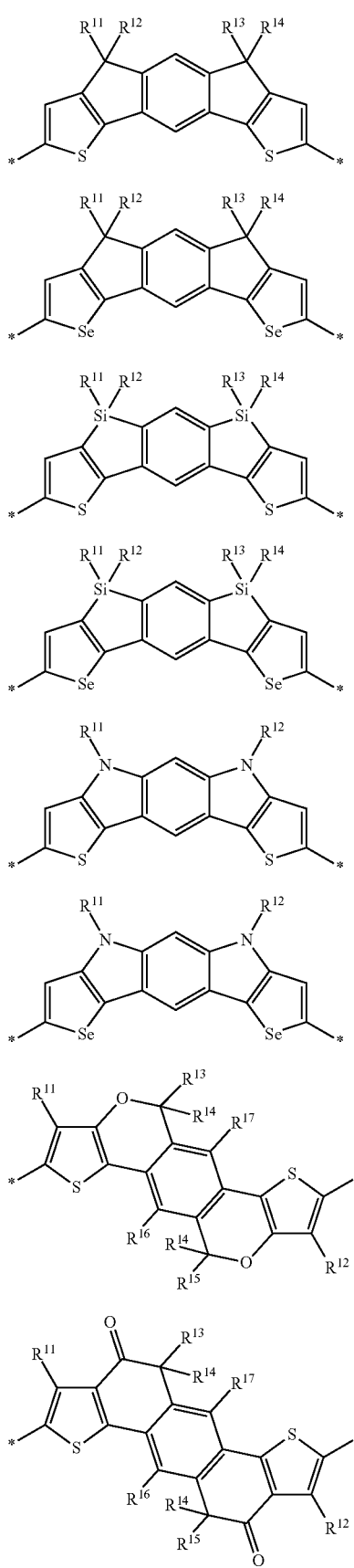
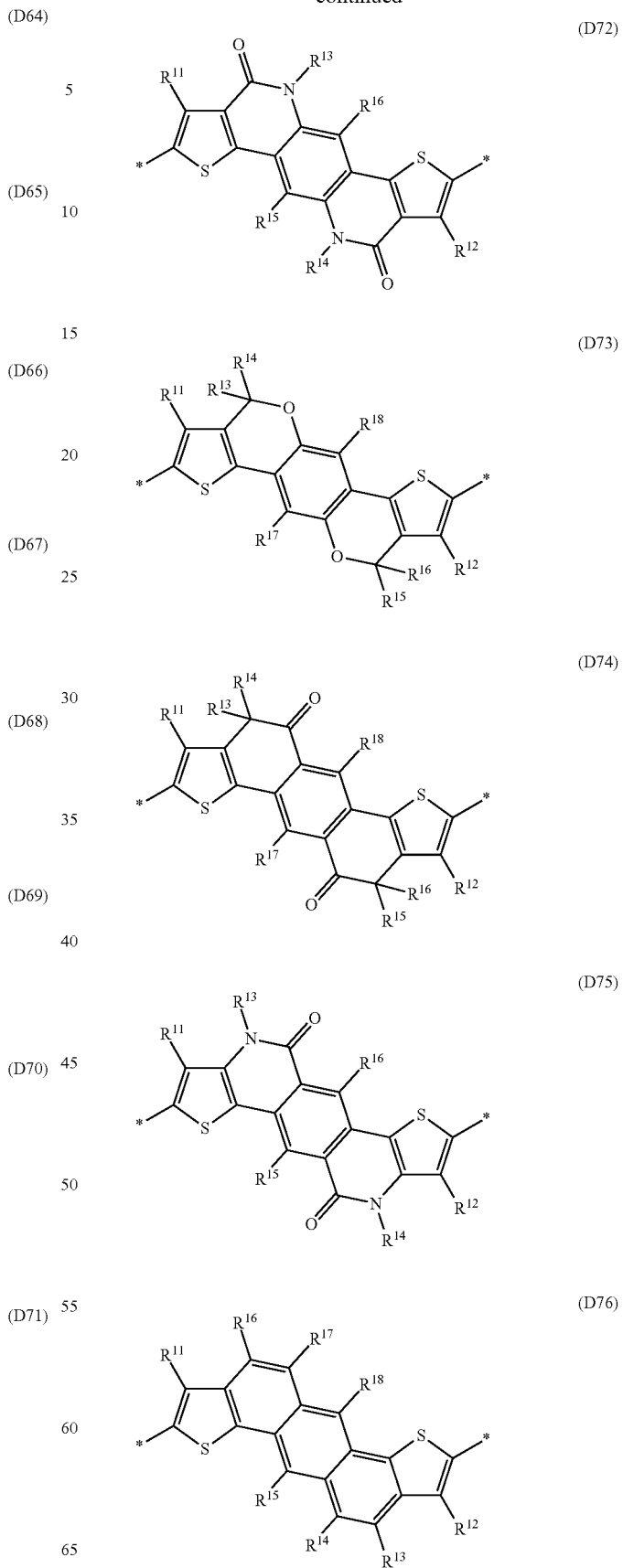

(D77)
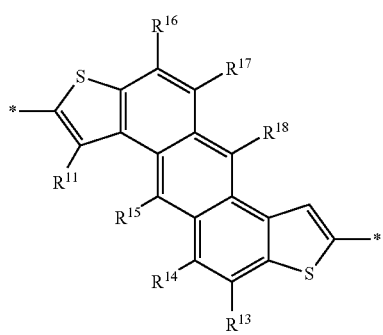
(D78)
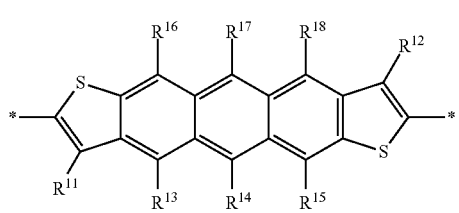
(D79)
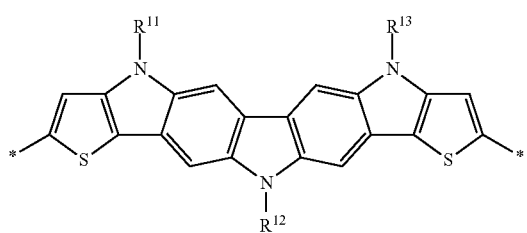
(D80)
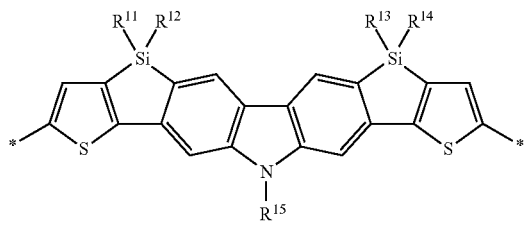
(D81)
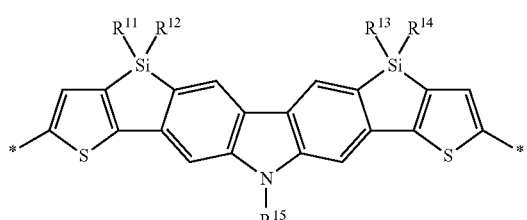
(D82)
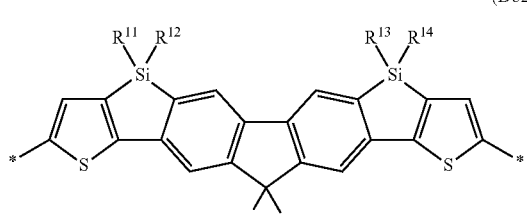
(D83)
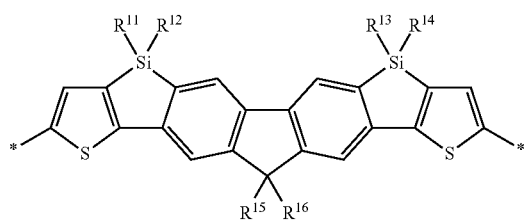
(D84)
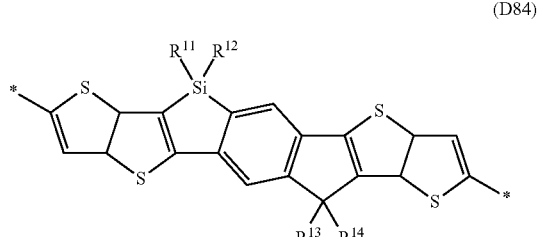
(D85)
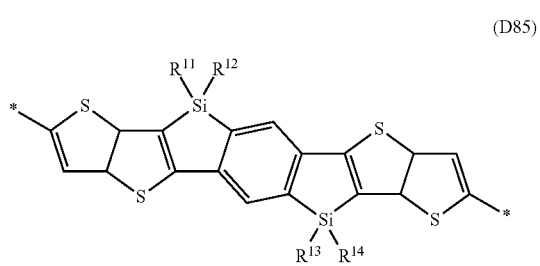
(D86)
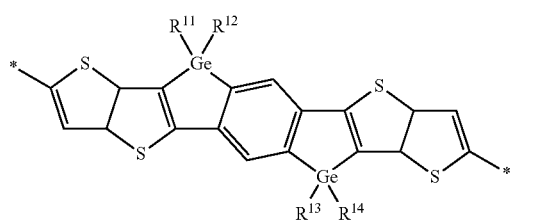
(D87)
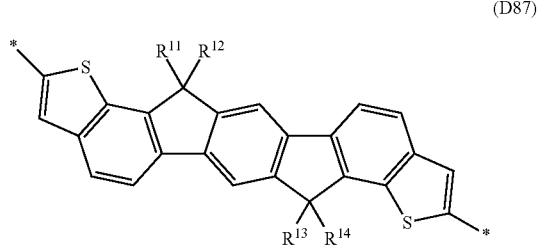
(D88)
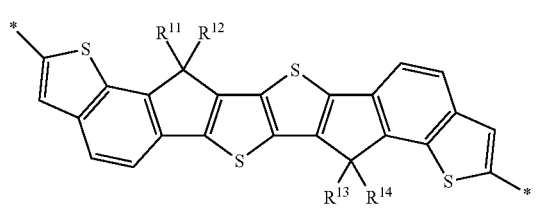

-continued
(D89)
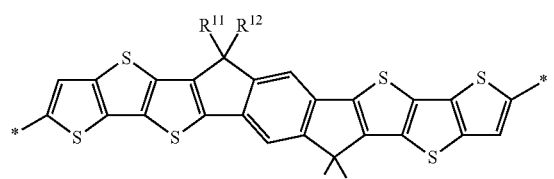
(D90)
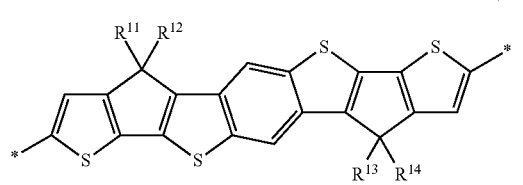
(D91)
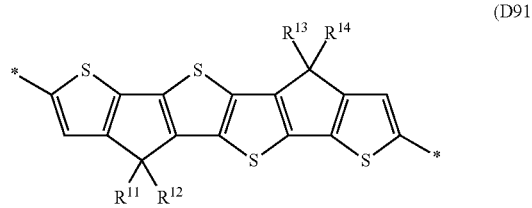
(D92)
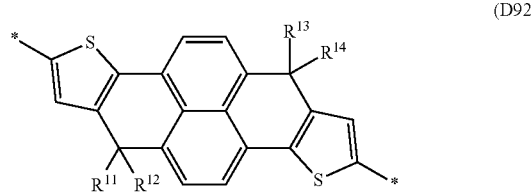
(D93)
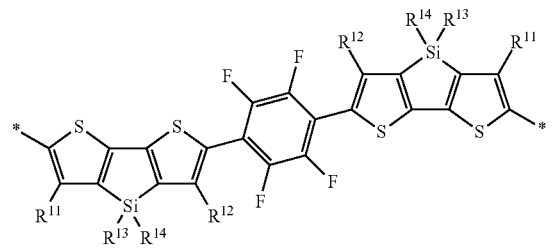
(D94)
(D95)
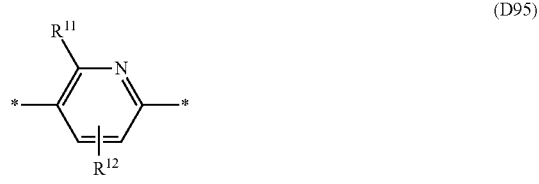
(D96)
-continued
(D97)
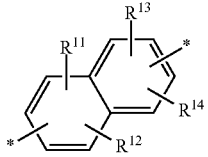
(D98)
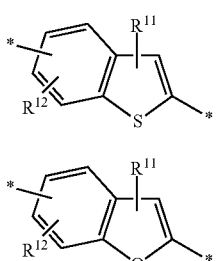
(D99)
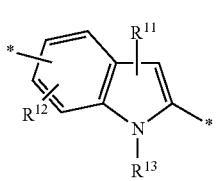
(D100)
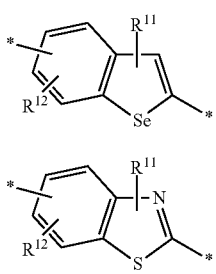
(D101)
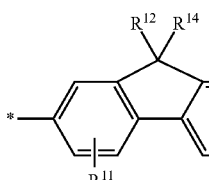
(D102)
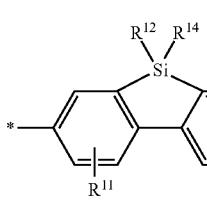
(D103)
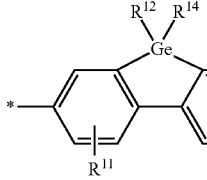
(D104)
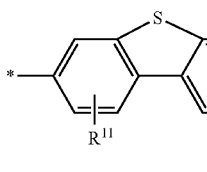
(D105)
(D106)

-continued (D107)

(D108)

(D109)

(D110)

(D111)

(D112)

(D113)

(D114)

(D115)

(D116)

(D117)

(D118)

(D119)

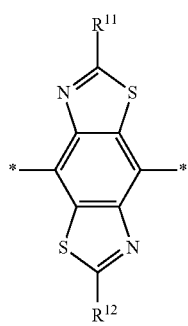
(D120)
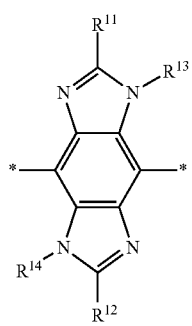
(D121)
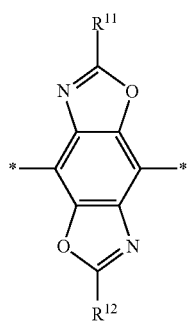
(D122)
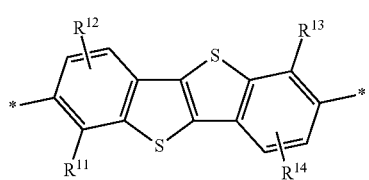
(D123)
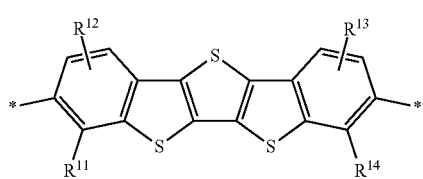
(D124)
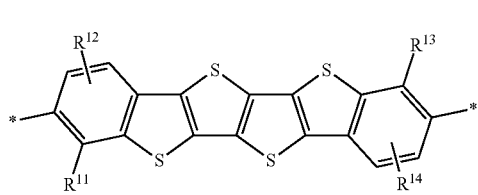
(D125)
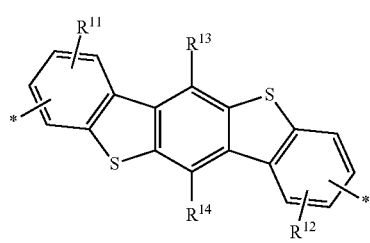
(D126)
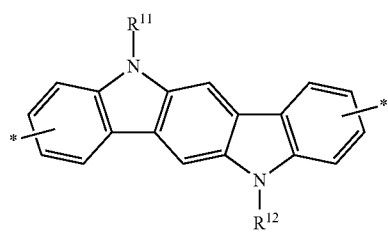
(D127)
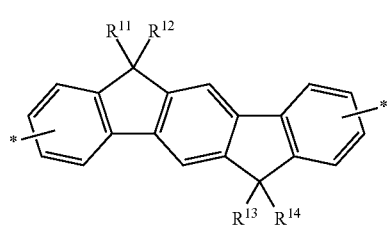
(D128)
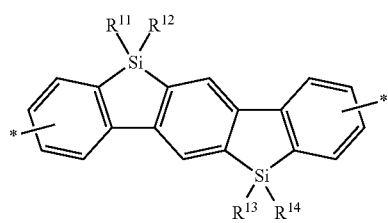
(D129)
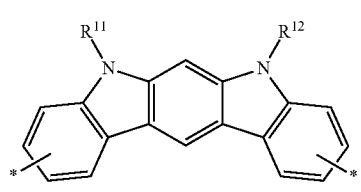
(D130)
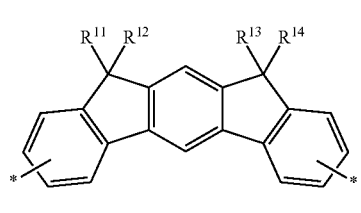
(D131)
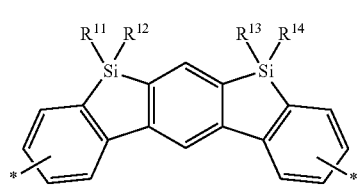
(D132)

-continued (D133) 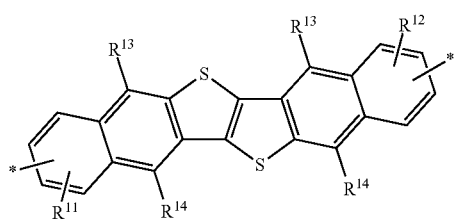

(D134) 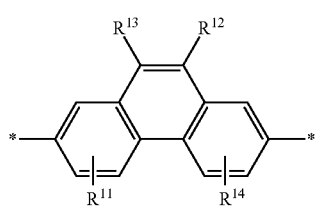

(D135) 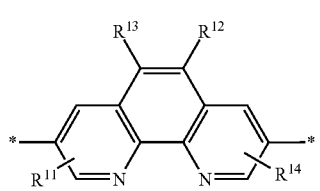

(D136) 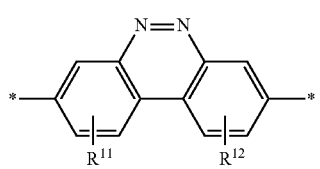

(D137) 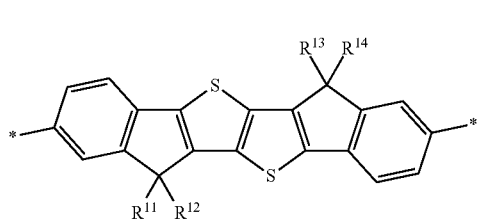

(D138) 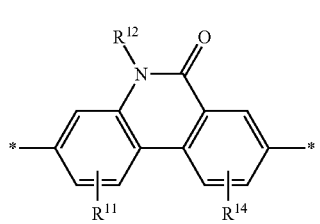

(D139) 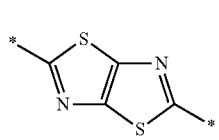

(D140) 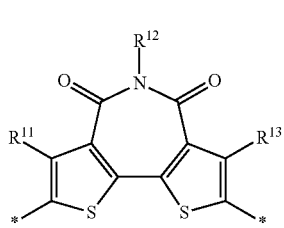

-continued (D141) 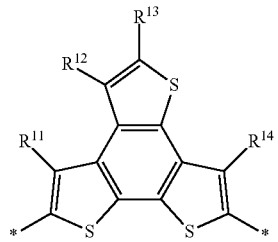

(D142) 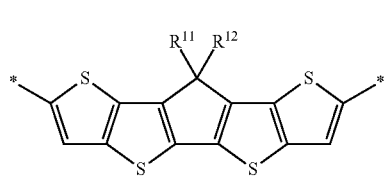

(D143) 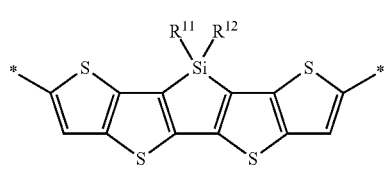

(D144) 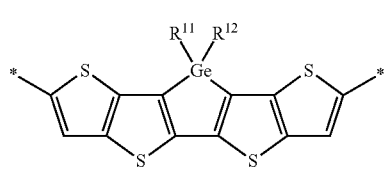

(D145) 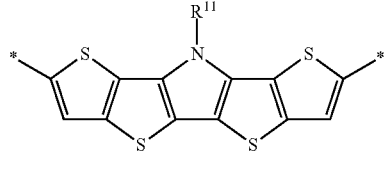

wherein $R^{11}$, $R^{12}$, $R^{13}$, $R^{14}$, $R^{15}$, $R^{16}$, $R^{17}$ and $R^{18}$ independently of each other denote H or have one of the meanings of $R^P$ as defined above and below.

In the repeating units and polymers of formulae PIIa, PIIb, PIII, PIV, PIVa-PIVk and PV, preferably Ac, $Ar^1$, $Ar^2$ and $Ar^3$ are selected from the group consisting of the following formulae (A1) 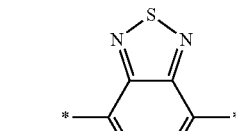

(A2) 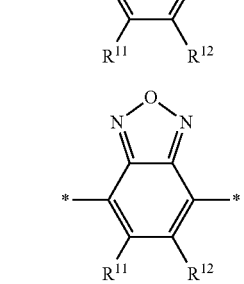

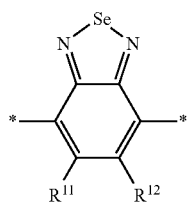
(A3)
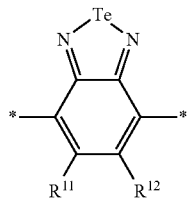
(A4)
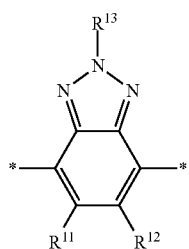
(A5)
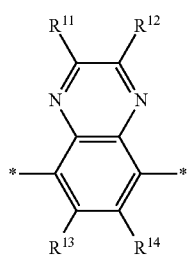
(A6)
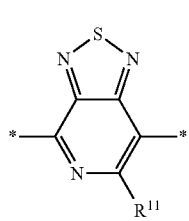
(A7)
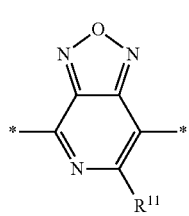
(A8)
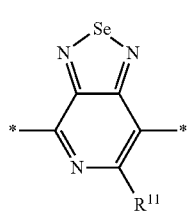
(A9)
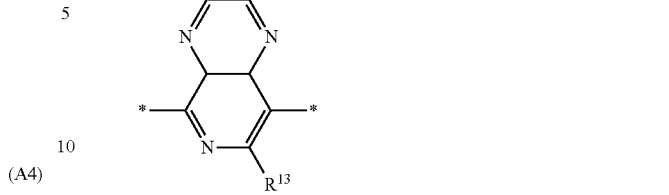
(A10)
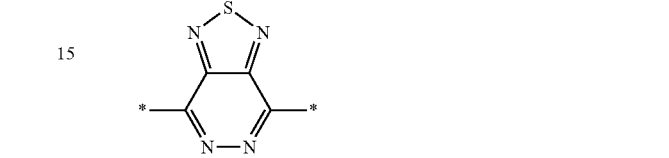
(A11)
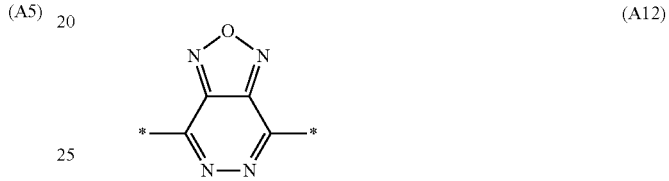
(A12)
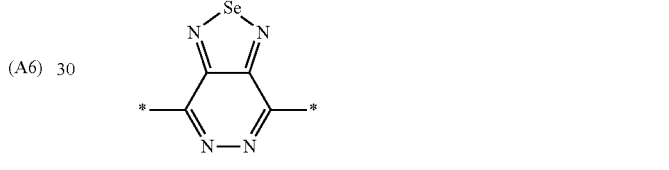
(A13)
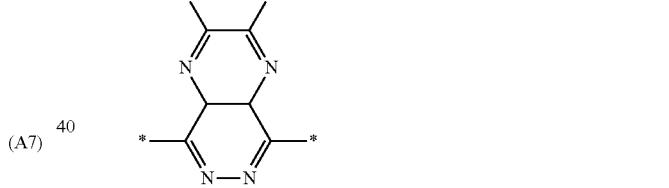
(A14)
(A15)
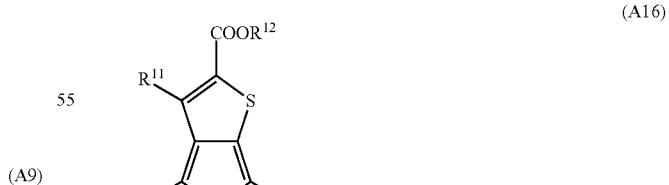
(A16)
(A17)

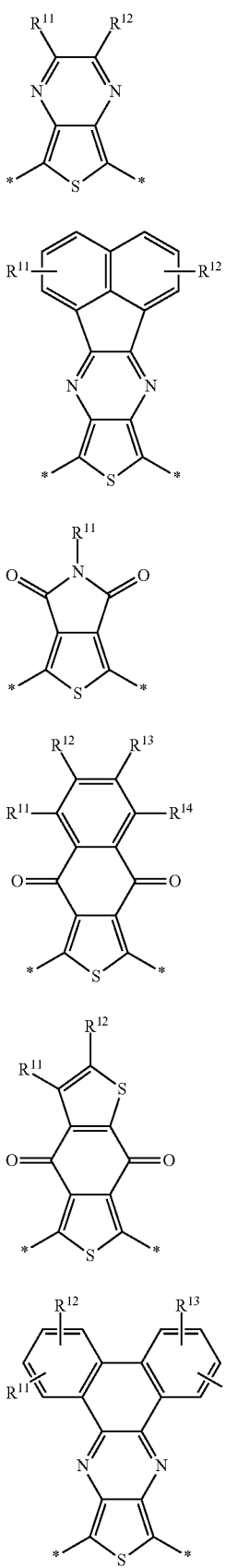
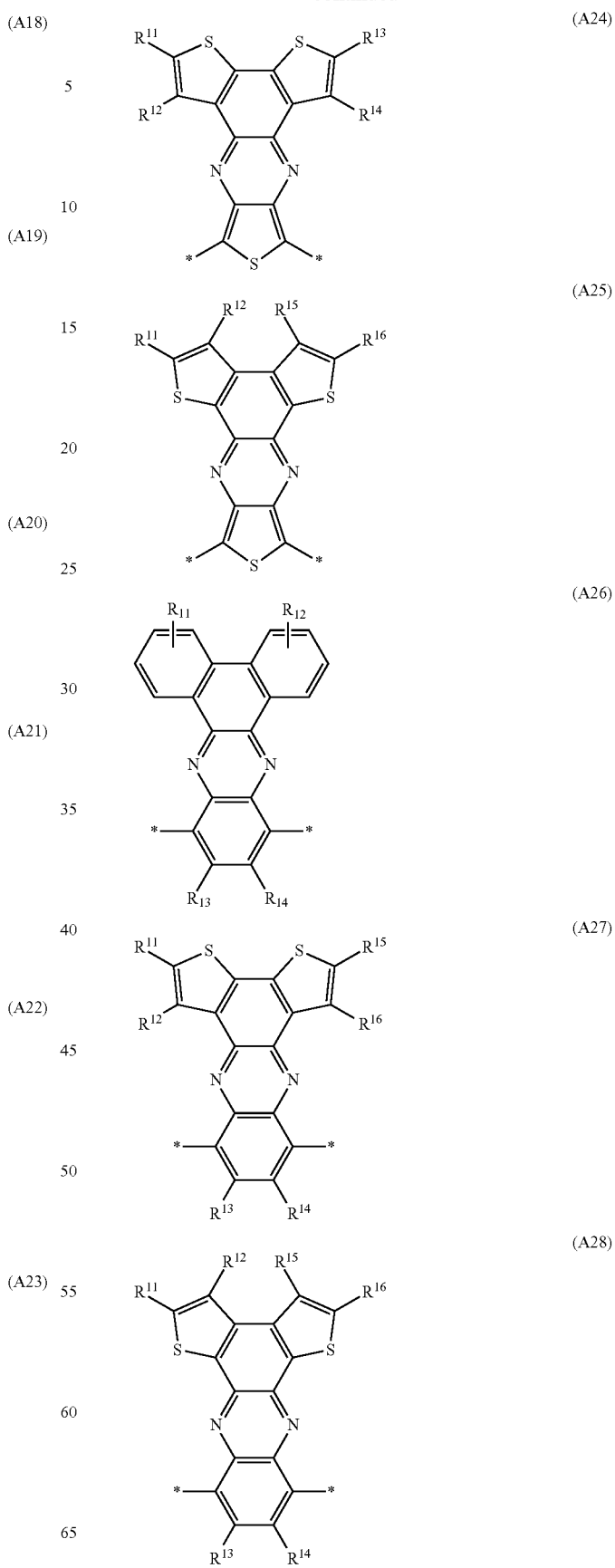

-continued
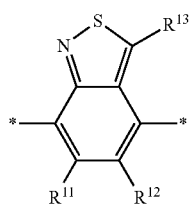
(A29)
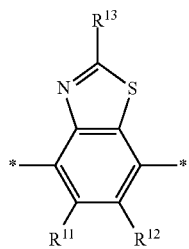
(A30)
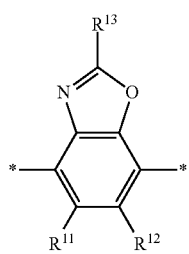
(A31)
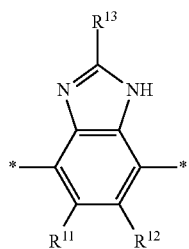
(A32)
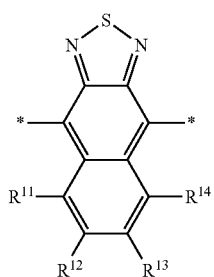
(A33)
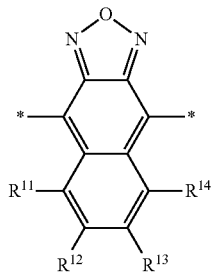
(A34)
-continued
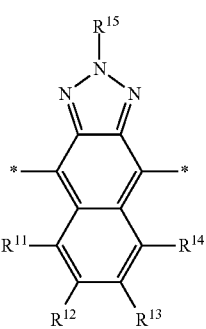
(A35)
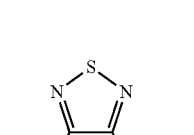
(A36)
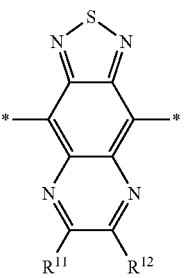
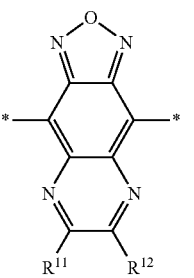
(A37)
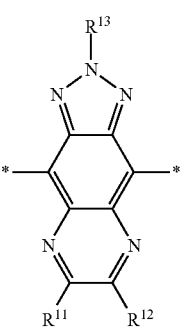
(A38)
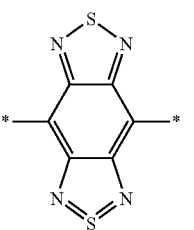
(A39)

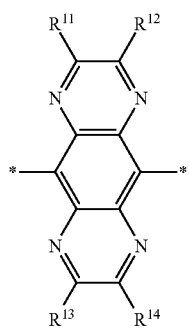
(A40)
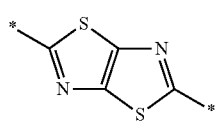
(A41)
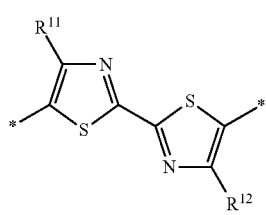
(A42)
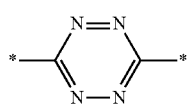
(A43)
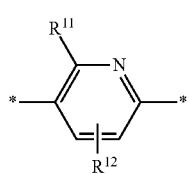
(A44)
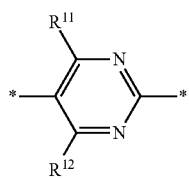
(A45)
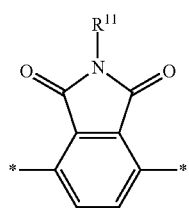
(A46)
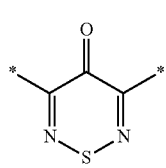
(A47)
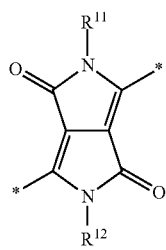
(A48)
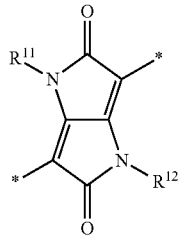
(A49)
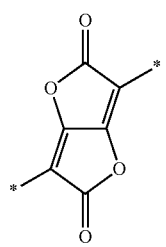
(A50)
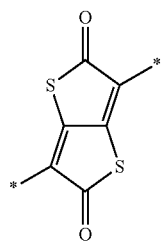
(A51)
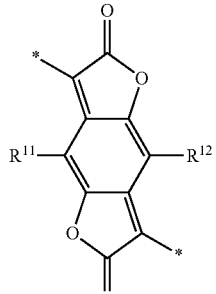
(A52)
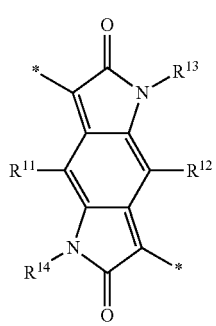
(A53)

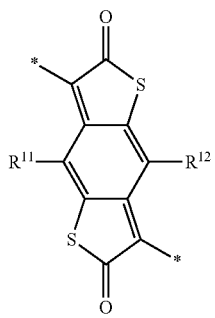
(A54)
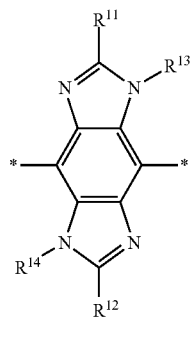
(A59)
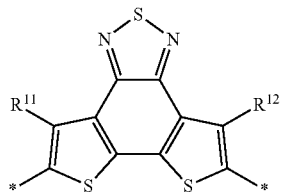
(A55)
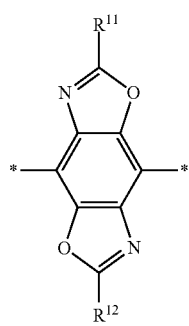
(A60)
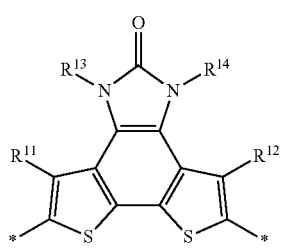
(A56)
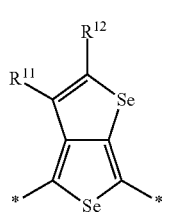
(A61)
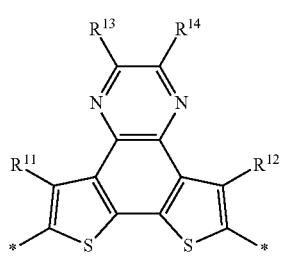
(A57)
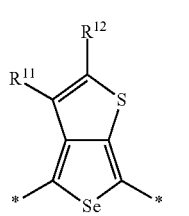
(A62)
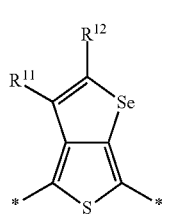
(A63)
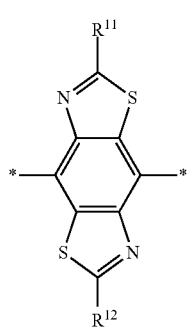
(A58)
(A64)

-continued
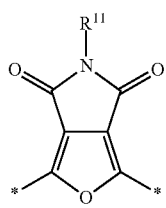
(A65)
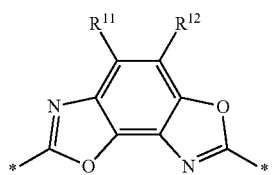
(A66)
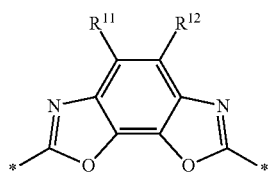
(A67)
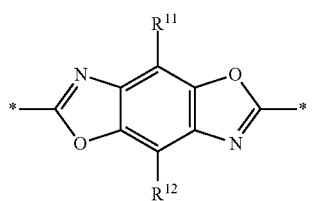
(A68)
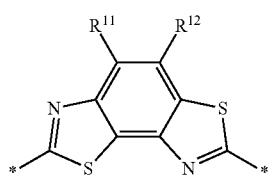
(A69)
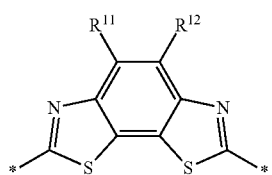
(A70)
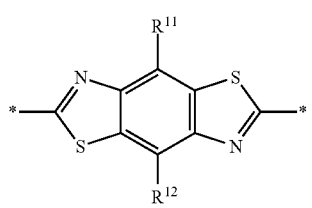
(A71)
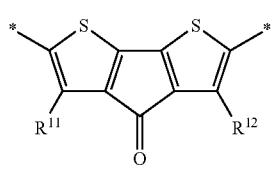
(A72)
-continued
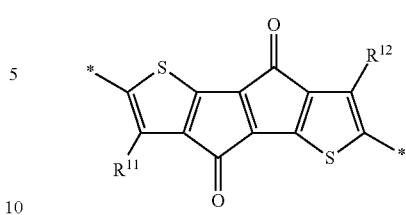
(A73)
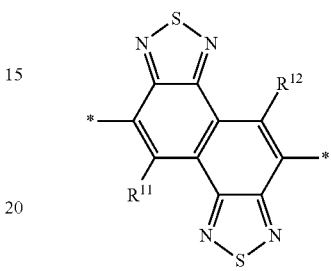
(A74)
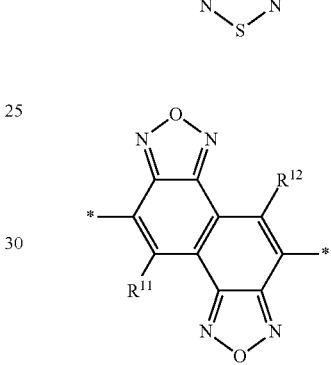
(A75)
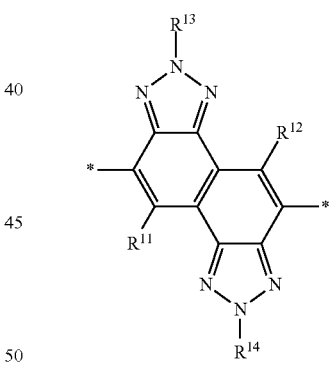
(A76)
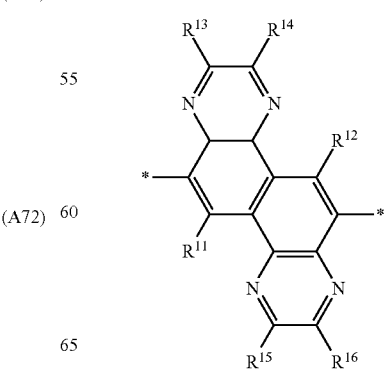
(A77)

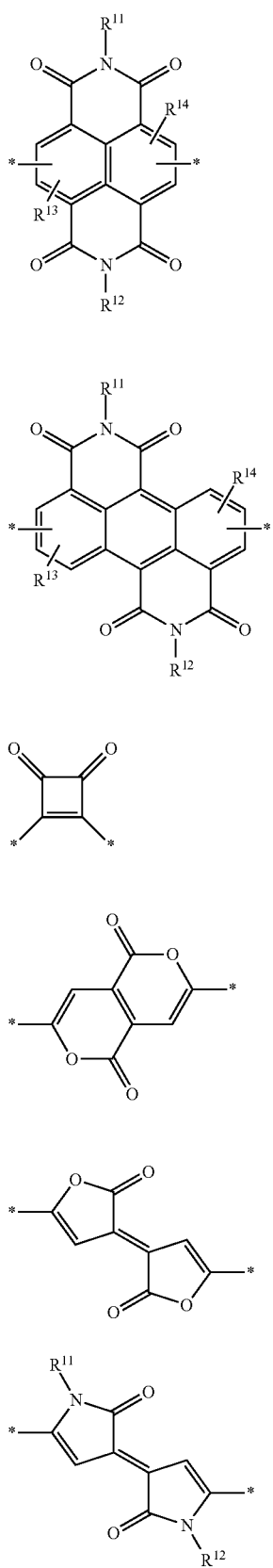
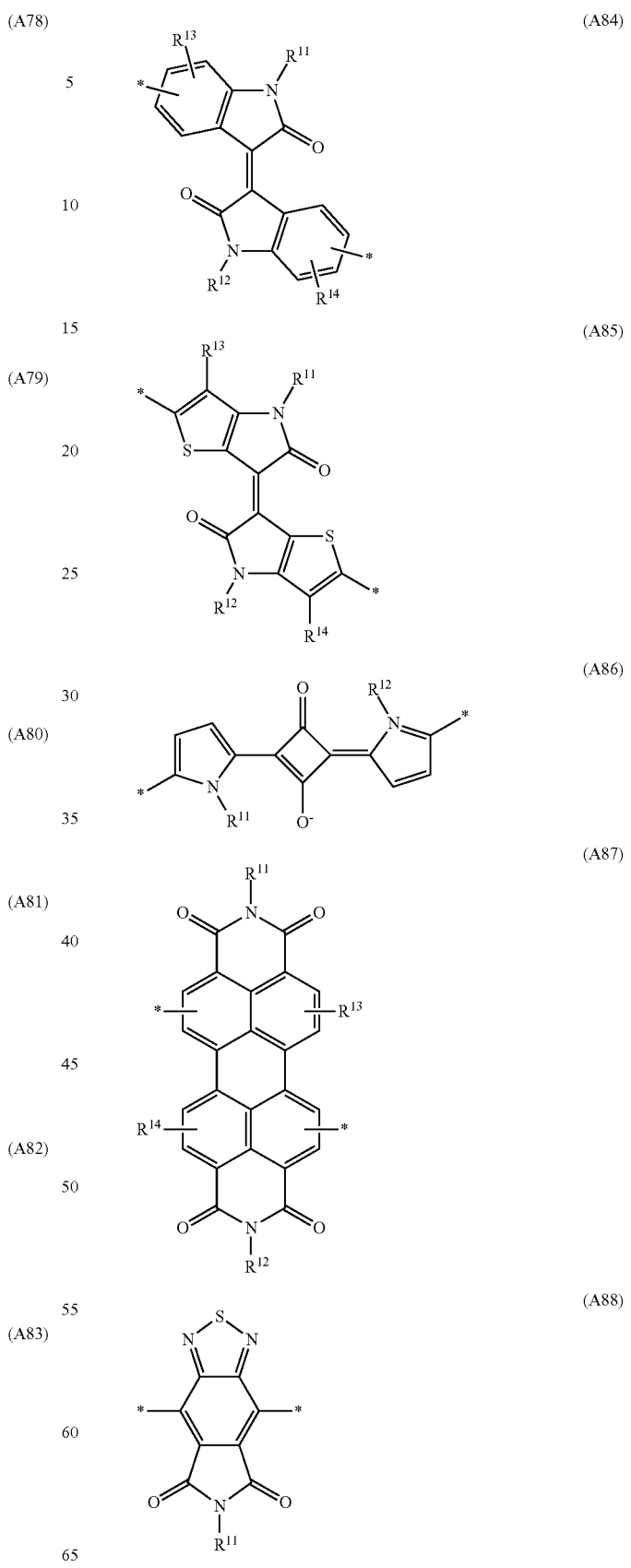

-continued (A89) 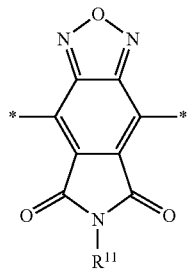

(A90) 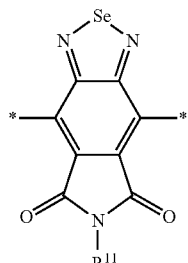

(A91) 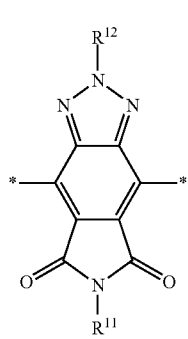

(A92) 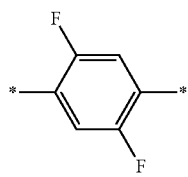

(A93) 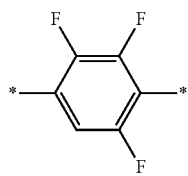

(A94) 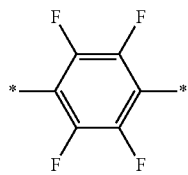

(A95) 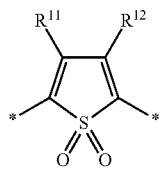

-continued (A96) 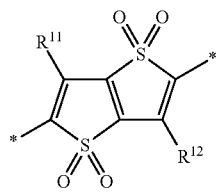

(A97) 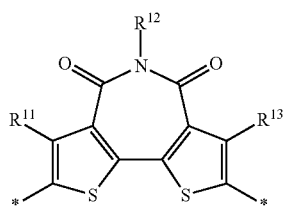

wherein $R^{11}$, $R^{12}$, $R^{13}$, $R^{14}$, $R^{15}$ and $R^{16}$ independently of each other denote H or have one of the meanings of $R^P$ as defined above and below.

The polymer can be prepared for example from monomers selected from the following formulae

| | |
|---|---|
| $R^{23}$-$(Ar^1)_a$-D-$(Ar^2)_c$-$R^{24}$ | PVIa |
| $R^{23}$-D-$(Ar^1)_a$-D-$R^{24}$ | PVIb |
| $R^{23}$-$(Ar^1)_a$-Ac-$(Ar^2)_c$-$R^{24}$ | PVIc |
| $R^{23}$-Ac-$(Ar^1)_a$-Ac-$R^{24}$ | PVId |
| $R^{23}$-$(Ar^1)_a$-$(Ar^2)_c$-$R^{24}$ | PVIe | wherein Ac, D, $Ar^1$, $Ar^2$, a and b have the meanings of formula PIIa and PIIb, or one of the preferred meanings as described above and below, and $R^{23}$ and $R^{24}$ are, preferably independently of each other, selected from the group consisting of H, Cl, Br, I, O-tosylate, O-triflate, O-mesylate, O-nona-flate, —SiMe$_2$F, —SiMeF$_2$, —O—SO$_2$Z$^1$, —B(OZ$^2$)$_2$, —CZ$^3$═C(Z$^3$)$_2$, —C≡CH, —C≡CSi(Z$^1$)$_3$, —ZnX$^0$ and —Sn(Z$^4$)$_3$, wherein X$^0$ is halogen, preferably Cl, Br or I, Z$^{1-4}$ are selected from the group consisting of alkyl and aryl, each being optionally substituted, and two groups Z$^2$ may also together form a cycloboronate group with 2 to 20 C atoms together with the B and O atoms.

Suitable monomers are for example selected from the following subformulae

| | |
|---|---|
| $R^{23}$-$Ar^1$-D-$Ar^2$-$R^{24}$ | PVIa1 |
| $R^{23}$-D-$R^{24}$ | PVIa2 |
| $R^{23}$-$Ar^1$-D-$R^{24}$ | PVIa3 |
| $R^{23}$-D-$Ar^2$-$R^{24}$ | PVIa4 |
| $R^{23}$-D-$Ar^1$-D-$R^{24}$ | PVIb1 |
| $R^{23}$-$Ar^1$-Ac-$Ar^2$-$R^{24}$ | PVIc1 |
| $R^{23}$-Ac-$R^{24}$ | PVIc2 |
| $R^{23}$-$Ar^1$-Ac-$R^{24}$ | PVIc3 |
| $R^{23}$-Ac-$Ar^2$-$R^{24}$ | PVIc4 |
| $R^{23}$-Ac-$Ar^1$-Ac-$R^{24}$ | PVId1 |

$$R^{23}\text{-}Ar^1\text{-}R^{24} \quad \text{PVIe1}$$

$$R^{23}\text{-}Ar^1\text{-}Ar^2\text{-}R^{24} \quad \text{PVIe2}$$

wherein Ac, D, $Ar^1$, $Ar^2$, a, c, $R^{23}$ and $R^{24}$ are as defined in formulae PVIa-PVIe.

The polymer can be synthesized according to or in analogy to methods that are known to the skilled person and are described in the literature. Other methods of preparation can be taken from the examples. For example, the polymers can be suitably prepared by aryl-aryl coupling reactions, such as Yamamoto coupling, Suzuki coupling, Stille coupling, Sonogashira coupling, C—H activation coupling, Heck coupling or Buchwald coupling. Suzuki coupling, Stille coupling and Yamamoto coupling are especially preferred. The monomers which are polymerised to form the repeat units of the polymers can be prepared according to methods which are known to the person skilled in the art.

For example the polymer can be prepared by coupling one or more monomers selected from formulae PVIa-PVIe and their subformulae in an aryl-aryl coupling reaction, wherein $R^{23}$ and $R^{24}$ are selected from Cl, Br, I, —B$(OZ^2)_2$ and —Sn$(Z^4)_3$.

Preferred aryl-aryl coupling and polymerisation methods used in the processes described above and below are Yamamoto coupling, Kumada coupling, Negishi coupling, Suzuki coupling, Stille coupling, Sonogashira coupling, Heck coupling, C—H activation coupling, Ullmann coupling or Buchwald coupling. Especially preferred are Suzuki coupling, Negishi coupling, Stille coupling and Yamamoto coupling. Suzuki coupling is described for example in WO 00/53656 A1. Negishi coupling is described for example in *J. Chem. Soc., Chem. Commun.*, 1977, 683-684. Yamamoto coupling is described in for example in T. Yamamoto et al., *Prog. Polym. Sci.*, 1993, 17, 1153-1205, or WO 2004/022626 A1, and Stille coupling is described for example in Z. Bao et al., *J. Am. Chem. Soc.*, 1995, 117, 12426-12435. For example, when using Yamamoto coupling, monomers having two reactive halide groups are preferably used. When using Suzuki coupling, monomers of formulae PVIa-PVId and their subformulae having two reactive boronic acid or boronic acid ester groups or two reactive halide groups are preferably used. When using Stille coupling, monomers having two reactive stannane groups or two reactive halide groups are preferably used. When using Negishi coupling, monomers having two reactive organozinc groups or two reactive halide groups are preferably used.

Preferred catalysts, especially for Suzuki, Negishi or Stille coupling, are selected from Pd(0) complexes or Pd(II) salts. Preferred Pd(0) complexes are those bearing at least one phosphine ligand such as Pd(Ph$_3$P)$_4$. Another preferred phosphine ligand is tris(ortho-tolyl)phosphine, i.e. Pd(o-Tol$_3$P)$_4$. Preferred Pd(II) salts include palladium acetate, i.e. Pd(OAc)$_2$. Alternatively the Pd(0) complex can be prepared by mixing a Pd(0) dibenzylideneacetone complex, for example tris(dibenzyl-ideneacetone)dipalladium(0), bis(dibenzylideneacetone)-palladium(0), or Pd(II) salts e.g. palladium acetate, with a phosphine ligand, for example triphenylphosphine, tris(ortho-tolyl)phosphine or tri(tert-butyl)phosphine. Suzuki polymerisation is performed in the presence of a base, for example sodium carbonate, potassium carbonate, lithium hydroxide, potassium phosphate or an organic base such as tetraethylammonium carbonate or tetraethylammonium hydroxide. Yamamoto polymerisation employs a Ni(0) complex, for example bis(1,5-cyclooctadienyl) nickel(0).

Suzuki and Stille polymerisation may be used to prepare homopolymers as well as statistical, alternating and block random copolymers. Statistical or block copolymers can be prepared for example from the above monomers of formula PVI or its subformulae, wherein one of the reactive groups is halogen and the other reactive group is a boronic acid, boronic acid derivative group or and alkylstannane. The synthesis of statistical, alternating and block copolymers is described in detail for example in WO 03/048225 A2 or WO 2005/014688 A2.

The concentration of the fullerene derivatives of this invention, or of the fullerene composition, in a formulation according to the present invention, including solvents, is preferably 0.1 to 10% by weight, more preferably 0.5 to 5% by weight. The concentration of the fullerene derivatives of this invention in a composition comprising a fullerene derivative and a polymer according to the present invention (i.e. excluding solvents), is preferably from 10 to 90% by weight, very preferably from 33% to 80% by weight.

Another aspect of the present invention relates to a formulation comprising one or more fullerene derivatives of this invention or a fullerene composition as described above, and further comprising one or more solvents, preferably selected from organic solvents.

Such a formulation is preferably used as a carrier for the preparation of a semiconducting layer of an electronic device, like an OPV or OPD device, wherein the fullerene derivative or fullerene composition is for example used in the photoactive layer.

Optionally, the formulation further comprises one or more binders to adjust the rheological properties, as described for example in WO 2005/055248 A1.

The formulations according to the present invention preferably form a solution.

The invention additionally provides an electronic device comprising a fullerene derivative of this invention or fullerene composition, or a semiconducting layer comprising it, as described above and below.

Especially preferred devices are OFETs, TFTs, ICs, logic circuits, capacitors, RFID tags, OLEDs, OLETs, OPEDs, OPVs, OPDs, perovskite-based solar cells, dye sensitizer solar cells, solar cells, laser diodes, photoconductors, photodetectors, electrophotographic devices, electrophotographic recording devices, organic memory devices, sensor devices, charge injection layers, Schottky diodes, planarising layers, antistatic films, conducting substrates and conducting patterns.

Especially preferred electronic device are OFETs, OLEDs, OPV and OPD devices, in particular bulk heterojunction (BHJ) OPV devices and OPD devices. In an OFET, for example, the active semiconductor channel between the drain and source may comprise the layer of the invention. As another example, in an OLED device, the charge (hole or electron) injection or transport layer may comprise the layer of the invention. As another example, in a perovskite solar cell device, the charge (hole or electron) injection, interlayer or transport layer may comprise the layer of the invention.

For use in OPV or OPD devices, preferably a fullerene composition is used that contains a p-type (electron donor) semiconductor and an n-type (electron acceptor) semiconductor. The p-type semiconductor is for example a conjugated polymer having repeating units of formulae PIIa, PIIb or PIII, or a polymer of formula PIV, PV or their subformulae, as shown above, a small molecules, a mixture of a two or more polymers or mixture of one or more polymers and one or more small molecules. The n-type semiconductor is a fullerene derivative of this invention, a mixture of two or more fullerenes, at least one of which is a fullerene derivative of this invention.

The device preferably further comprises a first transparent or semi-transparent electrode on a transparent or semi-transparent substrate on one side of the active layer, and a second metallic or semi-transparent electrode on the other side of the active layer.

Preferably, the active layer according to the present invention is further blended with additional organic and inorganic compounds to enhance the device properties. For example, metal particles such as Au or Ag nanoparticules or Au or Ag nanoprism for enhancements in light harvesting due to near-field effects (i.e. plasmonic effect) as described, for example in Adv. Mater. 2013, 25 (17), 2385-2396 and Adv. Ener. Mater. 10.1002/aenm.201400206, a molecular dopant such as 2,3,5,6-tetrafluoro-7,7,8,8-tetracyanoquinodimethane for enhancement in photoconductivity as described, for example in Adv. Mater. 2013, 25(48), 7038-7044, or a stabilising agent consisting of a UV absorption agent and/or anti-radical agent and/or antioxidant agent such as 2-hydroxybenzophenone, 2-hydroxyphenylbenzotriazole, oxalic acid anilides, hydroxyphenyl triazines, merocyanines, hindered phenol, N-aryl-thiomorpholine, N-aryl-thiomorpholine-1-oxide, N-aryl-thiomorpholine-1,1-dioxide, N-aryl-thiazolidine, N-aryl-thiazolidine-1-oxide, N-aryl-thiazolidine-1,1-dioxide and 1,4-diazabicyclo[2.2.2]octane as described, for example, in WO2012095796 A1 and in WO2013021971 A1.

The device preferably may further comprise a UV to visible photo-conversion layer such as described, for example, in J. Mater. Chem. 2011, 21, 12331 or a NIR to visible or IR to NIR photo-conversion layer such as described, for example, in J. Appl. Phys. 2013, 113, 124509.

Further preferably the OPV or OPD device comprises, between the active layer and the first or second electrode, one or more additional buffer layers acting as hole transporting layer and/or electron blocking layer, which comprise a material such as metal oxides, like for example, ZTO, $MoO_x$, $NiO_x$ a doped conjugated polymer, like for example PEDOT:PSS and polypyrrole-polystyrene sulfonate (PPy:PSS), a conjugated polymer, like for example polytriarylamine (PTAA), an organic compound, like for example substituted triaryl amine derivatives such as N,N'-diphenyl-N,N'-bis(1-naphthyl)(1,1-biphenyl)-4,4'diamine (NPB), N,N'-diphenyl-N,N'-(3-methylphenyl)-1,1'-biphenyl-4,4'-diamine (TPD), graphene based materials, like for example, graphene oxide and graphene quantum dots or alternatively as hole blocking layer and/or electron transporting layer, which comprise a material such as metal oxide, like for example, $ZnO_x$, $TiO_x$, AZO (aluminium doped zinc oxide), a salt, like for example LiF, NaF, CsF, a conjugated polymer electrolyte, like for example poly[3-(6-trimethylammoniumhexyl) thiophene], poly(9,9-bis(2-ethylhexyl)-fluorene]-b-poly[3-(6-trimethylammoniumhexyl)thiophene], or poly[(9,9-bis (3'-(N,N-dimethylamino)propyl)-2,7-fluorene)-alt-2,7-(9,9-dioctylfluorene)], a polymer, like for example poly (ethyleneimine) or crosslinked N-containing compound derivatives or an organic compound, like for example tris (8-quinolinolato)-aluminium(III) ($Alq_3$), phenanthroline derivative or $C_{60}$ or $C_{70}$ based fullerenes, like for example, as described in Adv. Energy Mater. 2012, 2, 82-86.

In a fullerene composition comprising a fullerene derivative and a polymer according to the present invention, the ratio polymer:fullerene derivative is preferably from 5:1 to 1:5 by weight, more preferably from 1:0.5 to 1:3 by weight, most preferably 1:1 to 1:2 by weight. A polymeric binder may also be included, from 5 to 95% by weight. Examples of binder include polystyrene (PS), polypropylene (PP) and polymethylmethacrylate (PMMA).

To produce thin layers in electronic devices, like BHJ OPV devices, a fullerene derivative, fullerene composition or formulation according to the present invention may be deposited by any suitable method. Liquid coating of devices is more desirable than vacuum deposition techniques. Solution deposition methods are especially preferred. The formulations of the present invention enable the use of a number of liquid coating techniques. Preferred deposition techniques include, without limitation, dip coating, spin coating, ink jet printing, nozzle printing, letter-press printing, screen printing, gravure printing, doctor blade coating, roller printing, reverse-roller printing, offset lithography printing, dry offset lithography printing, flexographic printing, web printing, spray coating, curtain coating, brush coating, slot dye coating or pad printing. For the fabrication of OPV devices and modules area printing method compatible with flexible substrates are preferred, for example slot dye coating, spray coating and the like.

When preparing a suitable solution or formulation containing a composition with a fullerene derivative (as n-type component) and a polymer (as p-type component) according to the present invention, a suitable solvent should be selected so as to ensure full dissolution of both the p-type and the n-type component, and to take into account the boundary conditions (for example rheological properties) introduced by the chosen printing method.

Organic solvents are generally used for this purpose. Typical solvents can be aromatic solvents, halogenated solvents or chlorinated solvents, including chlorinated aromatic solvents. Preferred solvents are aliphatic hydrocarbons, chlorinated hydrocarbons, aromatic hydrocarbons, ketones, ethers and mixtures thereof. Examples include, but are not limited to dichloromethane, trichloromethane, tetrachloromethane, chlorobenzene, o-dichlorobenzene, 1,2,4-trichlorobenzene, 1,2-dichloroethane, 1,1,1-trichloroethane, 1,1,2,2-tetrachloroethane, 1,8-diiodooctane, 1-chloronaphthalene, 1,8-octane-dithiol, anisole, 2-methylanisole, phenetol, 4-methyl-anisole, 3-methylanisole, 2,6-dimethylanisole, 2,5-di-methylanisole, 2,4-dimethylanisole, 3,5-dimethylanisole, 4-fluoroanisole, 3-fluoro-anisole, 3-trifluoro-methylanisole, 4-fluoro-3-methylanisole, 2-fluoroanisole, toluene, o-xylene, m-xylene, p-xylene, mixture of xylene o-, m-, and p-isomers, 1,2,4-trimethylbenzene, 1,2,3,4-tetra-methyl benzene, pentylbenzene, mesitylene, cumene, cymene, cyclohexylbenzene, diethylbenzene, cyclohexane, 1-methylnaphthalene, 2-methylnaphthalene, 1,2-dimethylnaphthalene, tetraline, decaline, indane, 1-methyl-4-(1-methylethenyl)-cyclohexene (d-Limonene), 6,6-dimethyl-2-methylenebicyclo[3.1.1]heptanes (β-pinene), 2,6-lutidine, 2-fluoro-m-xylene, 3-fluoro-o-xylene, 2-chloro-benzotrifluoride, 2-chloro-6-fluorotoluene, 2,3-dimethylpyrazine, 2-fluorobenzonitrile, 4-fluoroveratrol, 3-fluorobenzo-nitrile, 1-fluoro-3,5-dimethoxy-benzene, 3-fluorobenzotrifluoride, benzotrifluoride, trifluoromethoxy-benzene, 4-fluorobenzotrifluoride, 3-fluoropyridine, toluene, 2-fluoro-toluene, 2-fluorobenzotrifluoride, 3-fluorotoluene, 4-isopropylbiphenyl, phenyl ether, pyridine, 4-fluorotoluene, 2,5-difluorotoluene, 1-chloro-2,4-difluorobenzene, 2-fluoropyridine, 3-chlorofluoro-benzene, 1-chloro-2,5-difluorobenzene, 4-chlorofluorobenzene, 2-chlorofluorobenzene, methyl benzoate, ethyl benzoate, nitrobenzene, benzaldehyde, benzonitrile, tetrahydrofuran, 1,4-dioxane, 1,3-dioxane, morpholine, acetone, methylethylketone, ethyl acetate, n-butyl acetate, N,N-dimethylaniline, N,N-dimethylformamide, N-methylpyrrolidinone, dimethylacetamide, dimethylsulfoxide and/or mixtures thereof.

Especially preferred are solvents selected from aliphatic or aromatic hydrocarbons, or mixtures thereof, which are non-chlorinated.

Further preferred are solvents selected from non-chlorinated aliphatic or aromatic hydrocarbons, or mixtures thereof, which contain less than 5% of halogenated but non-chlorinated (e.g. fluorinated, brominated or iodinated) aliphatic or aromatic hydrocarbons, like e.g. 1,8-diiodooctane.

Preferred solvents of this type are selected from 1,2,4-trimethylbenzene, 1,2,3,4-tetra-methyl benzene, pentylbenzene, mesitylene, cumene, cymene, cyclohexylbenzene, diethylbenzene, tetralin, decalin, 2,6-lutidine, N,N-dimethylformamide, 2,3-dimethylpyrazine, 2-methylanisole, phenetol, 4-methyl-anisole, 3-methylanisole, 2,5-dimethylanisole, 2,4-dimethylanisole, 3,5-dimethyl-anisole, N,N-dimethylaniline, ethyl benzoate, 1-methylnaphthalene, 2-methylnaphthalene, N-methylpyrrolidinone, dioxane, 4-isopropylbiphenyl, phenyl ether, pyridine, 1,8-octanedithiol, nitrobenzene, 1-chloronaphthalene, p-xylene, m-xylene, o-xylene or mixture of o-, m-, and p-isomers.

The OPV device can be of any OPV device type known from the literature (see e.g. Waldauf et al., *Appl. Phys. Lett.*, 2006, 89, 233517).

A first preferred OPV device according to the invention comprises the following layers (in the sequence from bottom to top):
 optionally a substrate,
 a high work function electrode, preferably comprising a metal oxide, like for example ITO, serving as anode or a conducting grid
 an optional conducting polymer layer or hole transport layer, preferably comprising an organic polymer or polymer blend, for example PEDOT:PSS (poly(3,4-ethylenedioxythiophene):poly(styrene-sulfonate), substituted triaryl amine derivatives, for example, TBD (N,N'-dyphenyl-N—N'-bis(3-methylphenyl)-1,1'biphenyl-4,4'-diamine) or NBD (N,N'-dyphenyl-N—N'-bis(1-napthylphenyl)-1,1'biphenyl-4,4'-diamine),
 a layer, also referred to as "photoactive layer", comprising a p-type and an n-type organic semiconductor, which can exist for example as a p-type/n-type bilayer or as distinct p-type and n-type layers, or as blend or p-type and n-type semiconductor, forming a BHJ,
 optionally a layer having electron transport properties, for example comprising LiF, $TiO_x$, $ZnO_x$, PFN, a poly(ethyleneimine) or crosslinked nitrogen containing compound derivatives or a phenanthroline derivatives
 a low work function electrode, preferably comprising a metal like for example aluminum, serving as cathode, wherein at least one of the electrodes, preferably the anode, is at least partially transparent to visible light, and
 wherein the n-type semiconductor is a fullerene derivative of this invention.

A second preferred OPV device according to the invention is an inverted OPV device and comprises the following layers (in the sequence from bottom to top):
 optionally a substrate,
 a high work function metal or metal oxide electrode, comprising for example ITO, serving as cathode, or a conducting grid
 a layer having hole blocking properties, preferably comprising a metal oxide like $TiO_x$ or $ZnO_x$, or comprising an organic compound such as polymer like poly(ethyleneimine) or crosslinked nitrogen containing compound derivatives or phenanthroline derivatives,
 a photoactive layer comprising a p-type and an n-type organic semiconductor, situated between the electrodes, which can exist for example as a p-type/n-type bilayer or as distinct p-type and n-type layers, or as blend or p-type and n-type semiconductor, forming a BHJ,
 an optional conducting polymer layer or hole transport layer, preferably comprising an organic polymer or polymer blend, for example of PEDOT:PSS or substituted triaryl amine derivatives, for example, TBD or NBD,
 an electrode comprising a high work function metal like for example silver, serving as anode,
 wherein at least one of the electrodes, preferably the cathode, is at least partially transparent to visible light, and
 wherein the n-type semiconductor is a fullerene derivative of this invention.

In the OPV devices of the present invention the p-type and n-type semiconductor materials are preferably selected from the materials, like the polymer/fullerene systems, as described above When the photoactive layer is deposited on the substrate, it forms a BHJ that phase separates at nanoscale level. For discussion on nanoscale phase separation see Dennler et al, *Proceedings of the IEEE*, 2005, 93 (8), 1429 or Hoppe et al, *Adv. Func. Mater,* 2004, 14(10), 1005. An optional annealing step may be then necessary to optimize blend morphology and consequently OPV device performance.

Another method to optimize device performance is to prepare formulations for the fabrication of OPV(BHJ) devices that may include additives with variable boiling points to promote phase separation in the right way. 1,8-Octanedithiol, 1,8-diiodooctane, nitrobenzene, 1-chloronaphthalene, N,N-dimethylformamide, dimethylacetamide, dimethylsulfoxide and other additives have been used to obtain high-efficiency solar cells. Examples are disclosed in J. Peet, et al, *Nat. Mater.,* 2007, 6, 497 or Fréchet et al. *J. Am. Chem. Soc.,* 2010, 132, 7595-7597.

As further illustrated in the non-limiting working examples, photovoltaic devices can be prepared which have a power conversion efficiency (PCE) of, for example, at least 2.5%, or at least 3.0%, or at least 4.0%, or at least 5.0%. While there is no particular upper limit on the PCE, the PCE can be, for example, less than 20%, or less than 15%, or less than 10%.

Another preferred embodiment of the present invention relates to the use of a fullerene derivative or fullerene composition according to the present invention as dye, hole transport layer, hole blocking layer, electron transport layer and/or electron blocking layer in a DSSC or a perovskite-based solar cells, and to a DSSC or perovskite-based solar cells comprising a compound composition or polymer blend according to the present invention.

DSSCs and perovskite-based solar cells can be manufactured as described in the literature, for example in Chem. Rev. 2010, 110, 6595-6663, Angew. Chem. Int. Ed. 2014, 53, 2-15 or in WO2013171520A1.

The fullerene derivatives and fullerene compositions of the present invention can also be used as dye or pigment in other applications, for example as an ink dye, laser dye, fluorescent marker, solvent dye, food dye, contrast dye or pigment in coloring paints, inks, plastics, fabrics, cosmetics, food and other materials.

The fullerene derivatives, fullerene compositions and semiconducting layers of the present invention are also suitable for use as n-type semiconductor in other electronic devices or device components, for example in the semiconducting channel of an OFET device, or in the buffer layer, electron transport layer (ETL) or hole blocking layer (HBL) of an OLED or OPV device.

Accordingly, the invention also provides an OFET comprising a gate electrode, an insulating (or gate insulator) layer, a source electrode, a drain electrode and an organic semiconducting channel connecting the source and drain electrodes, wherein the organic semiconducting channel comprises a fullerene derivative of this invention, a fullerene composition or an organic semiconducting layer according to the present invention as n-type semiconductor. Other features of the OFET are well known to those skilled in the art.

OFETs where an OSC material is arranged as a thin film between a gate dielectric and a drain and a source electrode, are generally known, and are described for example in U.S. Pat. Nos. 5,892,244, 5,998,804, 6,723,394 and in the references cited in the background section. Due to the advantages, like low cost production using the solubility properties of the compounds according to the invention and thus the processability of large surfaces, preferred applications of these FETs are such as integrated circuitry, TFT displays and security applications.

The gate, source and drain electrodes and the insulating and semiconducting layer in the OFET device may be arranged in any sequence, provided that the source and drain electrode are separated from the gate electrode by the insulating layer, the gate electrode and the semiconductor layer both contact the insulating layer, and the source electrode and the drain electrode both contact the semiconducting layer.

An OFET device according to the present invention preferably comprises:
 a source electrode,
 a drain electrode,
 a gate electrode,
 a semiconducting layer,
 one or more gate insulator layers,
 optionally a substrate.
wherein the semiconductor layer comprises a fullerene derivative of this invention or a fullerene composition as described above and below.

The OFET device can be a top gate device or a bottom gate device. Suitable structures and manufacturing methods of an OFET device are known to the skilled in the art and are described in the literature, for example in US 2007/0102696 A1.

The gate insulator layer preferably comprises a fluoropolymer, like e.g. the commercially available Cytop 809M® or Cytop 107M® (from Asahi Glass). Preferably the gate insulator layer is deposited, e.g. by spin-coating, doctor blading, wire bar coating, spray or dip coating or other known methods, from a formulation comprising an insulator material and one or more solvents with one or more fluoro atoms (fluorosolvents), preferably a perfluorosolvent. A suitable perfluorosolvent is e.g. FC75® (available from Acros, catalogue number 12380). Other suitable fluoropolymers and fluorosolvents are known in prior art, like for example the perfluoropolymers Teflon AF® 1600 or 2400 (from DuPont) or Fluoropel® (from Cytonix) or the perfluorosolvent FC 43® (Acros, No. 12377). Especially preferred are organic dielectric materials having a low permittivity (or dielectric contant) from 1.0 to 5.0, very preferably from 1.8 to 4.0 ("low k materials"), as disclosed for example in US 2007/0102696 A1 or U.S. Pat. No. 7,095,044.

In security applications, OFETs and other devices with semiconducting materials according to the present invention, like transistors or diodes, can be used for RFID tags or security markings to authenticate and prevent counterfeiting of documents of value like banknotes, credit cards or ID cards, national ID documents, licenses or any product with monetary value, like stamps, tickets, shares, cheques etc.

Alternatively, the fullerene derivatives, fullerene compositions, and semiconducting layers according to the invention can be used in OLEDs, for example in the buffer layer, ETL or HBL of an OLED. The OLED device can be used for example as the active display layer in a flat panel display device, or as the backlight of a flat panel display like for example a liquid crystal display. Common OLEDs are realized using multilayer structures. An emission layer is generally sandwiched between one or more electron-transport and/or hole-transport layers. By applying an electric voltage electrons and holes as charge carriers move towards the emission layer where their recombination leads to the excitation and hence luminescence of the lumophor units contained in the emission layer.

The fullerene derivatives, fullerene composition or semiconducting layer according to the present invention may be employed in one or more of the ETL, HBL or buffer layer, especially their water-soluble derivatives (for example with polar or ionic side groups) or ionically doped forms. The processing of such layers, comprising a semiconductor material of the present invention, for the use in OLEDs is generally known by a person skilled in the art, see, e.g., Müller et al, *Synth. Metals*, 2000, 111-112, 31-34, Alcala, *J. Appl. Phys.*, 2000, 88, 7124-7128, O'Malley et al, *Adv. Energy Mater.* 2012, 2, 82-86 and the literature cited therein.

According to another use, the fullerene derivatives, fullerene compositions, and materials according to this invention, especially those showing photoluminescent properties, may be employed as materials of light sources, e.g. in display devices, as described in EP 0 889 350 A1 or by C. Weder et al., *Science*, 1998, 279, 835-837.

A further aspect of the invention relates to both the oxidised and reduced form of a fullerene derivative according to this invention. Either loss or gain of electrons results in formation of a highly delocalised ionic form, which is of high conductivity. This can occur on exposure to common dopants. Suitable dopants and methods of doping are known to those skilled in the art, e.g. from EP 0 528 662, U.S. Pat. No. 5,198,153 or WO 96/21659.

The doping process typically implies treatment of the semiconductor material with an oxidating or reducing agent in a redox reaction to form delocalised ionic centres in the material, with the corresponding counterions derived from the applied dopants. Suitable doping methods comprise for example exposure to a doping vapor in the atmospheric pressure or at a reduced pressure, electrochemical doping in a solution containing a dopant, bringing a dopant into contact with the semiconductor material to be thermally diffused, and ion-implantantion of the dopant into the semiconductor material.

When electrons are used as carriers, suitable dopants are for example halogens (e.g., $I_2$, $Cl_2$, $Br_2$, ICl, $ICl_3$, IBr and IF), Lewis acids (e.g., $PF_5$, $AsF_5$, $SbF_5$, $BF_3$, $BCl_3$, $SbCl_5$, $BBr_3$ and $SO_3$), protonic acids, organic acids, or amino acids (e.g., HF, HCl, $HNO_3$, $H_2SO_4$, $HClO_4$, $FSO_3H$ and $ClSO_3H$), transition metal compounds (e.g., $FeCl_3$, FeOCl, $Fe(ClO_4)_3$, $Fe(4\text{-}CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid), anions (e.g., $Cl^-$, $Br^-$, $I^-$, $I_3^-$, $HSO_4^-$, $SO_4^{2-}$, $NO_3^-$, $ClO_4^-$, $BF_4^-$, $PF_6^-$, $AsF_6^-$, $SbF_6^-$, $FeCl_4^-$, $Fe(CN)_6^{3-}$, and anions of various sulfonic acids, such as aryl-$SO_3^-$). When holes are used as carriers, examples of dopants are cations (e.g., $H^+$, $Li^+$, $Na^+$, $K^+$, $Rb^+$ and $Cs^+$), alkali metals (e.g., Li, Na, K, Rb, and Cs), alkaline-earth metals (e.g., Ca, Sr, and Ba), $O_2$, $XeOF_4$, $(NO_2^+)(SbF_6^-)$, $(NO_2^+)(SbCl_6^-)$, $(NO_2^+)(BF_4^-)$, $AgClO_4$, $H_2IrCl_6$, $La(NO_3)_3.6H_2O$, $FSO_2OOSO_2F$, Eu, acetylcholine, $R_4N^+$, (R is an alkyl group), $R_4P^+$ (R is an alkyl group), $R_6As^+$ (R is an alkyl group), and $R_3S^+$ (R is an alkyl group).

The conducting form of a fullerene derivative of the present invention can be used as an organic "metal" in applications including, but not limited to, charge injection layers and ITO planarising layers in OLED applications, films for flat panel displays and touch screens, antistatic films, printed conductive substrates, patterns or tracts in electronic applications such as printed circuit boards and condensers.

According to another use, the fullerene derivatives and fullerene compositions according to the present invention can be used alone or together with other materials in or as alignment layers in LCD or OLED devices, as described for example in US 2003/0021913. The use of charge transport compounds according to the present invention can increase the electrical conductivity of the alignment layer. When used in an LCD, this increased electrical conductivity can reduce adverse residual dc effects in the switchable LCD cell and suppress image sticking or, for example in ferroelectric LCDs, reduce the residual charge produced by the switching of the spontaneous polarisation charge of the ferroelectric LCs. When used in an OLED device comprising a light emitting material provided onto the alignment layer, this increased electrical conductivity can enhance the electroluminescence of the light emitting material. The fullerene derivatives, fullerene compositions, and materials according to the present invention may also be combined with photoisomerisable compounds and/or chromophores for use in or as photoalignment layers, as described in US 2003/0021913 A1.

According to another use the fullerene derivatives, fullerene compositions, and materials according to the present invention, especially their water-soluble derivatives (for example with polar or ionic side groups) or ionically doped forms, can be employed as chemical sensors or materials for detecting and discriminating DNA sequences. Such uses are described for example in L. Chen, D. W. McBranch, H. Wang, R. Helgeson, F. Wudl and D. G. Whitten, *Proc. Natl. Acad. Sci. U.S.A.*, 1999, 96, 12287; D. Wang, X. Gong, P. S. Heeger, F. Rininsland, G. C. Bazan and A. J. Heeger, *Proc. Natl. Acad. Sci. U.S.A.*, 2002, 99, 49; N. DiCesare, M. R. Pinot, K. S. Schanze and J. R. Lakowicz, *Langmuir*, 2002, 18, 7785; D. T. McQuade, A. E. Pullen, T. M. Swager, *Chem. Rev.*, 2000, 100, 2537.

Unless the context clearly indicates otherwise, as used herein plural forms of the terms herein are to be construed as including the singular form and vice versa.

Throughout the description and claims of this specification, the words "comprise" and "contain" and variations of the words, for example "comprising" and "comprises", mean "including but not limited to", and are not intended to (and do not) exclude other components.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

Above and below, unless stated otherwise percentages are percent by weight and temperatures are given in ° C. The values of the dielectric constant ε ("permittivity") refer to values taken at 20° C. and 1,000 Hz.

The invention will now be described in more detail by reference to the following examples, which are illustrative only and do not limit the scope of the invention.

A) Compound Examples

Comparative Example 1

Fullerene C1

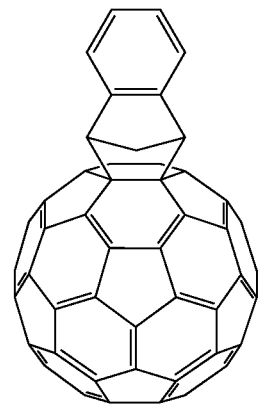

Fullerene C1 (ICMA-C60) and its preparation are disclosed in U.S. Pat. No. 8,217,260 B2.

Example 1

Fullerene 1

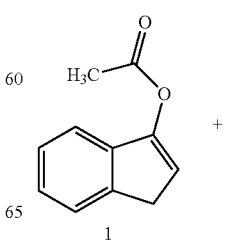

1

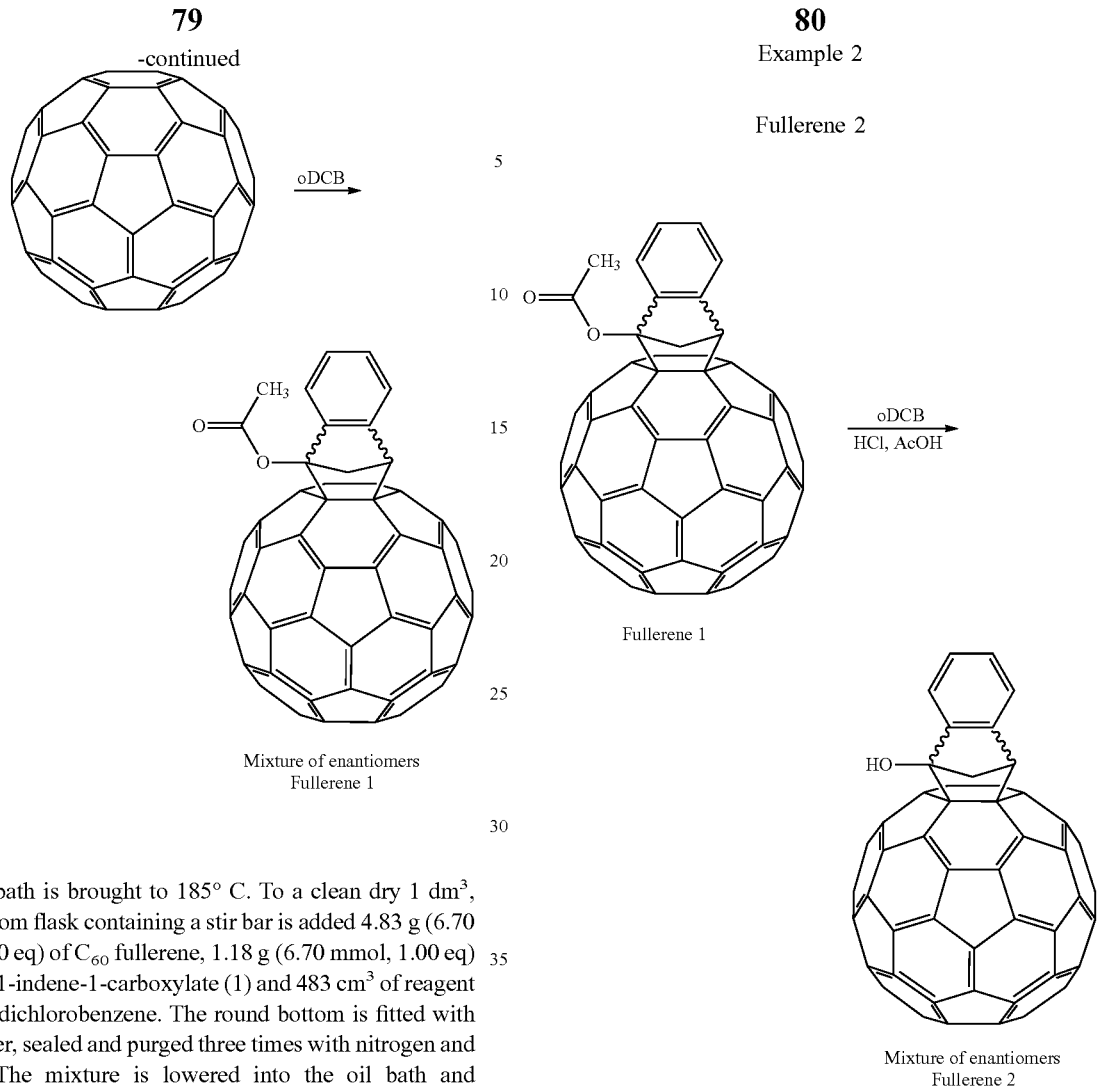

Example 2

Fullerene 2

An oil bath is brought to 185° C. To a clean dry 1 dm³, round bottom flask containing a stir bar is added 4.83 g (6.70 mmol, 1.00 eq) of $C_{60}$ fullerene, 1.18 g (6.70 mmol, 1.00 eq) of methyl 1-indene-1-carboxylate (1) and 483 cm³ of reagent grade 1,2-dichlorobenzene. The round bottom is fitted with a condenser, sealed and purged three times with nitrogen and vacuum. The mixture is lowered into the oil bath and allowed to reflux for 3 days. 1,2-Dichlorobenzene is removed by rotary evaporation, 100 cm³ of toluene is added, the mixture is sonicated and solid $C_{60}$ fullerene (3.72 g) is separated by filtration. The process is repeated in a smaller amount of toluene to obtain a second portion of $C_{60}$ fullerene (0.70 g). The crude material is evaporated onto silica, loaded into a silica column and purified using silica gel chromatography with 1:1 toluene:cyclohexane followed by 100% toluene as the eluent. Product fractions of relatively high purity are collected, concentrated into 50 cm³ of toluene and subjected to preparative intermediate pressure liquid chromatography using a column with Cosmosil Buckyprep material as the stationary phase (from. Nacalai Tesque; pyrenylpropyl group bonded silica) and toluene as the mobile phase. Fractions containing product of relatively high purity are combined and solvent removed using rotary evaporation. The sample is left in an oven overnight at 70° C. under reduced pressure to remove residual solvent. The product (Fullerene 1) is isolated (425 mg, 6.75% yield) as a brown crystalline solid. Purity is confirmed at 99.80% by analytical HPLC using a column with Cosmosil Buckyprep material as the stationary phase (from Nacalai Tesque; pyrenylpropyl group bonded silica) and toluene as the mobile phase.

An oil bath is brought to 110° C. To a clean dry 250 cm³ round bottom with a stir bar is added 658 mg of Fullerene 1, 32.9 cm³ of o-dichlorobenzene, 82.3 cm³ of glacial acetic acid, and 32.9 cm³ of concentrated hydrochloric acid. The flask is then fitted with a condenser and rubber stopper, purged three times with nitrogen and vacuum, dropped into the bath at 110° C. and stirred vigorously for 4 days. The reaction is transferred to a separatory funnel. 250 cm³ of toluene and 250 cm³ of water are added. The mixture is shaken well and allowed to separate. The water layer is removed and the toluene layer is washed two more times with the same portion of water. The toluene layer is then dried with magnesium sulfate and filtered. All solvent is removed by rotary evaporation. The residue is redissolved in toluene and purified by silica gel chromatography (toluene as eluent). This initial purification is followed by intermediate pressure liquid chromatography using a column with Cosmosil buckyprep material as the stationary phase (from Nacalai Tesque; pyrenylpropyl bonded silica) and toluene as the mobile phase. Fractions containing pure product are combined and solvent removed using rotary evaporation. The sample is left in an oven overnight at 70° C. under reduced pressure to remove residual solvent. The product (Fullerene 2) is isolated (397 mg, 63.3%) as a brown crystalline solid.

Example 3

Fullerene 3

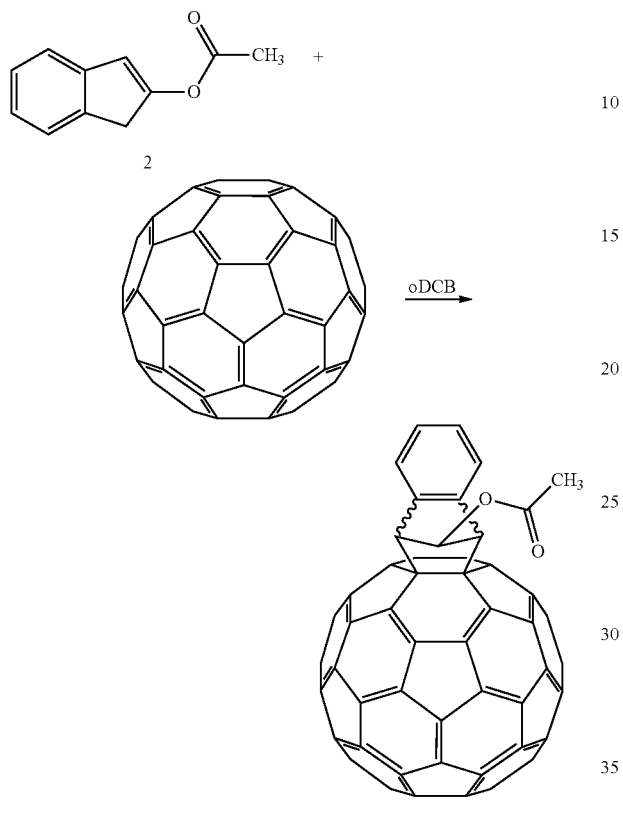

Mixture of isomers
Fullerene 3

An oil bath is brought to 200° C. To a clean dry 0.5 dm³ pressure vessel containing a stir bar is added 3.75 g (5.20 mmol, 1.00 eq) of $C_{60}$ fullerene, 4.58 g (26.00 mmol, 5.00 eq) of methyl indene-2-carboxylate (2) and 375 cm³ of reagent grade 1,2-dichlorobenzene. The pressure vessel is purged three times with nitrogen and vacuum, sealed, lowered into the oil bath (with a blast shield placed in front of the reaction) and allowed to stir for 3-5 days until desired conversion is achieved (22.9% by HPLC in this case). 1,2-Dichlorobenzene is removed by rotary evaporation, 100 cm³ of toluene is added, the mixture is sonicated and solid $C_{60}$ fullerene (2.32 g) is separated by filtration. The total toluene filtrate is collected and reduced to ~75 dm³ by rotary evaporation and loaded onto a silica column (5 cm diameter, 0.5 meters long) and purified using silica gel chromatography with toluene as the eluent. Product fractions of relatively high purity are collected, concentrated into 50 cm³ of toluene and subjected to preparative intermediate pressure liquid chromatography using a column with Cosmosil Buckyprep material as the stationary phase (from Nacalai Tesque; pyrenylpropyl group bonded silica) and toluene as the mobile phase. Fractions containing product of relatively high purity are combined and solvent removed using rotary evaporation until desired product precipitates. Desired product is then redissolved in toluene and the toluene is again removed using rotary evaporation until desired product precipitates. The solid is filtered again and left in an oven overnight at 70° C. under reduced pressure to remove residual solvent. The product (Fullerene 3) is isolated (265 mg, 4.74% yield) as a brown crystalline solid. Purity is confirmed at 99.0% by analytical HPLC using a column with Cosmosil Buckyprep material as the stationary phase (from Nacalai Tesque; pyrenylpropyl group bonded silica) and toluene as the mobile phase.

Example 4

Fullerene 4

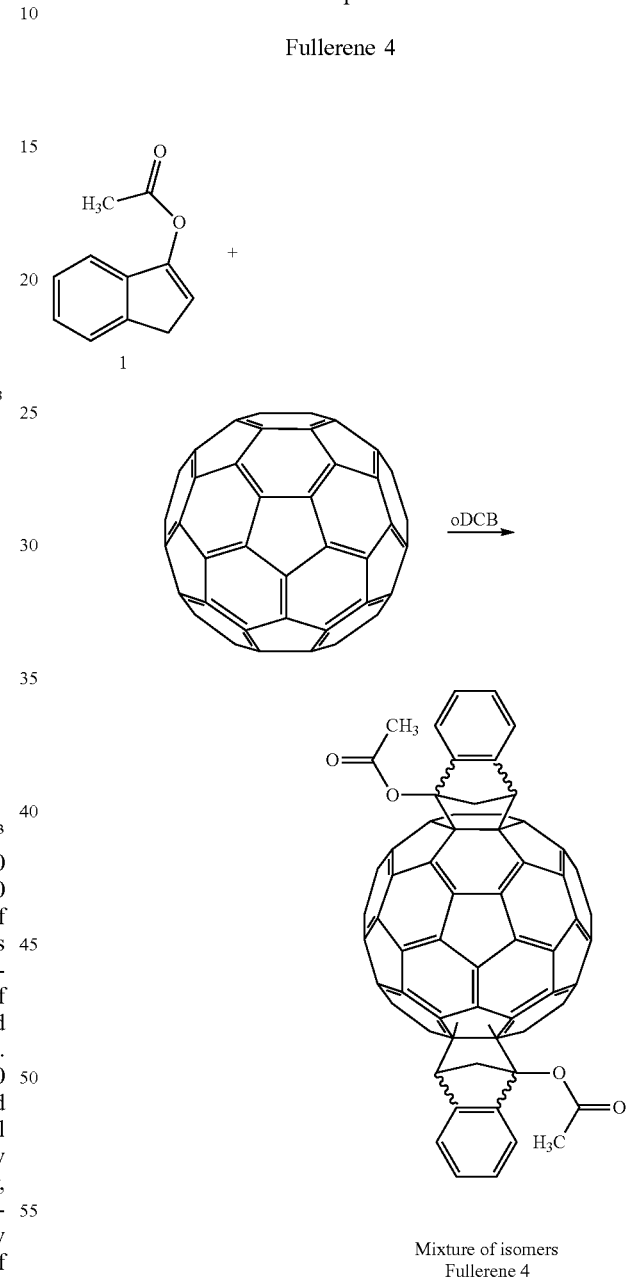

Mixture of isomers
Fullerene 4

An oil bath is brought to 185° C. To a clean dry 2 dm³, round bottom flask containing a stir bar is added 10.55 g (14.64 mmol, 1.00 eq) of $C_{60}$ fullerene, 12.9 g (73.21 mmol, 5.00 eq) of methyl 1-indene-1-carboxylate (1) and 1.055 dm³ of reagent grade 1,2-dichlorobenzene. The round bottom is fitted with a condenser, sealed and purged three times with nitrogen and vacuum. The mixture is lowered into the oil bath and allowed to reflux for 3.5 days. 1,2-Dichlorobenzene is removed by rotary evaporation, 100 cm³ of toluene is added, the mixture is sonicated and mainly solid C$_{60}$ fullerene (5 g) is separated by filtration. The filtrate is diluted to 300 cm³ of 1:1 toluene:cyclohexane, loaded into a silica column and purified using silica gel chromatography with 1:1 toluene:cyclohexane followed by 100% toluene as the eluent. Product fractions are collected, concentrated to a small amount of toluene and the fullerenic material is precipitated by addition to hexane. The filtrand is redissolved in 20 cm³ toluene and subjected to preparative intermediate pressure liquid chromatography using a column with Cosmosil Buckyprep material as the stationary phase (from Nacalai Tesque; pyrenylpropyl group bonded silica) and toluene as the mobile phase. Fractions containing product of relatively high purity are combined and solvent removed using rotary evaporation. The sample is left in an oven overnight at 70° C. under reduced pressure to remove residual solvent. The product (Fullerene 4) is isolated (299.6 mg, 1.9% yield) as a brown crystalline solid. Purity is confirmed at 99.98% by analytical HPLC using a column with Cosmosil Buckyprep material as the stationary phase (from Nacalai Tesque; pyrenylpropyl group bonded silica) and toluene as the mobile phase.

Example 5

Fullerene 5

An oil bath is brought to 185° C. To a clean dry 250 cm³, round bottom flask containing a stir bar is added 1 g (1.19 mmol, 1.00 eq) of C$_{70}$ fullerene, 1.05 g (5.95 mmol, 5.00 eq) of methyl 1-indene-1-carboxylate (1) and 100 cm³ of reagent grade 1,2-dichlorobenzene. The round bottom is fitted with a condenser, sealed and purged three times with nitrogen and vacuum. The mixture is lowered into the oil bath and allowed to reflux for 3 days. 1,2-Dichlorobenzene is removed by rotary evaporation, 1:1 toluene:cyclohexane is added, and the crude material is loaded into a silica column and purified using silica gel chromatography with 1:1 toluene:cyclohexane as the eluent. Product fractions of relatively high purity are collected, concentrated into 25 cm³ of toluene and subjected to preparative intermediate pressure liquid chromatography using a column with Cosmosil Buckyprep material as the stationary phase (from Nacalai Tesque; pyrenylpropyl group bonded silica) and toluene as the mobile phase. Fractions containing product of relatively high purity are combined and much of the solvent is removed using rotary evaporation. Hexane is added to precipitate the desired product which is filtered. The filtrand is left in an oven overnight at 70° C. under reduced pressure to remove residual solvent. The product (Fullerene 5) is isolated (473 mg, 39.16% yield) as a brown crystalline solid. Purity is confirmed at 99.90% by analytical HPLC using a column with Cosmosil Buckyprep material as the stationary phase (from Nacalai Tesque; pyrenylpropyl group bonded silica) and toluene as the mobile phase.

Example 6

Fullerene 6

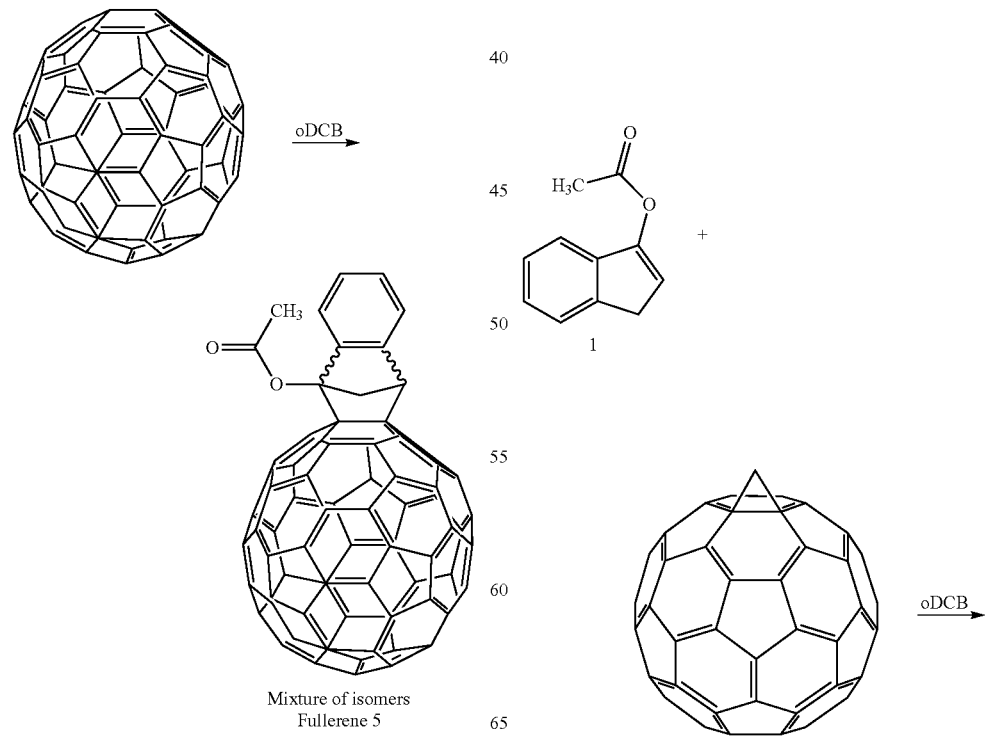

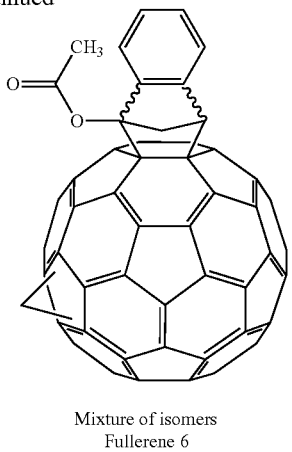

Mixture of isomers
Fullerene 6

A heating mantle and sand bath are brought to 190° C. To a clean dry, two neck, 250 cm³ round bottom flask containing a stir bar is added 0.82 g (1.12 mmol, 1.00 eq) of $C_{61}F_{12}$ (methano[$C_{60}$]fullerene), 0.983 g (5.58 mmol, 5.00 eq) of 1-indene-1-carboxylate (1) and 82 cm³ of reagent grade 1,2-dichlorobenzene. The round bottom is fitted with a condenser, sealed and purged three times with nitrogen and vacuum. The mixture is lowered into the sand bath and allowed to reflux for 2 days. Another 0.44 g (2.50 mmol, 2.24 eq) of 1-indene-1-carboxylate (1) is added by syringe in a small amount of 1,2-dichlorobenzene and the reaction is allowed to reflux for one additional day. 1,2-Dichlorobenzene is removed by rotary evaporation, 1 dm³ of 1:1 toluene:cyclohexane is added, and the mixture is purified using silica gel chromatography with 1:1 toluene:cyclohexane followed by 100% toluene as the eluent. Product fractions of relatively high purity are collected, concentrated, and subjected to preparative intermediate pressure liquid chromatography using a column with Cosmosil Buckyprep material as the stationary phase (from Nacalai Tesque; pyrenylpropyl group bonded silica) and toluene as the mobile phase. Fractions containing product of relatively high purity are combined and the majority of the solvent is removed using rotary evaporation. The product is then precipitated by addition to methanol and the solid is isolated by filtration. The sample is left in an oven overnight at 70° C. under reduced pressure to remove residual solvent. The product (Fullerene 6) is isolated (213 mg, 21.0% yield) as a brown crystalline solid. Purity is confirmed at 99.84% by analytical HPLC using a column with Cosmosil Buckyprep material as the stationary phase (from Nacalai Tesque; pyrenylpropyl group bonded silica) and toluene as the mobile phase.

B) Use Examples
Bulk Heterojunction Organic Photovoltaic Devices (OPVs) For Fullerene C1 (ICMA), PCBM C60 And Fullerenes 1-6

Organic photovoltaic (OPV) devices are fabricated on pre-patterned ITO-glass substrates (13 Ω/sq.) purchased from LUMTEC Corporation. Substrates are cleaned using common solvents (acetone, iso-propanol, deionized-water) in an ultrasonic bath. A conducting polymer poly(ethylene dioxythiophene) doped with poly(styrene sulfonic acid) [Clevios VPAI 4083 (H. C. Starck)] is mixed in a 1:1 ratio with deionized-water. This solution is filtered using a 0.45 μm filter before spin-coating to achieve a thickness of 20 nm. Substrates are exposed to ozone prior to the spin-coating process to ensure good wetting properties. Films are then annealed at 140° C. for 30 minutes in a nitrogen atmosphere where they are kept for the remainder of the process. Active material solutions (i.e. polymer+fullerene) are prepared to fully dissolve the solutes at a 30 mg·cm⁻³ solution concentration in 1,2-dichlorobenzene (oDCB) or in 2,4-dimethylanisole (DMA)+1% 1,8-diiodooctane (DIO). Thin films are either spin-coated or blade-coated in a nitrogen atmosphere to achieve active layer thicknesses between 50 and 500 nm as measured using a profilometer. A short drying period follows to ensure removal of any residual solvent.

Typically, blade-coated films are dried at 70° C. for 2 minutes on a hotplate. For the last step of the device fabrication, Ca (30 nm)/Al (100 nm) cathodes are thermally evaporated through a shadow mask to define the cells. Current-voltage characteristics are measured using a Keithley 2400 SMU while the solar cells are illuminated by a Newport Solar Simulator at 100 mW·cm⁻² white light. The solar simulator is equipped with AM1.5G filters. The illumination intensity is calibrated using a Si photodiode. All the device preparation and characterization is done in a dry-nitrogen atmosphere.

Power conversion efficiency is calculated using the following expression $$\eta = \frac{V_{oc} \times J_{sc} \times FF}{P_{in}}$$

where FF is defined as $$FF = \frac{V_{max} \times J_{max}}{V_{oc} \times J_{sc}}$$

OPV device characteristics for a blend of Polymer 1 and fullerene coated from an o-dichlorobenzene or DMA+DIO solution are shown in Table 1.

Polymer 1

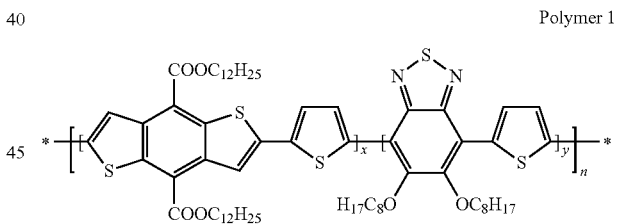

Polymer 1 and its preparation are disclosed in WO 2011/131280.

The photovoltaic cell characteristics are summarized in Table 1 below.

TABLE 1

Photovoltaic cell characteristics.

| Fullerene | Polymer | Ratio Polymer:Fullerene | Solvent | Voc mV | Jsc mA·cm⁻² | FF % | PCE % |
|---|---|---|---|---|---|---|---|
| PCBM-C60 | 1 | 1.00:1.50 | oDCB | 773 | −11.9 | 68 | 6.3 |
| C1 | 1 | 1.00:1.50 | oDCB | 715 | −0.8 | 30 | 0.2 |
| C1 | 1 | 1.00:1.50 | DMA + DIO | 765 | −12.3 | 60 | 5.7 |
| 1 | 1 | 1.00:2.00 | oDCB | 738 | −13.1 | 57 | 5.5 |
| 1 | 1 | 1.00:1.50 | DMA + DIO | 764 | −10.0 | 62 | 4.7 |
| 2 | 1 | 1.00:2.00 | oDCB | 753 | −6.5 | 61 | 3.0 |

TABLE 1-continued

Photovoltaic cell characteristics.

| Fullerene | Polymer | Ratio Polymer:Fullerene | Solvent | Voc mV | Jsc mA·cm⁻² | FF % | PCE % |
|---|---|---|---|---|---|---|---|
| 2 | 1 | 1.00:2.00 | DMA + DIO | 754 | −4.0 | 45 | 1.4 |
| 4 | 1 | 1.00:2.00 | oDCB | 905 | −3.8 | 49 | 1.7 |
| 4 | 1 | 1.00:2.00 | DMA + DIO | 874 | −4.1 | 45 | 1.6 |
| 5 | 1 | 1.00:2.00 | oDCB | 792 | −6.5 | 44 | 2.2 |
| 5 | 1 | 1.00:2.00 | DMA + DIO | 727 | −1.1 | 30 | 0.3 |
| 6 | 1 | 1.00:2.00 | oDCB | 886 | −4.8 | 47 | 2.0 |
| 6 | 1 | 1.00:2.00 | DMA + DIO | 863 | −6.8 | 43 | 2.5 |

It can be seen that the BHJ containing phenyl substituted indene Fullerenes 1 and 2 according to the invention shows a large increase in PCE when deposited from a chlorinated solvent, compared to the BHJ containing Fullerene C1 of prior art. It can also be seen that the BHJ containing phenyl substituted indene Fullerenes 4, 5 and 6 also show improvements in PCE when deposited from a chlorinated solvent, compared to the BHJ containing Fullerene C1 of prior art.

Figure 3:
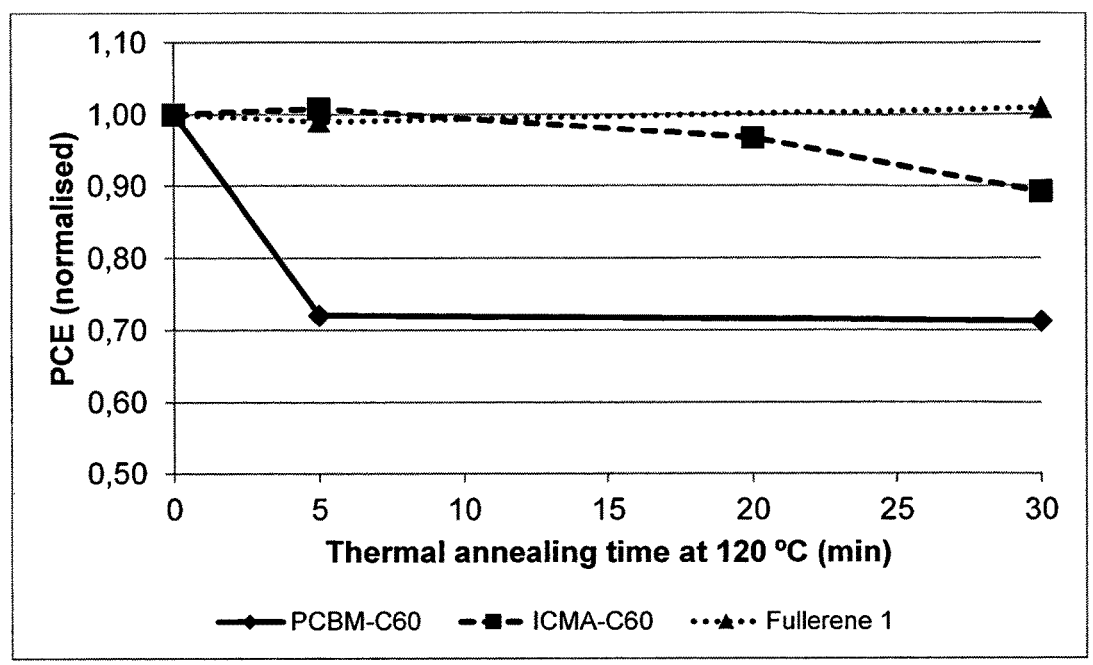
FIG. 3 shows the thermal stability of OPV devices according to Example 1 and Comparison Examples 1 and 2.

FIG. 3 shows the normalised PCE as function of the device annealing time at 120° C. It can be seen that the BHJ containing substituted indene Fullerene 1 according to the invention shows an increase in device thermal stability, when deposited from a non-chlorinated, over Fullerene C1 (ICMA-C60) and PCBM-C60 as disclosed in prior art.

The invention claimed is:

1. A compound of formula I

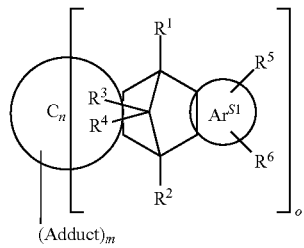

wherein $C_n$ denotes a fullerene composed of n carbon atoms, optionally with one or more atoms trapped inside, Adduct is a secondary adduct, or a combination of secondary adducts, appended to the fullerene $C_n$ with any connectivity, m is 0, an integer>1, or a non-integer>0, o is an integer≥1, $Ar^{S1}$ denotes an aryl or heteroaryl group with 5 to 20, preferably 5 to 15, ring atoms, which is mono- or polycyclic, $R^1$ to $R^6$ denote, independently of each other, H, halogen, CN, $R^7$, $R^8$ or $R^9$, $R^7$ denotes, on each occurrence identically or differently, a saturated or unsaturated, non-aromatic carbo- or heterocyclic group, or an aryl, heteroaryl, aryloxy or heteroaryloxy group, wherein each of the aforementioned groups has 3 to 20 ring atoms, is mono- or polycyclic, does optionally contain fused rings, and is optionally substituted by one or more halogen atoms or CN groups, or by one or more identical or different groups $R^8$ or $R^9$, $R^8$ denotes, on each occurrence identically or differently, an alkyl group with 1 to 30 C atoms, which is straight-chain, branched or cyclic, and in which one or more $CH_2$ groups are optionally replaced by —O—, —S—, —C(=O)—, —C(=S)—, —C(=O)—O—, —O—C(=O)—, —$NR^0$—, —C(=O)$NR^0$—, —$NR^0$—C(=O)—, —$SiR^0R^{00}$—, —$CF_2$—, —$CHR^0$=$CR^{00}$—, —$CY^1$=$CY^2$— or —C≡C— in such a manner that O and/or S atoms are not linked directly to one another, and in which one or more H atoms are optionally replaced by F, Cl, Br, I or CN, $R^9$ denotes, on each occurrence identically or differently, a straight-chain, branched or cyclic alkyl group with 1 to 50, preferably 2 to 50, more preferably 2 to 25, most preferably 2 to 12, C atoms, in which one or more $CH_2$ or $CH_3$ groups are replaced by a cationic or anionic group, $Y^1$ and $Y^2$ denote, independently of each other, H, F, Cl or CN, $R^0$ and $R^{00}$ denote, independently of each other, H or an optionally substituted carbyl or hydrocarbyl group having 1 to 40 C atoms, with the provisos that a) at least one of $R^1$, $R^2$, $R^3$ and $R^4$ is different from H, and b) if n=70, then $R^1$ is different from —C(=O)—O—$CH_3$ if $R^2$ is H, and $R^2$ is different from —C(=O)—O—$CH_3$ if $R^1$ is H, and wherein when $R^1$, $R^2$, $R^3$ and $R^4$ are different from H, they are selected from the following formulae

(P-RS-1)

(P-RS-2)

(P-RS-3)

(P-RS-4)

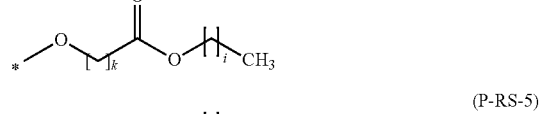
(P-RS-5)

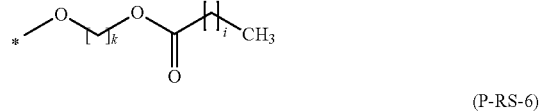
(P-RS-6)

(P-RS-7)

wherein $Ar^{S2}$ denotes $R^7$ or has one of the meanings of $Ar^{S1}$, i is 0 or an integer from 1 to 9, k is 0 or an integer from 1 to 9.

2. The compound of claim 1, wherein n is 60 or 70.

3. The compound of claim 1, wherein $C_n$, is a carbon based fullerene or an endohedral fullerene.

4. The compound of claim 3, wherein $C_n$, is selected from $(C_{60-Ih})$[5,6]fullerene, $(C_{70-D5h})$[5,6]fullerene, $(C_{76-D2*})$[5,6]fullerene, $(C_{84-D2*})$[5,6]fullerene, $(C_{84-D2d})$[5,6]fullerene, La@$C_{60}$, La@$C_{82}$, Y@$C_{82}$, $Sc_3N$@$C_{80}$, $Y_3N$@$C_{80}$, $Sc_3C_2$@$C_{80}$ or a mixture of two or more of the aforementioned fullerenes.

5. The compound according to claim 1, wherein m is 0 and o is 1.

6. The compound according to claim 1, wherein the fullerene $C_n$ is substituted at a [6,6] and/or [5,6] bond.

7. The compound according to claim 1, wherein $Ar^{S1}$ is a benzene, thiophene or naphthalene group that is optionally substituted with one or more groups $R^5$.

8. The compound according to claim 1, wherein $R^2$, $R^3$ and $R^4$ are H and $R^1$ is selected from formulae P-RS-1 or P-RS-7 as defined in claim 1, wherein k is 0.

9. The compound according to claim 1, wherein $R^3$ and $R^4$ are H.

10. The compound according to claim 1, wherein one of $R^1$ and $R^2$ is H and the other is different from H.

11. The compound according to claim 1, wherein $R^2$, $R^3$ and $R^4$ are H and $R^1$ is selected from formulae P-RS-1 to P-RS-7 as defined in claim 1, preferably from formula P-RS-1 or P-RS-7 wherein preferably k is 0.

12. The compound according to claim 11, wherein n is 60.

13. The compound according to claim 1, wherein $R^5$ and $R^6$ are H.

14. A method comprising using a compound of claim 1 as electron acceptor or n-type semiconductor in a semiconducting material, organic electronic device or component of an organic electronic device.

15. A composition comprising two or more fullerene derivatives, one or more of which is a compound of claim 1.

16. A composition comprising one or more compounds of claim 1 as electron acceptor or n-type semiconductor component, and further comprising one or more semiconducting compounds which have electron donor or p-type properties.

17. A composition comprising one or more compounds of claim 1 and one or more p-type organic semiconductor compounds selected from conjugated organic polymers.

18. A composition comprising one or more compounds of claim 1 and one or more compounds which are selected from compounds having one or more of a semiconducting, charge transport, hole transport, electron transport, hole blocking, electron blocking, electrically conducting, photoconducting, photoactive and light emitting property.

19. A method comprising using a compound of claim 1 as semiconducting, charge transport, electrically conducting, photoconducting, photoactive, thermoelectric material or light emitting material, or in an electronic device, or in a component of such an electronic device or in an assembly comprising such an electronic device or such a component.

20. A semiconducting, charge transport, electrically conducting, photoconducting, photoactive, thermoelectric or light emitting material, which comprises a compound of claim 1.

21. A formulation comprising a compound of claim 1, and further comprising one or more organic solvents.

22. An electronic device, or a component thereof, or an assembly comprising it, which is prepared using a formulation of claim 21.

23. An electronic device, or a component thereof, or an assembly comprising it, which comprises a compound of claim 1.

24. The electronic device according to claim 22, which is an optical, electrooptical, electronic, electroluminescent, photoluminescent, photoactive or thermoelectric device.

25. The electronic device according to claim 22, which is selected from organic field effect transistors (OFET), organic thin film transistors (OTFT), organic light emitting diodes (OLED), organic light emitting transistors (OLET), organic photovoltaic devices (OPV), organic photodetectors (OPD), organic solar cells, dye sensitized solar cells (DSSC), perovskite-based solar cells, thermoelectric devices, laser diodes, Schottky diodes, photoconductors and photodetectors.

26. The component of claim 23, which is selected from charge injection layers, charge transport layers, interlayers, planarising layers, antistatic films, polymer electrolyte membranes (PEM), conducting substrates and conducting patterns.

27. The assembly of claim 23, which is selected from integrated circuits (IC), radio frequency identification (RFID) tags or security markings or security devices containing them, flat panel displays or backlights thereof, electrophotographic devices, electrophotographic recording devices, organic memory devices, sensor devices, biosensors and biochips.

28. The electronic device according to claim 25, which is a bulk heterojunction (BHJ) OPV device or an inverted BHJ OPV device.

29. A bulk heterojunction which comprises, or is being formed from, the composition of claim 17.

30. The compound according to claim 1, wherein $R^2$, $R^3$ and $R^4$ are H and $R^1$ is selected from formulae P-RS-1 or P-RS-7 as defined in claim 1.

* * * * *

UNITED STATES PATENT AND TRADEMARK OFFICE
CERTIFICATE OF CORRECTION

PATENT NO. : 10,374,162 B2
APPLICATION NO. : 15/312448
DATED : August 6, 2019
INVENTOR(S) : Nicolas Blouin It is certified that error appears in the above-identified patent and that said Letters Patent is hereby corrected as shown below:

In the Claims

Claim 1 should read:
1. A compound of formula I

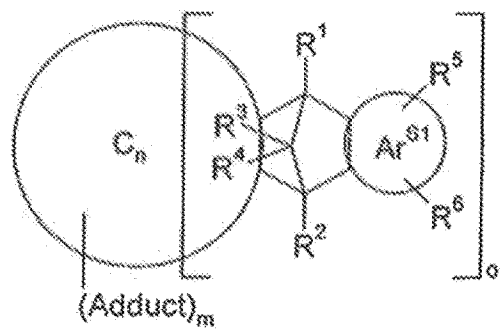

$C_n$ denotes a fullerene composed of n carbon atoms, optionally with one or more atoms trapped inside, Adduct is a secondary adduct, or a combination of secondary adducts, appended to the fullerene $C_n$ with any connectivity, m is 0, an integer $\geq 1$, or a non-integer $> 0$, o is an integer $\geq 1$, $Ar^{S1}$ denotes an aryl or heteroaryl group with 5 to 20, preferably 5 to 15, ring atoms, which is mono- or polycyclic, $R^1$ to $R^6$ denote, independently of each other, H, halogen, CN, $R^7$, $R^8$ or $R^9$, $R^7$ denotes, on each occurrence identically or differently, a saturated or unsaturated, non-aromatic carbo- or heterocyclic group, or an aryl, heteroaryl, aryloxy or heteroaryloxy group, wherein each of the aforementioned groups has 3 to 20 ring atoms, is mono- or polycyclic, does optionally contain fused rings, and is optionally substituted by one or more halogen atoms or CN groups, or by one or more identical or different groups $R^8$ or $R^9$, $R^8$ denotes, on each occurrence identically or differently, an alkyl group with 1 to 30 C atoms, which is straight-chain, branched or cyclic, and in which one or more $CH_2$ groups are Signed and Sealed this
Thirty-first Day of October, 2023

Katherine Kelly Vidal
*Director of the United States Patent and Trademark Office* optionally replaced by -O-, -S-, -C(=O)-, -C(=S)-, -C(=O)-O-, -O-C(=O)-, -NR$^0$-, -C(=O)-NR$^0$-, -NR$^0$-C(=O)-, -SiR$^0$R$^{00}$-, -CF$_2$-, -CHR$^0$=CR$^{00}$-, -CY$^1$=CY$^2$- or -C≡C- in such a manner that O and/or S atoms are not linked directly to one another, and in which one or more H atoms are optionally replaced by F, Cl, Br, I or CN, R$^9$ denotes, on each occurrence identically or differently, a straight-chain, branched or cyclic alkyl group with 1 to 50, preferably 2 to 50, more preferably 2 to 25, most preferably 2 to 12 C atoms, in which one or more CH$_2$ or CH$_3$ groups are replaced by a cationic or anionic group, Y$^1$ and Y$^2$ denote, independently of each other, H, F, Cl or CN, R$^0$ and R$^{00}$ denote, independently of each other, H or an optionally substituted carbyl or hydrocarbyl group having 1 to 40 C atoms, with the provisos that a) at least one of R$^1$, R$^2$, R$^3$ and R$^4$ is different from H, and b) if n = 70, then R$^1$ is different from -C(=O)-O-CH$_3$ if R$^2$ is H, and R$^2$ is different from -C(=O)-O-CH$_3$ if R$^1$ is H, and wherein when R$^1$, R$^2$, R$^3$ and R$^4$ are different from H, they are selected from the following formulae

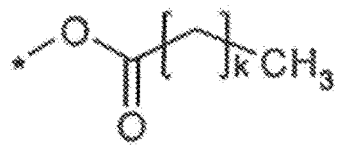

(P-RS-1)

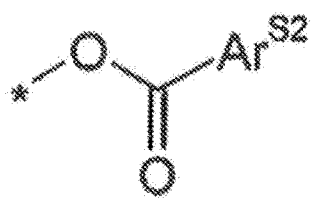

(P-RS-2)

(P-RS-3)

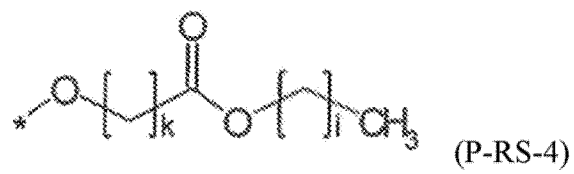
(P-RS-4)
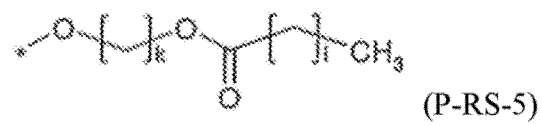
(P-RS-5)
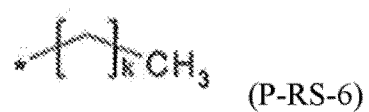
(P-RS-6)
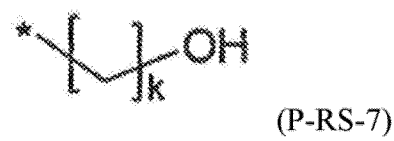
(P-RS-7)
wherein
$Ar^{S2}$ denotes $R^7$ or has one of the meanings of $Ar^{S1}$,
i is 0 or an integer from 1 to 9,
k is 0 or an integer from 1 to 9.